US005789543A

United States Patent [19]

Ingham et al.

[11] Patent Number: 5,789,543

[45] Date of Patent: Aug. 4, 1998

[54] VERTEBRATE EMBRYONIC PATTERN-INDUCING PROTEINS AND USES RELATED THERETO

[75] Inventors: Philip W. Ingham, Summertown, England; Andrew P. McMahon, Lexington; Clifford J. Tabin, Cambridge, both of Mass.

[73] Assignee: President and Fellows of Harvard College, Cambridge, Mass.

[21] Appl. No.: 176,427

[22] Filed: Dec. 30, 1993

[51] Int. Cl.[6] .................................................. C07K 14/00
[52] U.S. Cl. ......................... 530/350; 530/300; 435/69.1; 424/185.1
[58] Field of Search .......................... 530/350, 300; 435/69.1; 424/185.1

[56] References Cited

PUBLICATIONS

Development vol. 111, pp. 531–542, 1991. Jones et al.
The EMBO Journal vol. 10 No. 13, pp. 4177–4187 1991. Zappavigna.
P.N.A.S. vol. 88 pp. 4250–4254 May 1991. Lee, Se–Jin.
Anderson, R. et al., "Maintenance of ZPA signaling in cultured mouse limb bud cells", Devel. 117:1421–1433 (1993).
Basler, K. et al., "Control of Cell Pattern in the Neural Tube: Regulation of Cell Differentiation by dorsalin–1, a Novel TGFβ Family Member", Cell 73:687–702 (1993).
Bejsovec, A. and E. Wieschaus, "Segment polarity gene interactions modulate epidermal patterning in Drosophila embryos", Development 119:501–517 (1993).
Brand–Saberi, B. et al., "The ventralizing effect of the notochord on somite differentiation in chick embryos", Anat. Embryol. 188:239–245 (1993).
Brockes, J., "We may not have a morphogen", Nature 350:15 (1991).
Davidson, E.H., "How embryos work: a comparative view of diverse modes of cell fate specification", Devel. 108:365–389 (1990).
Dollé, P. et al., "Coordinate expression of the murine Hox–5 complex homoeobox–containing genes during limb pattern formation", Nature 342:767–772 (1989).
Dollé, P. et al., "Disruption of the Hoxd–13 Gene Induces Localized Heterochrony Leading to Mice with Neotenic Limbs", Cell 75:431–441 (1993).
Fahrner, K. et al., "Transcription of H–2 and Qa genes in embryonic and adult mice", EMBO J. 6:1265–1271 (1987).
Forbes, A.J. et al., "Genetic analysis of hedgehog signalling in the Drosophila embryo", Devel. 119 (Suppl.):115–124 (1993).
Gérard, M. et al., "Structure and activity of regulatory elements involved in the activation the the Hoxd–11 gene during late gastrulation", EMBO J. 12:3539–3550 (1993).
Gurdon, J.B., "The Generation of Diversity and Pattern in Animal Development", Cell 68:185–199 (1992).
Halpern, M.E., "Induction of Muscle Pioneers and Floor Plate Is Distinguished by the Zebrafish no tail Mutation", Cell 75:99–111 (1993).

Hamburger, V. and H.L. Hamilton, "A Series Of Normal Stages In The Development Of The Chick Embryo", J. Morph. 88:49–92 (1951).
Hatta, K. et al., "The cyclops mutation blocks specification of the floor plate of the zebrafish central nervous system", Nature 350:339–341 (1991).
Heberlein, U. et al., "The TGBβ Homolog dpp and the Segment Polarity Gene hedgehog Are Required for Propagation of a Morphogenetic Wave in the Drosophila Retina", Cell 75:913–926 (1993).
Hidalgo, A. and P. Ingham, "Cell patterning in Drosophila segment: spatial regulation of the segment polarity gene patched", Development 110:291–301 (1990).
Hynes, R.O., "Integrins: A Family of Cell Surface Receptors", Cell 48:549–554 (1987).
Ingham, P.W., "Localized hedgehog activity controls spatial limits of wingless transcription in the Drosophila embryo", Nature 366:560–562 (1993).
Ingham, P.W. and A. Hidalgo, "Regulation of wingless transcription in the Drosophila embryo", Devel. 117:283–291 (1993).
Ingham, P.W. et al., "Role of the Drosophila patched gene in positional signalling", Nature 353:184–187 (1991).
Izpisúa–Belmonte, J.–C. et al., "Expression of the homeobox Hox–4 genes and the specification of position in chick wing development", Nature 350:585–589 (1991).
Izpisúa–Belmonte, J.–C. et al., "Expression of Hox–4 genes in the chick wings links pattern formation to the epithelial–mesenchymal interactions that mediate growth", EMBO J. 11:1451–1457 (1992).
Jessel, T.M. and D.A. Melton, "Diffusible Factors in Vertebrate Embryonic Induction", Cell 68:257–270 (1992).
Kornblihtt, A.R. et al., "Primary structure of human fibronectin: differential splicing may generate at least 10 polypeptides from a single gene", EMBO J. 4:1755–1759 (1985).
Kornfeld, R. and S. Kornfeld, "Assembly Of Asparagine–Linked Oligosaccharides", Ann. Rev. Biochem. 54:631–664 (1985).
Krauss, S. et al., "Expression of the zebrafish paired box gene pax[zf–b] during early neurogenesis", Devel. 113:1193–1206 (1991).
Lee, J.J. et al., "Secretion and Localized Transcription Suggest a Role in Positional Signaling for Prodcuts of the Segmentation Gene hedgehog", Cell 71:33–50 (1992).

(List continued on next page.)

Primary Examiner—Stephen Walsh
Assistant Examiner—Kenneth A. Sorensen
Attorney, Agent, or Firm—Matthew P. Vincent; Beth E. Arnold; Foley, Hoag & Eliot LLP

[57] ABSTRACT

The present invention concerns the discovery that proteins encoded by a family of vertebrate genes, termed here hedgehog–related genes, comprise morphogenic signals produced by embryonic patterning centers, and are involved in the formation of ordered spatial arrangements of differentiated tissues in vertebrates. The present invention makes available compositions and methods that can be utilized, for example to generate and/or maintain an array of different vertebrate tissue both in vitro and in vivo.

35 Claims, 15 Drawing Sheets

OTHER PUBLICATIONS

Ma, C. et al., "The Segment Polarity Gene hedgehog Is Required for Progression of the Morphogenetic Furrow in the Developing Drosophila Eye", *Cell* 75:927–938 (1993).

Maccabe, J.A. and B.W. Parker, "The target tissue of limb-bud polarizing activity in the induction of supernumerary structures", *J. Embryol. exp. Morph.* 53:67–73 (1979).

Mavilio, F. et al., "Activation of four homeobox gene clusters in human embryonal carcinoma cells induced to differentiate by retinoic acid", *Differentiation* 37:73–79 (1988).

McGinnis, W. and R. Krumlauf, "Homeobox Genes and Axial Patterning", *Cell* 68:283–302 (1992).

Mohler, J., "Requirements for hedgehog, a Segmental Polarity Gene, in Patterning Larval and Adult Cuticle of Drosophila", *Genetics* 120:1061–1072 (1988).

Mohler, J. and K. Vani, "Molecular organization and embryonic expression of the hedgehog gene involved in cell–cell communication in segmental patterning of Drosophila", *Devel.* 115:957–971 (1992).

Morgan, B.A. et al., "Targeted misexpression of Hox–4.6 in the avian limb bud causes apparent homeotic transformations", *Nature* 358:236–239 (1992).

Niswander, L. and G.R. Martin, "FGF–4 and BMP–2 have opposite effects on limb growth", *Nature* 361:68–71 (1993).

Nohno, T. et al., "Involvement of the Chox–4 Chicken Homeobox Genes in Determination of Anteroposterior Axial Polarity during Limb Development", *Cell* 64:1197–1205 (1991).

Parr, B.A. et al., "Mouse Wnt genes exhibit discrete domains of expression in the early embryonic CNS and limb buds", *Devel.* 119:247–261 (1993).

Patel, N.H. et al., "The role of segment polarity genes during Drosophila neurogenesis", *Genes Devel.* 3:890–904 (1989).

Placzek, M. et al., "Induction of floor plate differentiation by contact–dependent, homeogenetic signals", *Devel.* 117:205–218 (1993).

Placzek, M. et al., "Orientation of commissural axons in vitro in response to a floor plate–derived chemoattractant", *Devel.* 110:19–30 (1990).

Pollack, R.A. et al., "Altering the Boundaries of Hox3.1 Expression: Evidence for Antipodal Gene Regulation", *Cell* 71:911–923 (1992).

Riley, B.B. et al., "Retroviral expression of FGF–2 (bFGF) affects patterning in chick limb bud", *Devel.* 118:95–104 (1993).

Sasaki, H. and B.L.M. Hogan, "Differential expression of multiple fork head related genes during gastrulation and axial pattern formation in the mouse embryo", *Devel.* 118:47–59 (1993).

Stachel, S.E. et al., "Lithium perturbation and goosecoid expression identify a dorsal specification pathway in the pregastrula zebrafish", *Devel.* 117:1261–1274 (1993).

Tabata, T. et al., "The *Drosophila hedgehog* gene is expressed specifically in posterior compartment cells and is a target of engrailed regulation", *Genes Devel.* 6:2635–2645 (1992).

Tabin, C.J., "Retinoids, Homeoboxes, and Growth Factors: Toward Molecular Models for Limb Development", *Cell* 66:199–217 (1991).

Tashiro, S. et al., "Structure and expression of hedgehog, a Drosophila segment–polarity gene required for cell–cell communication", *Gene* 124:183–189 (1993).

Taylor, A.M. et al., "Contrasting distributions of patched and hedgehog proteins in the Drosophila embryo", *Mech. Dev.* 42:89–96 (1993).

Thaller, C. and G. Eichle, "Identification and spatial distribution of retinoids in the developing chick limb bud", *Nature* 327:625–628 (1987).

Tickle, C. et al., "A Quantitative Analysis of the Effect of all–trans–Retinoic Acid on the Pattern of Chick Wing Development", *Devel. Biol.* 109:82–95 (1985).

van Straaten, H.W.M. et al., "Effect of the notochord on the differentiation of a floor plate area in the neural tube of the chick embryo," *Anat. Embryol.* 177:317–324 (1988).

Vogel, A. and C. Tickle, "FGF–4 maintains polarizing activity of posterior limb bud cells in vivo and in vitro", *Devel.* 119:199–206 (1993).

Wanek, N. et al., "Conversion by retinoic acid of anterior cells into ZPA cells in the chick wing bud", *Nature* 350:81–83 (1991).

Yamada, T. et al., "Control of Cell Pattern in the Developing Nervous System: Polarizing Activity of the Floor Plate and Notochord", *Cell* 64:635–647 (1991).

```
DROSOPHILA HEDGEHOG   R C K E K L N V L A Y S V M N E W P G I R L L V T
CHICKEN HEDGEHOG-A    R C K E R V N S L A I A V M H M W P G V R L R V T
CHICKEN HEDGEHOG-B    R C K D K L N A L A I S V M N Q W P G V K L R V T

DROSOPHILA HEDGEHOG   E S W D E D Y H H G Q E S L H Y E G R A V T I A T
CHICKEN HEDGEHOG-A    E G W D E D G H H L P D S L H Y E G R A L D I T T
CHICKEN HEDGEHOG-B    E G W D E D G H H S E E S L H Y E G R A V D I T T

DROSOPHILA HEDGEHOG   S D R D Q S K Y G M L A R L A V E A G F D W V
CHICKEN HEDGEHOG-A    S D R D R H K Y G M L A R L A V E A G F D W V
CHICKEN HEDGEHOG-B    S D R D R S K Y G M L A R L A V E A G F D W V
```

*FIG. 1*

Body Leg

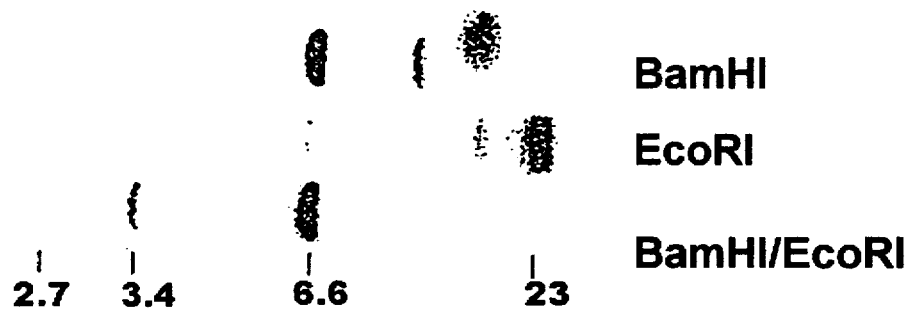
FIG. 6

```
      1
D-hh   MDNHSSVPWA  SAASVTCLSL  DAKCHSSSSS  SSSKSAASSI  SAIPQEETQT
M-Dhh  ..........  ..........  ..........  ..........  ..........
M-Ihh  ..........  ..........  ..........  ..........  ..........
M-Shh  ..........  ..........  ..........  ..........  ..........
C-Shh  ..........  ..........  ..........  ..........  ..........
Z-Shh  ..........  ..........  ..........  ..........  ..........

51
D-hh   MRHIAHTQRC  LSRLTSLVAL  LLIVLPMVFS  PAHSCGPGRG  LGRHR...AR
M-Dhh  ..........  ..MALPASLL  PLCCLALLAL  SAQSCGPGRG  PVGRRRYVRK
M-Ihh  ..........  ..........  ..........  ..........  ..........
M-Shh  ..........  MLLLARCFL   VILASSLLVC  PGLACGPGRG  FGKRRH..PK
C-Shh  ..........  EMLLLTRILL  VGFICALLVS  SGLTCGPGRG  IGKRRH..PK
Z-Shh  ......MV    .MRLLTRVLL  VSLLTLSLVV  SGLACGPGRG  YGRRRH..PK

101
D-hh   NLYPLVLKQT  IPNLSEYTNS  ASGPLEGVIR  RDSPKPKDLV  PNYNRDILFR
M-Dhh  QLVPLLYKQF  VPSMPERTLG  ASGPAEGRVT  RGSERFRDLV  PNYNPDIIPK
M-Ihh  ..........  ..........  ..........  ...ERPKELT  PNYNPDIIPK
M-Shh  KLTPLAYKQF  IPNVAEKTLG  ASGRYEGKIT  RNSERFKELT  PNYNPDIIPK
C-Shh  KLTPLAYKQF  IPNVAEKTLG  ASGRYEGKIT  RNSERFKELT  PNYNPDIIPK
Z-Shh  KLTPLAYKQF  IPNVAEKTLG  ASGRYEGKIT  RNSERFKELT  PNYNPDIIPK

151
D-hh   DEEGTGADRL  MSKRCKEKLN  VLAYSVMNEH  PGIRLLYTES  WDEDYHGQE
M-Dhh  DEENSGADRL  MTERCKERVN  ALAIAVMMW   PGVRLRVTEG  WDEDGHHAQD
M-Ihh  DEENTGADRL  MTQRCKDRLN  SLAISVMNQW  PGVKLRVTEG  RDEDGHHSEE
M-Shh  DEENTGADRL  MTQRCKDKLN  ALAISVMNQH  PGVRLRVTEG  WDEDGHHSEE
C-Shh  DEENTGADRL  MTQRCKDKLN  ALAISVMNQW  PGVKLRVTEG  WDEDGHHSEE
Z-Shh  DEENTGADRL  MTQRCKDKLN  SLAISVMNHW  PGVKLRVTEG  WDEDGHHFEE
```

FIG. 7(1)

```
       201
D-hh   SLHYEGRAVT  IATSDRDQSK  YGMLARLAVE  AGPDWVSYVS  RRHIYCSVKS
M-Dhh  SLHYEGRALD  ITTSDRDRNK  YGLLARLAVE  AGPDWVYYES  RNHIHVSVRA
M-Ihh  SLHYEGRAVD  ITTSDRDRNK  YGLLARLAVE  AGPDWVYYES  KAHVHCSVKS
M-Shh  SLHYEGRAVD  ITTSDRDRSK  YGMLARLAVE  AGPDWVYYES  KAHIHCSVKA
C-Shh  SLHYEGRAVD  ITTSDRDRSK  YGMLARLAVE  AGPDWVYYES  KAHIHCSVKA
Z-Shh  SLHYEGRAVD  ITTSDRDKSK  YGTLSRLAVE  AGPDWVYYES  KAHIHCSVKA

251
D-hh   DSSISSHVHG  CFTPESTALL  ESGVRKPLGE  LSIGDRVLSM  TANGQAVYSE
M-Dhh  DNSLAVRAGG  CFPGNATVRL  RSGERKGLRE  LHRGDWVLAA  DAAGRVVPTP
M-Ihh  EHSAAAKTGG  CFPAGAQVRL  ENGERVALSA  VKPGDRVLAM  GEDGTPTFSD
M-Shh  ENSVAAKSGG  CFPGSATVHL  EQGGTKLVKD  LRPGDRVLAA  DDQGRLLYSD
C-Shh  ENSVAAKSGG  CFPGSATVHL  EHGGTKLVKD  LSPGDRVLAA  DADGRLLYSD
Z-Shh  ENSVAAKSGG  CFPGSALVSL  QDGGQKAVKD  LNPGDKVLAA  DSAGNLVFSD

301
D-hh   VILPMDRNLE  QMQNFVQLHT  .DGGAVLTVT  PAHLVSVWQ.  ......PESQ
M-Dhh  VLLPLDRDLQ  RRASPVAVET  ERPPRKLLLT  PWHLVFAAR.  ...GPAPAPG
M-Ihh  VLIPLDREPN  RLRAPQVIET  QDPPRRLALT  PAHLLFIADN  HTE....PAA
M-Shh  FLTPLDRDEG  AKKVFYVIET  LEPRERLLLT  AAHLLFVAP.  HNDSGPTPGP
C-Shh  FLTPLDRMDS  SRKLFYVIET  RQPRARLLLT  AAHLLFVAPQ  HNQSEATGST
Z-Shh  FIMPTDRDST  TRRVFYVIET  QEPVEKITLT  AAHLLFVLDN  STEDLHTMT.

351
D-hh   KLTFVFADRI  EEKNQVLV..  RDVETGELRP  QRVVKVG.SV  RSKGVVAPLT
M-Dhh  DFAPVFARRL  RAGDSVLA..  ..PGGDALQP  ARVARVA.RE  EAVGVFAPLT
M-Ihh  HFRATFASHV  QPGQYVLV..  ..SGVPGLQP  ARVAAVS.TH  VALGSYAPLT
M-Shh  S..ALFASRV  RPGQRVYVA  ERGGDRRLLP  AAVHSVTLRE  EEAGAYAPLT
C-Shh  SGQALFASNV  KPGQRVYVLG  E..GGQQLLP  ASVHSVSLRE  EASGAYAPLT
Z-Shh  ...AAYASSV  RAGQKVMVVD  DSGQLKSVIV  QRIYT....E  EQRGSFAPVT
```

*FIG. 7(2)*

```
       401
D-hh   REGTIVVNSV  AASCYAVINS  QSLAHWGLAP  MRLLSTLEAW  LPAKEQLHSS
M-Dhh  AHGTLLVNDV  LASCYAVLES  HQWAHRAFAP  LRLLHALGAL  LP........
M-Ihh  RHGTLVVEDV  VASCFAAVAD  HHLAQLAFWP  LRLFPSL...  ..........
M-Shh  AHGTILINRV  LASCYAVIEE  HSWAHRAFAP  FRLAHALLAA  LAPARTDGGG
C-Shh  AQGTILINRV  LASCYAVIEE  HSWAHMAFAP  FRLAQGLLAA  LCP.......
Z-Shh  AHGTIVVDRI  LASCYAVIED  QGLAHLAFAP  ARLYYYVSSF  LSP.......

451
D-hh   PKVV......  ...SSAQQQN  GIHWYANALY  KVKDYVLPQS  WRHD*
M-Dhh  ..........  ...GGAVQPT  GMHWYSRLLY  RLAEELMG*
M-Ihh  ..........  .AWGSWTPSE  GVHSYPQMLY  RLGRLLEES   TFHPLGMSGA
M-Shh  GGSIPAAQSA  TEARGAEPTA  GIHWYSQLLY  HIGTWLLDSE  RMHPLGMAVK
C-Shh  DGAIPTA...  ....ATYTT   GIHWYSRLLY  RIGSWVLDGD  ALHPLGMVAP
Z-Shh  KTPAVGPMRL  YNRRGSTGTP  GSC......H  QMGTWLLDSN  MLHPLGMSVN

501
M-Ihh  GS*
M-Shh  SS*
C-Shh  AS*
Z-Shh  SS*
```

*FIG. 7(3)*

|  | M-Dhh | M-Ihh | C-Shh | Zf-Shh | D-hh |
|---|---|---|---|---|---|
| M-Shh | 61 (77) | 63 (78) | 84 (92) | 68 (80) | 48 (64) |
| M-Dhh |  | 58 (75) | 61 (77) | 54 (71) | 51 (68) |
| M-Ihh |  |  | 64 (78) | 61 (75) | 48 (68) |
| C-Shh |  |  |  | 68 (80) | 49 (64) |
| Zf-Shh |  |  |  |  | 47 (64) |

*FIG. 8*

```
hh    1    MDNHSSVPWASAASVTCLSLDAKCHSSSSSSSKSAASSISAIPQEETQT
shh        ................................................

hh   51    MRHIAHTQRCLSRLTSLVALLLIVLPMVFSPAHSCGPGRGLGRHR..ARNL
                 ||||| || |||||| |  ||| |||| |||||||||||  ||||
shh   1    .......MRLLTRVLLVSLLTLSLVVS.GLACGPGRGYGRRRHPKKL hh  100    YPLVLKQTIPNLSEYTNSASGPLEGVIRRDSPKFKDLVPNYNRDILFRDE
           ||  | | |||| |   |||||| ||| ||||| |||||||| ||||||
shh  40    TPLAYKQFIPNVAEKTLGASGRYEGKITRNSERFKELTPNYNPDIIFKDE
                                        ▼
hh  150    EGTGADRLMSKRCKEKLNVLAYSVMNEWPGIRLVVTESWDEDYHHGQESL
           |  |||||| | |||||| |  ||||  | || || ||||  |  |||
shh  90.   ENTGADRLMTQRCKDKLNSLAISVMNHWPGVKLRVTEGWDEDGHHFEESL
                                                              ▼
hh  200    HYEGRAVTIATSDRDQSKYGMLARLAVEAGFDWVSYVSRRHIYCSVKSDS
           ||||||| | |||||||||  || ||||||||| |     || ||||
shh 140    HYEGRAVDITTSDRDKSKYGTLSRLAVEAGFDWVYYESKAHIHCSVKAEN hh  250    SISSHVHGCFTPESTALLESGVRKPLGELSIGDRVLSMTANGQAVYSEVI
           |||   ||||||| ||| |||  |||  | |||||  |  |  |  ||
shh 190    SVAAKSGGCFPGSALVSLQDGGQKAVKDLNPGDKVLAADSAGNLVFSDFI
```

*FIG. 11 (A1)*

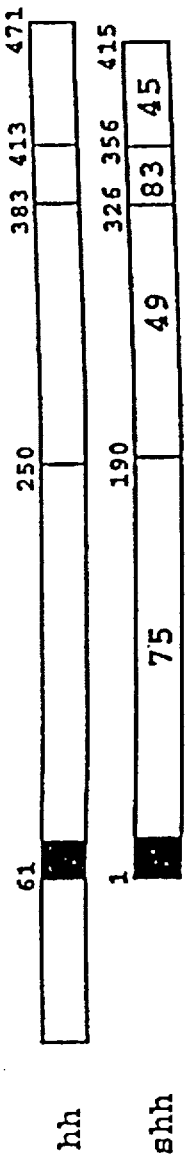

```
hh  300  LFMDRNLEQMQNFVQLHT.DGGAVLTVTPAHLVSVWQPESQKL...TFVF
              |||    |||  |||   |||| |||   ||         ||||
shh 240  MFTDRDSTTRRVFYVIETQEPVEKITLTAAHLLFVLDNSTEDLHTMTAAY hh  347  ADRIEEKNQVLVRDVETGELRPQRVVKVGSVRSKGVVAPLTREGTIVVNS
         |  |||||      ||   |||||||||       ||||     ||||
shh 290  ASSVRAGQKVMVVD.DSGQLKSVIVQRIYTEEQRGSFAPVTAHGTIVVDR hh  397  VAASCYAVINSQSLAHWGLAPMRLLSTLEAWLPAKEQL........HSS
         ||||||| ||   || |||| |||
shh 339  ILASCYAVIEDQGLAHLAFAPARLYYVSSFLSPKTPAVGPMRLYNRRGS hh  438  PKVVSSAQQQNGIHWYANALYKVKDYVLPQSWRHD 471
              |              ||
shh 389  TGTPGSCHQMGTWLLDSNMLHPLGMSV........ 415
```

```
hh    KRCKEKLNVLAYSVMNEWPGIRLVVTESWDEDYHHGQESLHYEGRAVTIATSDRDQSKYGMLAR
      ||| ||| || |||| ||| ||| |||  ||||   |||||||||| | ||||||    |||
shh   QRCKDKLNSLAISVMNHWPGVKLRVTEGWDEDGHHFEESLHYEGRAVDITTSDRDKSKYGTLSR
      ||| ||| || |||| ||| ||| |||  ||| ||||||||||||| |||||||  |||| |
hh[a] QRCKEKLNSLAISVMNMWPGVKLRVTEGWDEDGNHFEDSLHYEGRAVDITTSDRDRNKYGMFAR
      ||| ||| || |||| ||| ||| |||  ||| ||||||||||||| |||||||||||| ||
hh[b] QRCKDKLNSLAISVMNLWPGVKLRVTEGWDEDGLHSEESLHYEGRAVDITTSDRDRNKYRMLAR
```

*FIG. 12*

VERTEBRATE EMBRYONIC PATTERN-INDUCING PROTEINS AND USES RELATED THERETO

FUNDING

Work described herein was supported by funding from the National Institutes of Health. The United States Government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diversive cell types during tissue differentiation (Davidson, E., (1990) Development 108: 365–389; Gurdon, J. B., (1992) Cell 68: 185–199; Jessell, T. M. et al., (1992) Cell 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) Cell 68: 185–199).

The origin of the nervous system in all vertebrates can be traced to the end of gastrulation. At this time, the ectoderm in the dorsal side of the embryo changes its fate from epidermal to neural. The newly formed neuroectoderm thickens to form a flattened structure called the neural plate which is characterized, in some vertebrates, by a central groove (neural groove) and thickened lateral edges (neural folds). At its early stages of differentiation, the neural plate already exhibits signs of regional differentiation along its anterior posterior (A-P) and mediolateral axis (M-L). The neural folds eventually fuse at the dorsal midline to form the neural tube which will differentiate into brain at its anterior end and spinal cord at its posterior end. Closure of the neural tube creates dorsal/ventral differences by virtue of previous mediolateral differentiation. Thus, at the end of neurulation, the neural tube has a clear anterior-posterior (A-P), dorsal ventral (D-V) and mediolateral (M-L) polarities (see, for example, Principles in Neural Science (3rd), eds. Kandel, Schwartz and Jessell, Elsevier Science Publishing Company: N.Y., 1991; and Developmental Biology (3rd), ed. S. F. Gilbert, Sinauer Associates: Sunderland Mass., 1991). Inductive interactions that define the fate of cells within the neural tube establish the initial pattern of the embryonic vertebrate nervous system. In the spinal cord, the identify of cell types is controlled, in part, by signals from two midline cell groups, the notochord and floor plate, that induce neural plate cells to differentiate into floor plate, motor neurons, and other ventral neuronal types (van Straaten et al. (1988) Anat. Embryol. 177: 317–324; Placzek et al. (1993) Development 117: 205–218; Yamada et al. (1991) Cell 64: 035–647; and Hatta et al. (1991) Nature 350: 339–341). In addition, signals from the floor plate are responsible for the orientation and direction of commissural neuron outgrowth (Placzek, M. et al., (1990) Development 110: 19–30). Besides patterning the neural tube, the notochord and floor-plate are also responsible for producing signals which control the patterning of the somites by inhibiting differentiation of dorsal somite derivatives in the ventral regions (Brand-Saberi, B. et al., (1993) Anat. Embryol. 188: 239–245; Porquie, O., et al., (1993) Proc. Natl. Acad. Sci. USA 90: 5242–5246).

Another important signaling center exists in the posterior mesechyme of developing limb buds, called the Zone of Polarizing Activity, or "ZPA". When tissue from the posterior region of the limb bud is grafted to the anterior border of a second limb bud, the resultant limb will develop with additional digits in a mirror-image sequence along the anteroposterior axis (Saunders and Gasseling, (1968) Epithelial-Mesenchymal Interaction, pp. 78–97). This finding has led to the model that the ZPA is responsible for normal anteroposterior patterning in the limb. The ZPA has been hypothesized to function by releasing a signal, termed a "morphogen", which forms a gradient across the early embryonic bud. According to this model, the fate of cells at different distances from the ZPA is determined by the local concentration of the morphogen, with specific thresholds of the morphogen inducing successive structures (Wolpert, (1969) Theor. Biol. 25: 1–47). This is supported by the finding that the extent of digit duplication is proportional to the number of implanted ZPA cells (Tickle, (1981) Nature 254: 199–202).

A candidate for the putative ZPA morphogen was identified by the discovery that a source of retinoic acid can result in the same type of mirror-image digit duplications when placed in the anterior of a limb bud (Tickle et al., (1982) Nature 296: 564–565; Summerbell, (1983) J Embryol 78: 269–289). The response to exogenous retinoic acid is concentration dependent as the morphogen model demands (Tickle et al., (1985) Dev. Biol. 109: 82–95). Moreover, a differential distribution of retinoic acid exists across the limb bud, with a higher concentration in the ZPA region (Thaller and Eichele, (1987) Nature 327: 625–628).

Recent evidence, however, has indicated that retinoic acid is unlikely to be the endogenous factor responsible for ZPA activity (reviewed in Brockes, (1991) Nature 350: 15; Tabin, (1991) Cell 66: 199–217). It is now believed that rather than directly mimicking an endogenous signal, retinoic acid implants act by inducing an ectopic ZPA. The anterior limb tissue just distal to a retinoic acid implant and directly under the ectoderm has been demonstrated to acquire ZPA activity by serially transplanting that tissue to another limb bud (Summerbell and Harvey, (1983) Limb Development and Regeneration pp. 109–118; Wanek et al., (1991) Nature 350: 81–83). Conversely, the tissue next to a ZPA graft does not gain ZPA activity (Smith, (1979) J. Embryol 52: 105–113). Exogenous retinoic acid would thus appear to act upstream of the ZPA in limb patterning.

The immediate downstream targets of ZPA action are not known. However, one important set of genes which are ectopically activated during ZPA-induced pattern duplications are the 5' genes of the Hoxd cluster. These genes are normally expressed in a nested pattern emanating from the posterior margin of the limb bud (Dolle et al., (1989) Nature 342: 767–772; Izpisua-Belmonte et al., (1991) Nature 350: 585–589). This nested pattern of Hox gene expression has been directly demonstrated to determine the identity of the structures produced along the anteroposterior axis of the limb (Morgan et al., (1993) Nature 358: 236–239). As this would predict, ZPA grafts which produce mirror-image duplication of structures at an anatomical level first lead to the ectopic activation of the Hoxd genes in a mirror-image duplication at the molecular level. (Nohno et al., (1991) *Cell* 64: 1197–1205; Izisua-Belmonte et al., (1991) *Nature* 350: 585–589). The molecular signals which regulate the expression of these important genes are currently not understood.

SUMMARY OF THE INVENTION

The present invention makes available, for the first time, both recombinant hedgehog proteins which are encoded by genes derived from vertebrate organisms, and which are capable of functioning in one of either role of an agonist of at least one biological activity of said vertebrate hedgehog protein or an antagonist of at least one biological activity of said vertebrate hedgehog protein. In one embodiment, amino acid sequence of the subject proteins is represented by SEQ ID. No. 2, SEQ ID. No. 4, SEQ ID. No. 6, SEQ ID. No. 8, or SEQ ID. No. 10. In another embodiment, the amino acid sequence of the subject hedgehog homolog is at least 52 percent homologous with an amino acid sequence selected from a group consisting of residues 27–425 of SEQ ID. No. 2, residues 22–396 of SEQ ID. No. 4, residues 1–352 of SEQ ID. No. 6, residues 25–437 of SEQ ID. No. 8, and residues 24–418 of SEQ ID. No. 10. In yet another embodiment, the amino acid sequence of the subject protein is at least 63 percent homology with an amino acid sequence selected from a group consisting of residues 27–189 of SEQ ID. No. 2, residues 22–187 of SEQ ID. No. 4, residues 1–116 of SEQ ID. No. 6, residues 25–187 of SEQ ID. No. 8, and residues 24–186 of SEQ ID. No. 10.

Exemplary biological activity which the present vertebrate hh protein may have include the ability to induce formation and differentiation of the head, limbs, lungs, central nervous system (CNS), or mesodermal patterning of developing vertebrate embryos. In preferred embodiments, the biological activity can comprise an ability to regulate neurogenesis, such as a motor neuron inducing activity, a neuronal differentiation inducing activity, or a neuronal survival promoting activity. Hedgehog proteins of the present invention can also have bioligical activities which include an ability to regulate organogensis, such as through the ability to influence limb patterning, by, for example, a skeletal homeotic activity. The biological activity associated with the hedgehog proteins of the present invention can also include the ability to induce stem cell or germ cell differentiation, including the ability to induce differentiation of chondrocytes or an involvement in spermatogenesis.

The present invention further provides isolated hedgehog protein which is isolated from, or otherwise substantially free of other extracellular proteins, especially morphogenic proteins, normally associated with the vertebrate hedgehog protein. Similarly, the present invention relates to immunogens comprising a portion of a vertebrate hedgehog protein, which can have amino acid sequences which are antigenically distinct from other vertebrate and non-vertebrate hedgehog homologs.

The present invention also makes available isolated nucleic acids comprising nucleotide sequences encoding vertebrate hh homologs, and fragments thereof, encoding polypeptides having at least one biological activity of a vertebrate hh homolog, and/or equivalents of such nucleic acids.

Another aspect of the present invention relates to a method of inducing and/or maintaining a differentiated state of a cell responsive to a hedgehog protein, by contacting the cells with a hedgehog agonist. For instance, it is contemplated by the invention that, in light of the present finding of a broad involvement of hedgehog proteins in the formation of ordered spatial arrangements of differentiated tissues in vertebrates, the subject method could be used to generate and/or maintain an array of different vertebrate tissue both in vitro and in vivo. The subject method can be practiced with, for example, the goal of inducing neuronal differentiation.

BRIEF DESCRIPTION OF THE DRAWINGS

FIGS. 1 represents the amino acid sequences of two chick hh clones, chicken hedgehog-A (PCHA; SEQ ID NO: 12) and chicken hedgehog-B (pCHB; SEQ ID NO: 13). These clones were obtained using degenerate primers corresponding to the underlined amino acid residues of the Drosophila sequence (corresponding to residues 161–232 of SEQ ID NO: 11) also shown in FIG. 1, followed by nested PCR using chicken genomic DNA.

FIG. 2 is a Northern blot analysis performed on 20 μg total RNA from stage 24 limb buds, heads and trunks of chicks using Shh from pHH-2 as a probe. The message size was predicted by comparing it to the position of 18S and 28S ribosomal RNA. Hybridizing MRNA was visualized after a two day exposure to a phosphoscreen.

FIG. 3 is an alignment comparing the amino acid sequences of chick Shh (SEQ ID NO: 2) with its Drosophila homolog (SEQ ID NO: 11). Shh residues 1–26 correspond to the proposed signal peptide. Identical residues are enclosed by boxes and gaps in order to highlight similarity. The nucleotide sequence of Shh has been submitted to Genbank.

FIG. 6 is a Southern blot analysis of chick hh genes. The blot was generated by digesting 5 μg of chick chromosomal DNA with EcoRI and BamHI alone and together. The subsequent blots were probed with either chicken hedgehog-A (pCHA; SEQ ID NO: 12) or chicken hedgehog-B (pCHB; SEQ ID NO: 13). The numbers to the right of the blots refer to the calculated size (in kb) of hybridizing restriction fragments. Exposure times were 72 hours.

FIG. 7 is a "pileup" alignment of predicted amino acid sequences which compares Drosophila hh (D-hh; SEQ ID NO: 11), mouse hh (M-Dhh; SEQ ID NO: 4; M-Ihh; SEQ ID NO: 6; M-Shh; SEQ ID NO: 8), chicken hh (C-Shh; SEQ ID NO: 2), and zebrafish hh (Z-Shh; SEQ ID NO: 10). The predicted hydrophobic transmembrane/signal sequences are indicated in italics and the predicted signal sequence processing site is arrowed. The positions of introns interrupting the Drosophila hh and M-Dhh open reading frames are indicated by arrowheads. All amino acids shared among the six predicted hh proteins are indicated in bold.

FIG. 8 is an inter- and cross-species comparison of amino acid identities among the predicted processed hh proteins shown in FIG. 7. All values are percentages. Figures in parentheses represent similarities allowing for conservative amino acid substitutions.

FIGS. 11A and 11B illustrate the comparison of zebrafish Shh (Z-Shh) and Drosophila hh (hh) amino acid sequences. FIG. 11A is an alignment of zebrafish Shh and Drosophila hh amino acid sequences. Identical amino acids are linked by vertical bars. Dots indicate gaps introduced for optimal alignment. Putative transmembrane/signal peptide sequences are underlined (Kyte and Doolittle (1982) *J Mol Biol* 157: 133–148). The position of exon boundaries in the Drosophila gene are indicated by arrowheads. The region of highest similarity between Z-Shh and hh overlaps exon 2. FIG. 11B is a schematic comparison of Z-Shh and drosophila hh. Black boxes indicate the position of the putative transmembrane/signal peptide sequences, relative to the amino-terminus. Sequence homologies were scored by taking into account the alignment of chemically similar amino acids and percentage of homology in the boxed regions is indicated.

FIG. 12 is an alignment of partial predicted amino acid sequences from three different zebrafish hh homologs. One of these sequences corresponds to Shh, while the other two define additional hh homologs in zebrafish, named hh(a) and hh(b). Amino acid identities among the three partial homologs are indicated by vertical bars.

DETAILED DESCRIPTION OF THE INVENTION

Figure 4:
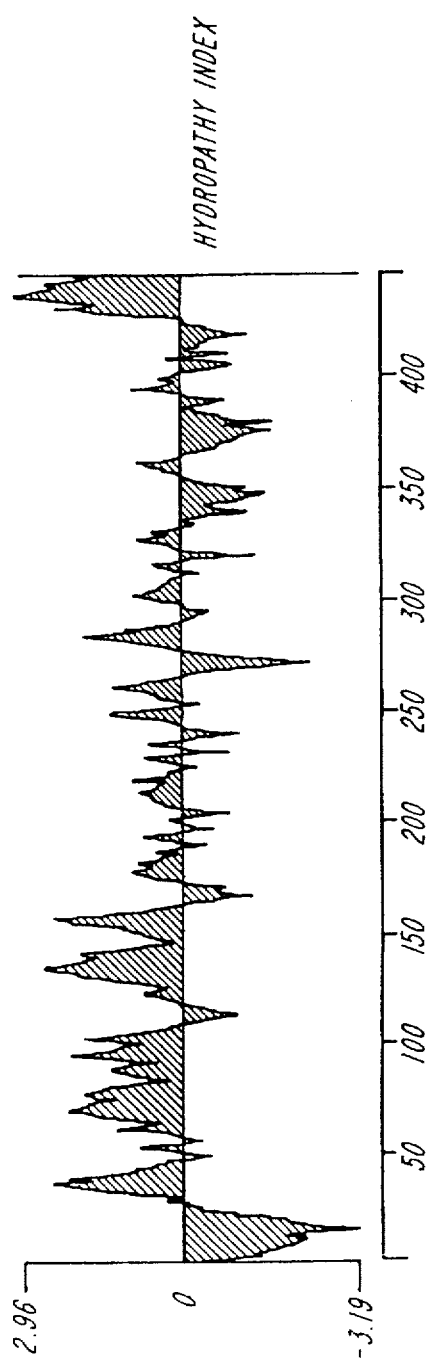
FIG. 4 is a hydropathy plot for the predicted chick Shh protein, generated by the methods of Kyte and Doolittle (1982). The values of hydrophobicity are plotted against the amino acid positions. Negative values predict a hydrophobic domain of the protein.

Embryonic inductive signals are key regulatory proteins that function in vertebrate pattern formation, and are present in important signaling centers known to operate embryonically to define the organization of the vertebrate embryo. For example, these signaling structures include the notochord, a transient structure which initiates the formation of the nervous system and helps to define the different types of neurons within it. The notochord also regulates mesodermal patterning along the body axis. Another distinct group of cells having apparent signaling activity is the floorplate of the neural tube (the precursor of the spinal cord and brain) which also signals the differentiation of different nerve cell types. It is also generally believed that the region of mesoderm at the bottom of the buds which form the limbs (called the Zone of Polarizing Activity or ZPA) operates as a signaling center by secreting a morphogen which ultimately produces the correct patterning of the developing limbs.

The present invention concerns the discovery that proteins encoded by a family of vertebrate genes, termed here hedgehog-related genes, comprise the signals produced by these embryonic patterning centers. As described herein, each of the disclosed vertebrate hedgehog (hh) homologs exhibits spatially and temporally restricted expression domains indicative of important roles in embryonic patterning. For instance, the results provided below indicate that vertebrate hh genes are expressed in the posterior limb bud, Hensen's node, the early notochord, the floor plate of the neural tube, the fore- and hindgut and their derivatives. These are all important signaling centers known to be required for proper patterning of surrounding embryonic tissues.

The Hedgehog family of vertebrate inter-cellular signaling molecules provided by the present invention consists of at least four members. Three of these members, herein referred to as Desert hedgehog (Dhh), Sonic hedgehog (Shh) and Indian hedgehog (Ihh), exist in all vertebrates, including fish, birds, and mammals. A fourth member, herein referred to as Moonrat hedgehog (Mhh), appears specific to fish.

As described in the following examples, the cDNA clones provided by the present invention were obtained by first screening a mouse genomic library with a partial Drosophila hh cDNA clone (0.7 kb). Positive plaques were identified and one mouse clone was selected. This clone was then used as a probe to obtain a genomic clone containing the full coding sequence of the Mouse Dhh gene. As described in the attached Examples, Northern blots and in situ hybridization demonstrated that Mouse Dhh is expressed in the testes, and potentially the ovaries, and is also associated with sensory neurons of the head and trunk. Interestingly, no expression was detected on the nerve cell bodies themselves (only the axons), indicating that Dhh is likely produced by the shwann cells.

In order to obtain cDNA clones encoding chicken hh genes, degenerate oligonucleotides were designed corresponding to the amino and carboxy ends of Drosophila hh exon 2. As described in the Examples below, these oligonucleotides were used to isolate PCR fragments from chicken genomic DNA. These fragments were then cloned and sequenced. Ten clones yielded two different hh homologs, chicken Dhh and chicken Shh. The chicken Shh clone was then used to screen a stage 21/22 limb bud cDNA library which yielded a full length Shh clone.

In order to identify other vertebrate hedgehog homologs, the chicken clones (Dhh and Ihh) were used to probe a genomic southern blot containing chicken DNA. As described below, genomic DNA was cut with various enzymes which do not cleave within the probe sequences. The DNA was run on a gel and transferred to a nylon filter. Probes were derived by ligating each 220 bp clone into a concatomer and then labeling with a random primer kit. The blots were hybridized and washed at low stringency (hybridization: 1% BSA, 1 mM EDTA, 0.5 m NaHPO$_4$, 7% SDS; Wash: 0.5% BSA, 1 mM EDTA, 5% SDS, 40 mM NaHPO$_4$). In each case, three hybridizing bands were observed following autoradiography, one of which was significantly more intense (a different band with each probe), indicating that there are at least three vertebrate hh genes. Additional cDNA and genomic screens carried out have yielded clones of three hh homologs from chickens and mice (Shh, Dhh and Ihh), and four hh homologs from zebrafish (Shh, Dhh, Ihh and Mhh). Weaker hybridization signals suggested that the gene family may be even larger. Moreover, a number of weakly hybridizing genomic clones have been isolated, but have not yet been analyzed. Subsequently, the same probes derived from chicken hedgehog homologs have been utilized to screen a human genomic library. PCR fragments derived from the human genomic library were then sequenced, and PCR probes derived from the human sequences were used to screen human fetal cDNA libraries. Presumed full-length cDNAs encoding human hedgehog proteins were isolated from the fetal library, and represent a source of recombinant human hedgehog proteins.

In order to determine the expression patterns of the various vertebrate hh homologs, in situ hybridizations were performed in developing embryos of chicken, mice and fish. As described in the Examples below, the resulting expression patterns of each hh homolog were similar across each species and revealed that hh genes are expressed in a number of important embryonic signaling centers. For example, Shh is expressed in Hensen's node, the notochord, the ventral floorplate of the developing neural tube, and the ZPA at the base of the limb buds; Ihh is expressed in the embryonic yolksac and hindgut, and appear also to be involved in chondrogenesis; Dhh is expressed in the testes; and Mhh (only in zebrafish) is expressed in the notochord and in certain cranial nerves.

Accordingly, one aspect of this invention pertains to isolated nucleic acids comprising nucleotide sequences encoding vertebrate hh homologs, fragments thereof encoding polypeptides having at least one biological activity of a vertebrate hh homolog, and/or equivalents of such nucleic acids. The term nucleic acid as used herein is intended to include such fragments and equivalents. The term equivalent is understanding to include nucleotide sequences encoding functionally equivalent vertebrate hh proteins or functionally equivalent peptides having an activity of a vertebrate hh protein such as described herein. Equivalent nucleotide sequences will include sequences that differ by one or more nucleotide substitutions, additions or deletions, such as allelic variants; and will also include sequences that differ from the nucleotide sequences encoding the presently claimed vertebrate hh homologs shown in SEQ ID NO: 1, SEQ ID NO: 3, SEQ ID NO: 5, SEQ ID NO: 7 and SEQ ID NO: 9 due to the degeneracy of the genetic code. Equivalents will also include nucleotide sequences that hybridize under stringent conditions (i.e., equivalent to about 20°–27° C. below the melting temperature (Tm) of the DNA duplex formed in about 1M salt) to the nucleotide sequences of the presently claimed vertebrate hh homologs shown in SEQ ID NO: 1, SEQ ID NO: 3, SEQ ID NO: 5, SEQ ID NO: 7 and SEQ ID NO: 9. In one embodiment, equivalents will further include nucleic acid sequences derived from and evolutionarily related to the nucleotide sequences shown in SEQ ID No. 1, SEQ ID No. 3; SEQ ID No. 7 and SEQ ID No. 9.

Polypeptides referred to herein as having an activity of a vertebrate hh protein are defined as peptides that have an amino acid sequence corresponding to all or a portion of the amino acid sequences of the vertebrate hh proteins shown in SEQ ID NO: 2, SEQ ID NO: 4, SEQ ID NO: 6, SEQ ID NO: 8 and SEQ ID NO: 10 and which have at least one biological activity of a vertebrate hh protein. Examples of such biological activity of a vertebrate hh protein include the ability to induce formation and differentiation of the head, limbs, lungs, central nervous system (CNS), or mesodermal patterning of developing vertebrate embryos. In preferred embodiments, the biological activity can comprise an ability to regulate neurogenesis, such as a motor neuron inducing activity, a neuronal differentiation inducing activity, or a neuronal survival promoting activity. Hedgehog proteins of the present invention can also have bioligical activities which include an ability to regulate organogensis, such as through the ability to influence limb patterning, by, for example, a skeletal homeotic activity. The biological activity associated with the hedgehog proteins of the present invention can also include the ability to induce stem cell or germ cell differentiation, including the ability to induce differentiation of chondrocytes or an involvement in spermatogenesis. Other bioligical activities of the subject hedgehog proteins are described herein or will be reasonably apparent to those skilled in the art. It will be generally appreciated that it can be advantageous to provide hedgehog agonists and antagonists which either promote or inhibit only a subset of the biological activities of naturally occuring vertebrate hedgehog proteins, in order that, for example, specific effects can be elicited by treatment with fewer potential side effects relative to agonists or antagonists directed to all hedgehog-related biological activities.

The term "evolutionarily related to", with respect to nucleic acid sequences encoding hedgehog homologs, refers to nucleic acid sequences which have arisen naturally in vertebrate organism. The term also refers to nucleic acid sequences which, while derived from a naturally occurring vertebrate hedgehog, have been altered by mutagenesis, as for example, combinatorial mutagenesis described below, yet still encode polypeptides which have at least one activity of a vertebrate hedgehog protein.

In one embodiment, the nucleic acid is a cDNA encoding a peptide having at least one activity of a vertebrate hh protein. Preferably, the nucleic acid is a cDNA molecule comprising at least a portion of the nucleotide sequence encoding a vertebrate hh protein selected from the group consisting of SEQ ID NO: 1, SEQ ID NO: 3, SEQ ID NO: 5, SEQ ID NO: 7 and SEQ ID NO: 9. A preferred portion of the cDNA molecules shown in SEQ ID NO: 1, SEQ ID NO: 3, SEQ ID NO: 5, SEQ ID NO: 7 and SEQ ID NO: 9 includes the coding region of the molecule.

In another embodiment, the nucleic acid of the invention encodes a peptide having an activity of a vertebrate hh protein and comprising an amino acid sequence selected from the group consisting of SEQ ID NO: 2, SEQ ID NO: 4, SEQ ID NO: 6, SEQ ID NO: 8 and SEQ ID NO: 10. Preferred nucleic acids encode a peptide having a vertebrate hh protein activity and being at least 52% homologous, more preferably in the range of 60–70% homologous and most preferably in the range of 80–90% homologous with an amino acid sequence selected from the group consisting of SEQ ID NO: 2, SEQ ID NO: 4, SEQ ID NO: 6, SEQ ID NO: 8 and SEQ ID NO: 10. Nucleic acids which encode peptides having an activity of a vertebrate hh protein and having at least about 90%, more preferably at least about 95%, and most preferably at least about 98–99% homology with a sequence selected from the group consisting of SEQ ID NO: 2, SEQ ID NO: 4, SEQ ID NO: 6, SEQ ID NO: 8 and SEQ ID NO: 10 are also within the scope of the invention. Homology refers to sequence similarity between two peptides having an activity of a vertebrate hh protein or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence selected from the group consisting of SEQ ID NO: 2, SEQ ID NO: 4, SEQ ID NO: 6, SEQ ID NO: 8 and SEQ ID NO: 10. Appropriate stringency conditions which promote DNA hybridization, for example, 6.0×sodium chloride/sodium citrate (SSC) at about 45° C., followed by a wash of 2.0×SSC at 50°, are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding peptides having an activity of a vertebrate hh protein, as described herein, and having a sequence which differs from the nucleotide sequences shown SEQ ID NO: 1, SEQ ID NO: 3, SEQ ID NO: 5, SEQ ID NO: 7 and SEQ ID NO: 9 due to degeneracy in the genetic code are also within the scope of the invention. Such nucleic acids encode functionally equivalent peptides (i.e., a peptide having an activity of a vertebrate hh protein) but differ in sequence from the sequences shown in SEQ ID NO: 1, SEQ ID NO: 3, SEQ ID NO: 5, SEQ ID NO: 7 and SEQ ID NO: 9 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the vertebrate hh protein. However, it is expected that DNA sequence polymorphisms that do lead to changes in the amino acid sequences of vertebrate hh proteins will exist among vertebrates. One skilled in the art will appreciate that these variations in one or more nucleotides (up to about 3–4% of the nucleotides) of the nucleic acids encoding peptides having an activity of a vertebrate hh protein may exist among individual vertebrates due to natural allelic variation. Any and all such nucleotide variations and resulting amino acid polymorphisms are within the scope of this invention.

Fragments of the nucleic acid encoding the active portion of the presently claimed vertebrate hh proteins are also within the scope of the invention. As used herein, a fragment of the nucleic acid encoding the active portion of a vertebrate hh protein refers to a nucleotide sequence having fewer nucleotides than the nucleotide sequence encoding the entire amino acid sequence of a vertebrate hh protein and which encodes a peptide having an activity of a vertebrate hh protein (i.e., a peptide having at least one biological activity of a vertebrate hh protein) as defined herein. Nucleic acid fragments within the scope of the invention include those capable of hybridizing under high or low stringency conditions with nucleic acids from other vertebrates for use in screening protocols to detect other vertebrate hh homologs. Generally, the nucleic acid encoding a peptide having an activity of a vertebrate hh protein will be selected from the bases encoding the mature protein. However, in some instances it may be desirable to select all or part of a peptide from the leader sequence portion of the nucleic acids of the invention. Nucleic acids within the scope of the invention may also contain linker sequences, modified restriction endonuclease sites and other sequences useful for molecular cloning, expression or purification of recombinant peptides having at least one biological activity of a vertebrate hh protein.

As described in the following Examples, a nucleic acid encoding a peptide having an activity of a vertebrate hh protein may be obtained from mRNA present in any of a number of signalling centers of developing vertebrate embryos, such as the notochord, the bottom floorplate of the neural tube, and the zone of polarizing activity (ZPA). It should also be possible to obtain nucleic acids encoding vertebrate hh proteins from genomic DNA obtained from both vertebrate adults and embryos. For example, a gene encoding a vertebrate hh protein can be cloned from either a cDNA or a genomic library in accordance with protocols herein described, as well as those generally known to those skilled in the art. A cDNA encoding a vertebrate hh protein can be obtained by isolating total mRNA from a developing vertebrate embryo. Double stranded cDNAs can then be prepared from the total mRNA, and subsequently inserted into a suitable plasmid or bacteriophage vector using any one of a number of known techniques. Genes encoding vertebrate hh proteins can also be cloned using established polymerase chain reaction techniques in accordance with the nucleotide sequence information provided by the invention. The nucleic acids of the invention can be DNA or RNA. A preferred nucleic acid is a cDNA encoding a vertebrate hh protein having a sequence selected from the group consisting of SEQ ID NO: 1, SEQ ID NO: 3, SEQ ID NO: 5, SEQ ID NO: 7 and SEQ ID NO: 9.

This invention also provides expression vectors containing a nucleic acid encoding a peptide having an activity of a vertebrate hh protein, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of a vertebrate hh protein. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a DNA encoding a peptide having an activity of a vertebrate hh protein. Such expression vectors can be used to transfect cells to thereby produce proteins or peptides, including fusion proteins or peptides encoded by nucleic acids as described herein.

This invention also pertains to a host cell transfected to express a polypeptide having an activity of a vertebrate hh protein. The host cell may be any prokaryotic or eukaryotic cell. For example, a peptide having an activity of a vertebrate hh protein may be expressed in bacterial cells such as *E. coli*, insect cells (baculovirus), yeast, or mammalian cells such as Chinese hamster ovary cells (CHO). Other suitable host cells are known to those skilled in the art.

Another aspect of the present invention concerns recombinant hedgehog proteins which are encoded by genes derived from vertebrate organisms, and which have at least one biological activity of a vertebrate hedgehog protein. The term "recombinant protein" refers to a protein of the present invention which is produced by recombinant DNA techniques, wherein generally DNA encoding the hedgehog protein is inserted into a suitable expression vector which is in turn used to transform a host cell to produce the heterologous protein. Moreover, the phrase "derived from", with respect to a recombinant gene encoding the recombinant hedgehog, is meant to include within the meaning of "recombinant protein" those proteins having an amino acid sequence of a native vertebrate hedgehog, or an amino acid sequence similar thereto which is generated by mutations including substitutions and deletions of a naturally occuring hedgehog protein of a vertebrate organism. Recombinant proteins preferred by the present invention, in addition to native vertebrate hedgehog proteins, are at least 52% homologous, more preferably in the range of 60%–70% homologous and most preferably in the range of 80%–90% homologous with an amino acid sequence selected from the group consisting of SEQ ID NO: 2, SEQ ID NO: 4, SEQ ID NO: 6, SEQ ID NO: 8 and SEQ ID NO: 10. Polypeptides having an activity of a vertebrate hh protein and having at least about 90%, more preferably at least about 95%, and most preferably at least about 98–99% homology with a sequence selected from the group consisting of SEQ ID NO: 2, SEQ ID NO: 4, SEQ ID NO: 6, SEQ ID NO: 8 and SEQ ID NO: 10 are also within the scope of the invention.

In particular, recombinant hedgehog protein, as used herein, includes a protein of the same or similar sequence as a native vertebrate hedgehog protein, but lacking amino acid sequences at either or both of its N-terminal and C-terminal ends. Examples of such proteins include, but are not limited to, vertebrate hedgehog proteins which lack a putative signal peptide, such as residues 1–26 of SEQ ID No. 2, 1–21 of SEQ ID No. 4, 1–24 of SEQ ID No. 8 and 1–23 of SEQ ID No. 10. In other exemplary embodiments, the recombinant proteins are truncation mutants which correspond to the amino terminal half of a "mature" vertebrate hedgehog protein. In preferred embodiments, the truncation mutants comprise at least 50–60 amino acid residues, more preferably 90–100 amino acid residues, and most preferably at least 150 amino acid residues of a vertebrate hedgehog protein, or variant thereof, while retaining at least one activity of a vertebrate hh protein. Such truncated hedgehog analogs are preferably at least 63% homologous, more preferably at least 70% homologous and most preferably in the range of 80%–90% homologous with an amino acid sequence selected from the group consisting of SEQ ID NO: 2, SEQ ID NO: 4, SEQ ID NO: 6, SEQ ID NO: 8 and SEQ ID NO: 10. Polypeptides having an activity of a vertebrate hh protein and having at least about 90%, more preferably at least about 95%, and most preferably at least about 98–99% homology with a sequence selected from the group consisting of SEQ ID NO: 2, SEQ ID NO: 4, SEQ ID NO: 6, SEQ ID NO: 8 and SEQ ID NO: 10 are also within the scope of the invention.

The present invention further pertains to recombinant hedgehog proteins which are encoded by genes derived from a vertebrate organism and which have amino acid sequences evolutionarily related to a vertebrate hedgehog protein. Such recombinant hedgehog proteins preferably are capable of functioning in one of either role of an agonist of antagonist of at least one biological activity of a vertebrate hedgehog. The term "evolutionarily related to", with respect to amino acid sequences of the present recombinant hedgehog proteins, refers to vertebrate hedgehog protein, having amino acid sequences which have arisen naturally, as well as mutational variants of vertebrate hedgehog proteins which are derived, for example, by combinatorial mutagenesis. Recombinant proteins evolutionarily related to vertebrate hedgehog proteins preferred by the present invention are at least 52% homologous, more preferably in the range of 60%–70% homologous and most preferably in the range of 80%–90% homologous with an amino acid sequence selected from the group consisting of SEQ ID NO: 2, SEQ ID NO: 4, SEQ ID NO: 6, SEQ ID NO: 8 and SEQ ID NO: 10. Polypeptides having an activity of a vertebrate hh protein and having at least about 90%, more preferably at least about 95%, and most preferably at least about 98–99% homology with a sequence selected from the group consisting of SEQ ID NO: 2, SEQ ID NO: 4, SEQ ID NO: 6, SEQ ID NO: 8 and SEQ ID NO: 10 are also within the scope of the invention.

The present invention further pertains to methods of producing peptides that have an activity of a vertebrate hh protein. For example, a host cell transfected with a nucleic acid vector directing expression of a nucleotide sequence encoding a peptide having an activity of a vertebrate hh protein can be cultured under appropriate conditions to allow expression of the peptide to occur. The peptide may be secreted and isolated from a mixture of cells and medium containing the peptide having an activity of a vertebrate hh protein. Alternatively, the peptide may be retained cytoplasmically and the cells harvested, lysed and the protein isolated. A cell culture includes host cells, media and other byproducts. Suitable media for cell culture are well known in the art. The peptide having an activity of a vertebrate hh protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for a peptide having an activity of a vertebrate hh protein.

Thus, a nucleotide sequence derived from the cloning of the vertebrate hedgehog homologs of the present invention, encoding all or a selected portion of the protein, can be used to produce a recombinant form of hh via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant hedgehog proteins, or portions thereof, by microbial means or tissue-culture technology in accord with the subject invention. Depending on the expression system chosen, the ability to obtain a recombinant protein which is either glycosylated or not can be controlled The recombinant hh protein can be produced by ligating the cloned gene, or a portion thereof, into a vector suitable for expression in either prokaryotic cells, eukaryotic cells, or both. Expression vehicles for production of recombinant hh include plasmids and other vectors. For instance, suitable vectors for the expression of hh include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 nd 17. In some instances, it may be desirable to express the recombinant hh by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of hh is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169: 751–757) and *Salmonella typhimurium* and its in vitro activity has been demonstrated on recombinant proteins (Miller et al. (1987) *PNAS* 84: 2718–1722). Therefore, removal of an N-terminal methionine, if desired, can be achieved either in vivo by expressing hedgehog-derived polypeptides in a host which produces MAP (e.g., *E. coli* or CM89 or *S. Cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a hedgehog protein. For example, the VP6 capsid protein of rotavirus can be used as an immunologic carrier protein for portions of the hh polypeptide, either in the monomeric form or in the form of a viral particle. The nucleic acid sequences corresponding to the portion of the hedgehog protein to which antibodies are to be raised can be incorporated into a fusion gene construct which includes coding sequences for a late vaccinia virus structural protein to produce a set of recombinant viruses expressing fusion proteins comprising a portion of the protein hh as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an hh protein and the poliovirus capsid protein can be created to enhance immunogenecity of the set of polypeptide antigens (see, for example, EP Publication No. 0259149; and Evans et al. (1989) *Nature* 339: 385; Huang et al. (1988) *J Virol.* 62: 3855; and Schlienger et al. (1992) *J Virol.* 66: 2).

The Multiple Antigen Peptide system for peptide-based immunization can be utilized, wherein a desired portion of an hh protein is obtained directly from organo-chemical synthesis of the peptide onto an oligomeric branching lysine core (see, for example, Posnett et al. (1988) *JBC* 263: 1719 and Nardelli et al. (1992) *J Immunol.* 148: 914). Antigenic determinants of the hh proteins can also be expressed and presented by bacterial cells.

In addition to utilizing fusion proteins to enhance immunogenicity, it is widely appreciated that fusion proteins can also facilitate the expression of proteins, such as the hedgehog of the present invention. For example, the hedgehog protein can be generated as a glutathione-S-transferase (GST-fusion protein). Such GST fusion proteins can enable easy purification of the hedgehog protein, such as by the use of glutathione-derivateized matrices (see, for example, *Current Protocols in Molecular Biology*, eds. Ausabel et al. (N.Y.: John Wiley & Sons, 1991)). In another embodiment, a fusion gene coding for a purification leader sequence, such as a poly-(His)/enterokinase cleavage site sequence at the N-terminus of the desired portion of the hh protein, can allow purification of the expressed hh-fusion protein by affinity chromatography using a $Ni^{2+}$ metal resin. The purification leader sequence can then be subsequently removed by treatment with enterokinase (e.g., see Hochuli et al. 1987 *J Chromatography* 411: 177; and Janknecht et al. *PNAS* 88: 8972).

In further embodiments, the recombinant hedgehog protein can be a chimeric protein comprising a moiety, other than sequences naturally associated with the hh protein, that binds a component of the extracellular matrix. Such a chimeric hedgehog protein can be useful in circumstances wherein diffusion of the hh from a treatment site is undesirable, and will function to such an end by virtue of localizing the chimeric hh at or proximate a treatment site. An hh of this embodiment can be generated as the product of a fusion gene, or by chemical cross-linking.

A number of proteins have been characterized from the extracellular matrix (ECM) of tissues that will support the localization of a chimeric hh protein at a target site. One example of a well characterized protein is fibronectin. Fibronectin is a large adhesive glycoprotein with multiple functional domains. Several of these domains have matrix attachment activity. For example, one of these is a single "type-III repeat" which contains a tetrapeptide sequence R-G-D-S (Pierschbacher et al. (1984) *Nature* 309: 30–3; and Kornblihtt et al. (1985) *EMBO* 4: 1755–9). Peptides as small as pentapeptides containing these amino acids are able to support attachment to a cell through binding ECM components (Ruoslahti et al. (1987) *Science* 238: 491–497; Pierschbacher et al. (1987) *J Biol. Chem.* 262: 17294–8.; Hynes (1987) *Cell* 48: 549–54; and Hynes (1992) *Cell* 69: 11–25). In fact, commercialized products based on this cell attachment sequence for use as reagents in cell culture and various biomaterials applications are now available. See, for example, recent catalogs from Telios Pharmaceutical, BRL, Stratagene, Protein Polymer Technologies as well as U.S. Pat. Nos. 4,517,686; 4,589,881; 4,578,079; 4,614,517; 4,661,111; and 4,792,525.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, Eds. Ausubel et al. John Wiley & Sons: 1992).

It may be necessary in some instances to introduce an unstructured polypeptide linker region between the portion of the fusion protein corresponding to the hedgehog polypeptide and other fragments. This linker can facilitate enhanced flexibility of the fusion protein allowing the hedgehog-derived portion to interact freely with a surface component of, for example, an hh receptor, reduce steric hindrance between the two fragments, as well as allow appropriate folding of each fragment to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) *PNAS* 85: 4879; and U.S. Pat. No. 5,091,513. Naturally occurring unstructured linkers of human origin are preferred as they reduce the risk of immunogenicity.

Another aspect of the invention pertains to isolated peptides having an activity of a vertebrate hh protein. A peptide having an activity of a vertebrate hh protein has at least one biological activity of a vertebrate hh protein. Examples of such biological activity of a vertebrate hh protein include the ability to induce formation and differentiation of the head, limbs, lungs, central nervous system (CNS), or mesodermal patterning of developing vertebrate embryos. In preferred embodiments, the biological activity can comprise an ability to regulate neurogenesis, such as a motor neuron inducing activity, a neuronal differentiation inducing activity, or a neuronal survival promoting activity. Hedgehog proteins of the present invention can also have bioligical activities which include an ability to regulate organogensis, such as through the ability to influence limb patterning, by, for example, a skeletal homeotic activity. The biological activity associated with the hedgehog proteins of the present invention can also include the ability to induce stem cell or germ cell differentiation, including the ability to induce differentiation of chondrocytes or an involvement in spermatogenesis. Other bioligical activities of the subject hedgehog proteins are described herein or will be reasonably apparent to those skilled in the art. A peptide having an activity of a vertebrate hh protein may differ in amino acid sequence from the sequences shown in SEQ ID NO: 2, SEQ ID NO: 4, SEQ ID NO: 6, SEQ ID NO: 8 and SEQ ID NO: 10 but such differences result in a modified protein which functions in the same or similar manner as a native vertebrate hh protein or which has the same or similar characteristics of a native vertebrate hh protein. Various modifications of the vertebrate hh protein to produce these and other functionally equivalent peptides are described in detail herein. The term peptide, as used herein, refers to peptides, proteins, and polypeptides.

The present invention also makes available isolated hedgehog protein which is isolated from, or otherwise substantially free of other extracellular proteins, especially morphogenic proteins, normally associated with the vertebrate hedgehog protein. The term "substantially free of other extracellular proteins" (also referred to herein as "contaminating proteins") is defined as encompassing vertebrate hedgehog preparations comprising less than 20% (by dry weight) contaminating protein, and preferably comprises less than 5% contaminating protein. Functional forms of hedgehog can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins (particularly other trophic or morphogenic factors, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins) substances or solutions. The term "isolated" as also used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid is meant to include nucleic acid fragments which are not naturally occurring as fragments and would not be found in the natural state.

Isolated peptides having the activity of a vertebrate hh protein can also be obtained by screening peptides recombinantly produced from the corresponding fragment of the nucleic acid of vertebrate hh encoding such peptides. In addition, fragments can be chemically synthesized using techniques known in the art such as conventional Merrifield solid phase f-Moc or t-Boc chemistry. For example, the vertebrate hh protein may be arbitrarily divided into fragments of desired length with no overlap of the fragments, or preferably divided into overlapping fragments of a desired length. The fragments can be produced (recombinantly or by chemical synthesis) and tested to identify those peptides having a vertebrate hh protein activity.

It is possible to modify the structure of a peptide having an activity of a vertebrate hh protein for such purposes as increasing solubility, enhancing therapeutic or prophylactic efficacy, or stability (e.g., shelf life ex vivo and resistance to proteolytic degradation in vivo). Such modified peptides are considered functional equivalents of peptides having an activity of a vertebrate hh protein as defined herein. A modified peptide can be produced in which the amino acid sequence has been altered, such as by amino acid substitution, deletion, or addition.

Moreover, as described above, variations of the hh peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations)

will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide= asparagine, glutamine; and (6) sulfur-containing=cysteine and methoinine. (see, for example, *Biochemistry*, 2nd ed, Ed. by L. Stryer, WH Freeman and Co.: 1981). Whether a change in the amino acid sequence of a peptide results in a functional hh homolog can be readily determined by assessing the ability of the variant peptide to produce a response in cells in a fashion similar to the wild-type hh. Peptides in which more than one replacement has taken place can readily be tested in the same manner.

This invention further contemplates a method of generating sets of combinatorial mutants of hh, as well as truncation mutants, and is especially useful for identifying potential variant sequences (e.g. homologs) that are functional in binding to a receptor for hh. The purpose of screening such combinatorial libraries is to generate, for example, novel hh homologs which can act as either agonists or antagonist, or alternatively, possess novel activities all together. To illustrate, hedgehog homologs can be engineered by the present method to provide more efficient binding to an hh receptor, yet still retain at least a portion of an activity associated with hh. Thus, combinatorially-derived homologs can be generated to have an increased potency relative to a naturally occurring hh. Likewise, hh homologs can be generated by the present combinatorial approach to act as antagonists, in that they are able to bind an hh receptor yet not induce any biological response, thereby blocking the action of hh or an hh agonist. Moreover, manipulation of certain domains of hh by the present method can provide domains more suitable for use in fusion proteins, such as one that incorporates portions of other proteins which are derived from the extracellular matrix and/or which bind extracellular matrix components.

In one aspect of this method, the amino acid sequences for a population of vertebrate hedgehog homologs or other related proteins are aligned, preferably to promote the highest homology possible. Such a population of variants can include, for example, hh homologs from one or more species. Amino acids which appear at each position of the aligned sequences are selected to create a degenerate set of combinatorial sequences.

In a preferred embodiment, the combinatorial hh library is produced by way of a degenerate library of genes encoding a library of polypeptides which each include at least a portion of potential hh sequences. A mixture of synthetic oligonucleotides can be enzymatically ligated into gene sequences such that the degenerate set of potential hh sequences are expressible as individual polypeptides, or alternatively, as a set of larger fusion proteins (e.g. for phage display) containing the set of hh sequences therein.

As illustrated in FIG. 7, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned. For instance, FIG. 7 includes the alignment of several cloned forms of hh from different species. Analysis of the alignment of the hh clones shown in FIG. 7 can give rise to the generation of a degenerate library of polypeptides comprising potential hh sequences. In a preferred embodiment, the variegated library of hedgehog variants is generated by combinatorial mutagenesis at the nucleic acid level, and is encoded by a variegated gene library.

There are many ways by which the library of potential hh homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential hh sequences. The synthesis of degenerate oligonucleotides is well known in the art (see for example, Narang, SA (1983) *Tetrahedron* 39: 3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53: 323; Itakura et al. (1984) *Science* 198: 1056; Ike et al. (1983) *Nucleic Acid Res.* 11: 477. Such techniques have been employed in the directed evolution of other proteins (see, for example, Scott et al. (1990) *Science* 249: 386–390; Roberts et al. (1992) *PNAS* 89: 2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hh sequences created by combinatorial mutagenesis techniques.

In one embodiment, the combinatorial library is designed to be secreted (e.g. the polypeptides of the library all include a signal sequence but no transmembrane or cytoplasmic domains), and is used transfect a eukaryotic cell that can be co-cultured with embryonic cells. A functional hh secreted by the cells expressing the combinatorial library will diffuse to neighboring embryonic cells and induce a particular biological response, such as to illustrate, neuronal differentiation. Using antibodies directed to epitopes of neuronal cells (e.g. NCAM), the pattern of detection of neuronal induction will resemble a gradient function, and will allow the isolation (generally after several repetitive rounds of selection) of cells producing active hh homologs. Likewise, hh antagonists can be selected in similar fashion by the ability of the cell producing a functional antagonist to protect neighboring cells from the effect of wild-type hh added to the culture media.

To illustrate, target cells are cultured in 24-well microtitre plates. Other eukaryotic cells are transfected with the combinatorial hh gene library and cultured in cell culture inserts (e.g. Collaborative Biomedical Products, Catalog #40446) that are able to fit into the wells of the microtitre plate. The cell culture inserts are placed in the wells such that recombinant hh homologs secreted by the cells in the insert can diffuse through the porous bottom of the insert and contact the target cells in the microtitre plate wells. After a period of time sufficient for functional forms of hh to produce a measurable response in the target cells, the inserts are removed and the effect of hh on the target cells determined. For example, where the target cell is a neural crest cell and the activity desired from the hh homolog is the induction of neuronal differentiation, then fluorescently-labeled antibodies specific for NCAM or other neuronal markers can be used to score for induction in the target cells as indicative of a functional hh in that well. Cells from the inserts corresponding to wells which score positive for activity can be split and re-cultured on several inserts, the process being repeated until the active clones are identified.

In yet another screening assay, the candidate hh gene products are displayed on the surface of a cell or viral particle, and the ability of particular cells or viral particles to bind an hedgehog-binding protein (such as an hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) Bio/Technology 9: 1370–1371; and Goward et al. (1992) TIBS 18: 136–140). In a similar fashion, fluorescently labeled molecules which bind hh can be used to score for potentially functional hh homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267: 16007–16010; Griffths et al. (1993) EMBO J 12: 725–734; Clackson et al. (1991) Nature 352: 624–628; and Barbas et al. (1992) PNAS 89: 4457–4461).

In an illustrative embodiment, the recombinant phage antibody system (RPAS, Pharamacia Catalog number 27-9400-01) can be easily modified for use in expressing and screening hh combinatorial libraries. For instance, the pCANTAB 5 phagemid of the RPAS kit contains the gene which encodes the phage gIII coat protein. The hh combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate hh gene insert. The resulting recombinant phage contain phagemid DNA encoding a specific candidate hh, and display one or more copies of the corresponding fusion coat protein. The phage-displayed candidate hhs which are capable of binding an hh receptor are selected or enriched by panning. For instance, the phage library can be applied to cultured embryonic cells and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for hh homologs, which can then be screened for further biological activities in order to differentiate agonists and antagonists.

Another aspect of the invention pertains to an antibody specifically reactive with a peptide having an activity of a vertebrate hh protein. For example, by using peptides having an activity of a vertebrate hh protein based on the cDNA sequence of a vertebrate hh protein, anti-protein/anti-peptide antisera or monoclonal antibodies can be made using standard methods. A mammal such as a mouse, a hamster or rabbit can be immunized with an immunogenic form of the peptide (e.g., vertebrate hh protein or an antigenic fragment which is capable of eliciting an antibody response). Techniques for conferring immunogenicity on a protein or peptide include conjugation to carriers or other techniques well known in the art. A peptide having an activity of a vertebrate hh protein can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, anti-hh antisera can be obtained and, if desired, polyclonal anti-hh antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), as the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a vertebrate hedgehog protein and the monoclonal antibodies isolated.

The term antibody as used herein is intended to include fragments thereof which are also specifically reactive a vertebrate hh protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-hh portion.

Both monoclonal and polyclonal antibodies (Ab) directed against vertebrate hedgehog variants, and antibody fragments such as Fab' and F(ab')$_2$, can be used to block the action of hh and allow the study of the formation of tissue-patterning, such as that which develops in the absence, or controlled presence, of hedgehog. For instance, purified monoclonal Abs can be injected directly into the limb buds of chick embryos at various stages of development. The use of anti-hh Abs during this developmental stage can allow assessment of the effect of hh on the formation of, for example, motor neuron innervation and skeletal patterning in vivo. In a similar approach, hybridomas producing anti-hh monoclonal Abs, or biodegradable gels in which anti-hh Abs are suspended, can be implanted at a site proximal or within the area at which hh action is intended to be blocked. Experiments of this nature can aid in deciphering the role of other factors that may be involved in limb pattern formation. Moreover, the ability to alter hh gradients in the limb, as well as influence the timing and/or exposure duration of the limb to hh, can be instrumental in further deciphering the various roles of hedgehog in development.

Antibodies which specifically bind hh epitopes can also be used in immunohistochemical staining of tissue samples in order to evaluate the abundance and pattern of expression of hh homologs. Anti-hh antibodies can be used diagnostically in immuno-precipitation and immuno-blotting to detect and evaluate hh levels in tissue or bodily fluid as part of a clinical testing procedure. For instance, such measurements can be useful in predictive valuations of the onset or progression of neurological disorders, such as those marked by denervation-like or disuse-like symptoms. Likewise, the ability to monitor hh levels in an individual can allow determination of the efficacy of a given treatment regimen for an individual afflicted with such a disorder. The level of hh can be measured in bodily fluid, such as in samples of cerebral spinal fluid, or can be measured in tissue, such as produced by biopsy. Diagnostic assays using anti-hh antibodies can include, for example, immunoassays designed to aid in early diagnosis of a neurodegenerative disorder, particularly one which is manifest at birth.

Another application of anti-hh antibodies is in the immunological screening of cDNA libraries constructed in expression vectors such as λgt11, λgt18-23, λZAP, and λOR8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of hh homologs can then be detected with antibodies, as, for example, reacting nitrocellulose filters lifted from infected plates with anti-hh antibodies. Phage, scored by this assay, can then be isolated from the infected plate. Thus, the presence of other vertebrate hh homologs can be detected and cloned from other sources.

The nucleotide sequence determined from the cloning of hh from any one of mouse, chicken, or zebrafish will further allow for the generation of probes designed for use in identifying hh homologs in other animals, especially humans. For instance, as described in the attached Example 4, such probes can be used, in known methods, to screen both messenger and genomic DNA libraries for the presence of homologous sequences ostensibly arising from a hedgehog-like gene encoding a hedgehog homolog. Indeed, as described below, such techniques have been employed to clone human homologs of vertebrate hedgehogs.

In addition, nucleotide probes can be generated, as described in the Examples below, from the cloned sequences of the hedgehog homologs, which allow for histological screening of intact tissue and tissue samples for the presence of hh MRNA. Similar to the diagnostic uses of anti-hh antibodies, the use of probes directed to hh mRNA, or to genomic hh sequences, can be used for both predictive and therapeutic evaluation of allelic mutations which might be manifest in, for example, birth defects. Used in conjunction with anti-hh antibody immunoassays, the nucleotide probes can help facilitate the determination of the molecular basis for a developmental disorder which may involve some abnormality associated with expression (or lack thereof) of a hedgehog protein. For instance, variation in hh synthesis can be differentiated from a change in hh metabolism (such as increased catabolism).

Also, similar to the antibody blocking experiments, the use of anti-sense techniques (e.g. microinjection of antisense molecules, or transfection with plasmids whose transcripts are anti-sense with regard to hh mRNA) can be used to investigate developmental pattern formation, such as in limb generation or neurogenesis, in a controlled hh environment, by inhibiting endogenous hh production. Such techniques can be utilized in cell culture, but can also be used in the creation of transgenic animals.

The present invention, by making available purified and recombinant hedgehog homologs, will allow the development of assays which can be used to screen for drugs which are either agonists or antagonists. By mutagenesis, and other structural surveys of the hedgehog protein family, rationale drug design can be employed to manipulate hh or portions thereof, as either agonists or antagonists, as well as facilitate design of small molecule agonists and antagonists.

In another aspect, the invention features transgenic embryos which ectopically express an hh gene taken from another species. For example, a mouse embryo can be transfected with a DNA construct containing a chicken Shh gene. Such transgenic manipulations are useful to study the conservation in function of various hh homologs across species. In similar fashion, transgenic animals can be generated which express and seceret recombinant hedgehog proteins into their milk. For instance, a recombinant gene encoding a hedgehog protein can be placed under control of a milk casein or whey acid protein promoter and the resulting express construct transgenically incorporated into a mammal capable of lactating. Upon induction of lactation, the recombinant hedgehog protein can be secreted into the milk and collected. In the event that the signal peptide normally associated with the vertebrate hedgehog proteins is not sufficient, it can be readily replaced with, for example, a signal peptide from a milk serum protein. See, for example, the Meade et al. U.S. Pat. No. 4,873,316 and the Gould et al. U.S. Pat. No. 5,215,904.

In another aspect, the invention features an animal model for developmental diseases. i.e., neurodegenerative disease, which has a hh allele which is mis-expressed. For example, a mouse can be bred which has a hh allele deleted of all or part of one or more hh exons. Such a mouse model can then be used to study disorders arising from mis-expressed hh genes.

Another aspect of the present invention relates to a method of inducing and/or maintaining a differentiated state of a cell responsive to a hedgehog protein, by contacting the cells with a hedgehog agonist. For instance, it is contemplated by the invention that, in light of the present finding of a broad involvement of hedgehog proteins in the formation of ordered spatial arrangements of differentiated tissues in vertebrates, the subject method could be used to generate and/or maintain an array of different vertebrate tissue both in vitro and in vivo. The subject method can be practiced with, for example, the goal of inducing neuronal differentiation.

For example, the present method is applicable to cell culture technique. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated, it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with a hedgehog protein in order to induce neuronal differentiation (e.g. of a stem cell), or to maintain the integrity of a culture of terminally-differentiated neuronal cells by preventing loss of differentiation. The source of hh in the culture can be derived from, for example, a purified or semi-purified protein composition added directly to the cell culture media, or alternatively, released from a polymeric device which supports the growth of various neuronal cells and which as been doped with a hedgehog protein. The source of the hh can also be a cell that is co-cultured with the intended neuronal cell and which produces a recombinant hh. Alternatively, the source can be the neuronal cell itself which as been engineered to produce a recombinant hh. In an exemplary embodiment, a naive neuronal cell (e.g. a stem cell) is treated with a hedgehog agonist in order to induce differentiation of the cells into motorneurons. Such motorneurons cultured can be used as convenient assay systems as well as sources of implantable cells for therapeutic treatments.

In one embodiment, the treated cells can be used as a source of tissue for transplantation in vivo. Intracerebral grafting has emerged as an additional approach to central nervous system therapies. For example, one approach to repairing damaged brain tissues involves the transplantation of cells from fetal or neonatal animals into the adult brain (Dunnett et al. (1987) *J. Exp. Biol.* 123: 265–289; and Freund et al. (1985) *J. Neurosci* 5: 603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Thus, use of the present method for maintenance of neuronal cell cultures can provide a source of implantable neuronal tissue. The use of an hedgehog protein, such as Shh or Dhh, in the culture can be used to prevent loss of differentiation, or where fetal tissue is used, especially neuronal stem cells, hh can be used to induce differentiation. Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog protein employed in the present method to culture such stem cells can be to induce differentiation of the uncommitted progenitor and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. The hedgehog protein can be used alone, or can be used in combination with other neurotrophic factors which act to more particularly enhance a particular differentiation fate of the neuronal progenitor cell. In the later instance, the use of hh might be viewed as ensuring that the treated cell has achieved a particular phenotypic state such that the cell is poised along a certain developmental pathway so as to be properly induced upon contact with a secondary neurotrophic factor.

The method of the present invention will also facilitate further determination of a potential role of hedgehog as a "morphogen", that is, a molecule whose tight threshold of concentration determines specific cell fate during development (Wolpert, L. (1969) *J Theor Biol.* 25: 1–47). For instance, in vitro cell cultures can be used for the identification, isolation, and study of genes and gene products that are expressed in response the presence of hedgehog, and therefore likely involved in neurogenesis. These genes would be "downstream" of the hh signal, and required for neuronal differentiation. For example, if new transcription is required for the neuralization, a subtractive cDNA library prepared with control cells and cells treated with an hh can be used to isolate genes that are turned on or turned off by this process. The powerful subtractive library methodology incorporating PCR technology described by Wang and Brown is an example of a methodology useful in conjunction with the present invention to isolate such genes (Wang et al. (1991) *Proc. Natl. Acad. Sci. USA* 88: 11505–11509). For example, this approach has been used successfully to isolate more than sixteen genes involved in tail resorption with and without thyroid hormone treatment in Xenopus. Utilizing control and treated cells, the induced pool can be subtracted from the uninduced pool to isolate genes that are turned on, and then the uninduced pool subtracted from the induced pool for genes that are turned off. From this screen, it is expected that two classes of mRNAs can be identified. Class I RNAs would include those RNAs expressed in untreated cells and reduced or eliminated in induced cells, that is the down-regulated population of RNAs. Class II RNAs include RNAs that are upregulated in response to induction and thus more abundant in treated than in untreated cells. RNA extracted from treated vs untreated cells can be used as a primary test for the classification of the clones isolated from the libraries. Clones of each class can be further characterized by sequencing and, their spatiotemporal distribution determined in the embryo by in situ and developmental northern blots analysis.

For example, in one embodiment of this subtractive assay, special attention can be given to genes that prove to be an immediate early response to neural induction. To qualify as such, these genes should fulfill the following four criteria. First, the RNA should appear quickly following application of hedgehog. To test this requirement, RNA can be isolated at different times from induced cells and scored for gene expression by northern blots. Second, the induction of the gene should not require previous protein synthesis. Thus, cells can be incubated with cycloheximide prior to and during short incubation with a hedgehog protein, after which the cells can be allowed to remain in contact with hh for longer periods of time and then analyzed by northern blotting. This strategy has been used in a similar situation for identifying homeobox genes exhibiting an immediate early response (Rosa, F. M. (1989) Cell. 57: 965–974). Third, where hedgehog is provided as a soluble factor (i.e. diffusible morphagen) immediate early response genes should be expressed as a result of contact with hedgehog and not from a secondary cell-cell induction. One method to differentiate between these two responses is to dissociate the cells in culture add hedgehog and compare the amount of the induced transcript in dissociated cells versus aggregated cells. If the levels are comparable in both types of cultures, then it may be concluded that cell-cell contact was not required for this induction and it is thus likely a direct response of hedgehog treatment. Finally, these genes would be expected to be present and activated in the nervous system during neurogenesis.

Once isolated, the genes regulated by hedgehog induction can be sequenced and their embryonic distribution can be determined by in situ hybridization approaches. If their embryonic expression is in agreement with a possible neurogenic function, they can be tested for neuronal differentiating activity in cell cultures and in embryos as described herein for the hedgehog homologs.

In yet another embodiment, the method of the present invention can be used to isolate and clone hedgehog receptors. For example, purified hedgehog proteins of the present invention can employed to precipitate hedgehog receptor proteins from cell fractions prepared from cells which are responsive to a hedgehog protein. For instance, purified hedgehog protein can be derivatized with biotin (using, for instance, NHS-Biotin, Pierce Chemical catalog no. 21420G), and the biotinylated protein utilized to saturate membrane bound hh receptors. The hedgehog bound receptors can subsequently be adsorbed to immobilized on streptavidin. If desired, the hedgehog-receptor complex can be cross-linked with a chemical cross-linking agent. In such as manner, hh receptors can be purified, preferably to near homogeneity. The isolated hh receptor can then be partially digested with, for example, trypsin, and the resulting peptides separated by reverse-phase chromatography. The chromatographed fragments are then analyzed by Edman degradation to obtain single sequences for two or more of the proteolytic fragments. From the chemically determined amino acid sequence for each of these tryptic fragments, a set of oligonucleotide primers can be designed for PCR. These primers can be used to screen both genomic and cDNA libraries. Similar strategies for cloning receptors have been employed, for example, to obtain the recombinant gene for somatostatin receptors (Eppler et al. (1992) J Biol Chem 267: 15603–15612).

In addition to the implantation of cells cultured in the presence of a functional hedgehog activity and other in vitro uses described above, yet another objective of the present invention concerns the therapeutic application of a hedgehog protein to enhance survival of neurons and other neuronal cells in both the central nervous system and the peripheral nervous system. The ability of hedgehog to regulate neuronal differentiation during development of the nervous system and also presumably in the adult state indicates that hedgehog can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject method to the treatment of prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements. For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum.

In addition to degenerative-induced dementias, a pharmaceutical preparation of a hedgehog homolog can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is ammenable to the treatment of disorders of the cerebellum which result in hypotonia or ataxia, such as those lesions in the cerebellum which produce disorders in the limbs ipsilateral to the lesion. For instance, a preparation of a hedgehog homolog can used to treat a restricted form of cerebellar corical degeneration involving the anterior lobes (vermis and leg areas) such as is common in alcoholic patients.

In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological adnomality is characterized by a selective and progressive degeneration of the lower motor neurons in the spinal cord and the upper motor neurons in the cerebral cortex. The therapeutic application of a hedgehog agonist, particularly Dhh, can be used alone, or in conjunction with other neurotrophic factors such as CNTF, to prevent and/or reverse motor neuron degeneration in ALS patients.

Hedgehog proteins of the present invention can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrythmias which may arise from a degenerative condition of the nerves innervating the striated muscle of the heart.

In another embodiment, the subject method can be used in the treatment of neoplastic or hyperplastic transformations of the central nervous system. Taking advantage of the ability of hedgehog agonists to induce differentiation of neuronal cells can be utilized to cause such transformed cells to become post-mitotic or even apoptotic. Treatment with hedgehog may also involve disruption of autocrine loops, such as TGF-β or PDGF autostimulatory loops, which are believed to be involved in the neoplastic transformation of several neuronal tumors. Hedgehog agonists may thus be of use in the treatment of, for example, malignant gliomas, medulloblastomas, neuroectodermal tumors, and ependymonas.

Yet another aspect of the present invention concerns the application of the discovery that hedgehog proteins are morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog proteins can also be utilized for both cell culture and therapeutic methods involving generation and maintenance non-neuronal tissue.

In one embodiment, the present invention makes use of the discovery that hedgehog proteins, such as Shh, are apparently involved in controlling the development of stem cells responsible for formation of the digestive tract, liver, lungs, and other organs which derive from the primitive gut. For example, hedgehog agonists can be employed in the development and maintenance of an artificial liver which can have multiple metabolic functions of a normal liver. In an exemplary embodiment, hedgehog agonists can be used to induce differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog agonists can be utilized in conjunction with transplantation of such artificial livers, as well as embryonic liver structures, to promote intraperitoneal implantation, vascularization, and in vivo differentiation and maintenance of the engrafted liver tissue.

In yet another embodiment, hedgehog agonists can be employed therapeutically to regulate such organs after physical, chemical or pathological insult. For instance, therapeutic compositions comprising hedgehog agonists can be utilized in liver repair subsequent to a partial hepatectomy. Similarly, therapeutic compositions containing hedgehog agonists can be used to promote regeneration of lung tissue in the treatment of emphysema.

In still another embodiment of the present invention, compositions comprising hedgehog protein agonists can be used in the in vitro generation of skeletal tissue such as from skeletogenic stem cells, as well as the in vivo treatment of skeletal tissue deficiencies. The present invention particularly contemplates the use of hedgehog agonists which maintain a skeletal homeotic activity, such as an ability to induce chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the present invention makes available effective therapeutic methods and compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog agonist, particularly an Ihh agonist, to generate a cartilage repair response in the connective tissue by stimulating the differentiation and/or proliferation of chondrocytes embedded in the tissue. Induction of chondrocytes by treatment with a hedgehog agonist can subsequently result in the synthesis of new cartilage matrix by the treated cells. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralisation into fibrotic tissue by maintaining a constant production of new cartilage.

In an illustrative embodiment, the subject method is used to treat cartilage of a diarthroidal joint, such as a knee, an ankle, an elbow, a hip, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a hedgehog agonist into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252: 129), isolated chondrocytes (Grande et al. (1989) *J Orthop Res* 7: 208; and Takigawa et al. (1987) *Bone Miner* 2: 449), and chondrocytes attached to natural or synthetic polymers (Walitani et al. (1989) *J Bone Jt Surg* 71B: 74; Vacanti et al. (1991) *Plast Reconstr Surg* 88: 753; von Schroeder et al. (1991) *J Biomed Mater Res* 25: 329; Freed et al. (1993) *J Biomed Mater Res* 27: 11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog agonist during the culturing process, such as an Ihh agonist, in order to induce and/or maintain differentiated chondrocytes in the culture in order as to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a hedgehog agonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. Thus, preparations comprising hedgehog agonists can be employed, for example, to induce endochondral ossification, at least so far as to facilitate the formation of cartilaginous tissue precursors to form the "model" for ossification. Therapeutic compositions of hedgehog agonists can be supplemented, if required, with other osteoinductive factors, such as bone morphogenic proteins (and other TGF-$\beta$ factors).

In yet another embodiment of the present invention, a hedgehog antagonist can be used to inhibit spermatogenesis. Thus, in light of the present finding that hedgehog proteins are involved in the differentiation and/or proliferation and maintenance of testicular germ cells, hedgehog antagonist can be utilized to block the action of a naturally-occuring hedgehog protein. In a preferred embodiment, the hedgehog antagonist inhibits the biological activity of Dhh with respect to spermatogenesis, by competitively binding hedgehog receptors in the testis. In similar fashion, hedgehog agonists and antagonists are potentially useful for modulating normal ovarian function.

The hedgehog protein, or a pharmaceutically acceptable salt thereof, may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined emperically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog protein, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of a hedgehog homolog (such as a Shh, Dhh or Mhh) in association with one or more pharmaceutically acceptable vehicles or diluents, and contained in buffered media at a suitable pH and isosmotic with physiological fluids. For illustrative purposes only and without being limited by the same, possible compositions or formulations which may be prepared in the form of solutions for the treatment of nervous system disorders with a hedgehog protein are given in U.S. Pat. No. 5,218,094. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of hh in isotonic solutions of the desired volume and include, but not exclusively, the use of buffered saline solutions with phosphate or citrate at suitable concentrations so a s to obtain at all times isotonic pharmaceutical preparations of the desired pH, (for example, neutral pH).

Methods of introduction of exogenous hh at the site of treatment include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir.

Methods of introduction may also be provided by rechargable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an hh at a particular target site. Such embodiments of the present invention can be used for the delivery of an exogenously purified hedgehog protein, which has been incorporated in the polymeric device, or for the delivery of hedgehog produced by a cell encapsulated in the polymeric device.

An essential feature of certain embodiments of the implant can be the linear release of the hh, which can be achieved through the manipulation of the polymer composition and form. By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666. In another embodiment of an implant, a source of cells producing a hedgehog protein, or a solution of hydogel matrix containing purified hh, is encapsulated in implantable hollow fibers. Such fibers can be pre-spun and subsequently loaded with the hedgehog source (Aebischer et al. U.S. Pat. No. 4,892,538; Aebischer et al. U.S. Pat. No. 5,106,627; Hoffman et al. (1990) *Expt. Neurobiol.* 110: 39–44; Jaeger et al. (1990) *Prog. Brain Res.* 82: 41–46; and Aebischer et al. (1991) *J Biomech. Eng.* 113: 178–183), or can be co-extruded with a polymer which acts to form a polymeric coat about the hh source (Lim U.S. Pat. No. 4,391,909; Sefton U.S. Pat. No. 4,353,888; Sugamori et al. (1989) *Trans. Am. Artif Intern. Organs* 35: 791–799; Sefton et al. (1987) *Biotehnol. Bioeng.* 29: 1135–1143; and Aebischer et al. (1991) *Biomaterials* 12: 50–55).

In yet another embodiment of the present invention, the pharmaceutical hedgehog protein can be administered as part of a combinatorial therapy with other agents. For example, the combinatorial therapy can include a hedgehog protein with at least one trophic factor. Exemplary trophic factors include nerve growth factor, cilliary neurotrophic growth factor, schwanoma-derived growth factor, glial growth factor, stiatal-derived neuronotrophic factor, platelet-derived growth factor, and scatter factor (HGF-SF). Antimitogenic agents can also be used, for example, when proliferation of surrounding glial cells or astrocytes is undesirable in the regeneration of nerve cells. Examples of such antimitotic agents include cytosine, arabinoside, 5-fluorouracil, hydroxyurea, and methotrexate.

EXEMPLIFICATION

The invention, now being generally described, will be more readily understood by reference to the following examples, which are included merely for purposes of illustration of certain aspects and embodiments of the present invention and are not intended to limit the invention.

EXAMPLE 1

Cloning and Expression of Chick Sonic Hedgehog (i) Experimental Procedures

Using degenerate PCR primers, vHH5O (SEQ ID NO: 18), vHH3O (SEQ ID NO: 19) and vHH3I (SEQ ID NO: 20) corresponding to a sequence conserved between Drosophila hedgehog (SEQ ID NO: 11) (Lee, J. J. et al. (1992) *Cell* 71: 33–50; Mohler, J. et al., (1992) *Development* 115: 957–971) and mouse Indian hedgehog (Ihh) (SEQ ID NO: 6), a 220 base pair (bp) fragment was amplified from chicken genomic DNA. From 15 isolates, two distinct sequences were cloned, pCHA (SEQ ID NO: 12) and pCHB (SEQ ID NO: 13), each highly homologous to mouse Ihh (FIG. 1). A probe made from isolate pCHA did not detect expression in embryonic tissues. Isolate pCHB, however, detected a 4 kb message in RNA prepared from embryonic head, trunk, or limb bud RNA. This cloned PCR fragment was therefore used as a probe to screen an unamplified cDNA library prepared from Hamburger Hamilton stage 22 (Hamburger, W. et al., (1951) *J Morph.* 88: 49–92) limb bud RNA as described below.

A single 1.6 kilobase (kb) cDNA clone, pHH-2, was selected for characterization and was used in all subsequent analyses. The gene encoding for this cDNA was named Sonic Hedgehog (after the Sega computer game cartoon character). Sequencing of the entire cDNA confirmed the presence of a single long open reading frame potentially encoding for a protein of 425 amino acids (aa). The clone extends 220 bp upstream of the predicted initiator methionine and approximately 70 bp beyond the stop codon. No consensus polyadenylation signal could be identified in the 3' untranslated region. A second potential initiator methionine occurs at amino acid residue 4. The putative translation initiation signals surrounding both methionines are predicted to be equally efficient (Kozak, M., (1987) *Nuc. Acids Res.* 15: 8125–8132). When the Sonic cDNA is used to probe a northern blot of stage 24 embryonic chick RNA, a single mRNA species of approximately 4 kb is detected in both limb and trunk tissue (FIG. 2). Therefore, since the Sonic cDNA clone pHH-2 is only 1.6 kb, it is likely to be missing approximately 2.4 kb of untranslated sequence.

PCR Cloning

All standard cloning techniques were performed according to Ausubel et. al. (1989), and all enzymes were obtained from Boehringer Mannheim Biochemicals. Degenerate oligonucleotides corresponding to amino acid residues 161 to 237 of the Drosophila hedgehog protein (SEQ ID NO: 11) (Lee, J. J. et. al., (1992) Cell 71: 33–50) were synthesized. These degenerate oligonucleotides, vHH5O (SEQ ID NO: 18), vHH3O (SEQ ID NO: 19), and vHH3I (SEQ ID NO: 20) also contained Eco RI, Cla I, and Xba I sites, respectively, on their 5' ends to facilitate subcloning. The nucleotide sequence of these oligos is given below:

vHH5O: 5'-GGAATTCCCAG(CA)GITG(CT)AA(AG)GA(AG)(CA)(AG)I(GCT)IAA-3' vHH3O: 5'-TCATCGATGGACCCA(GA)TC,(GA)AAIC-CIGC(TC)TC-3' vHH3I: 5'-GCTCTAGAGCTCIACIGCIA(GA)IC(GT)IGC-3' where I represents inosine. Nested PCR was performed by first amplifying chicken genomic DNA using the vHH5O and vHH3O primer pair and then further amplifying that product using the vHH5O and vHH3I primer pair. In each case the reaction conditions were: initial denaturation at 93° C. for 2.5 min., followed by 30 cycles of 94° C. for 45 s, 50° C. for 1 min., 72° C. for 1, and a final incubation of 72° C. for 5 min. The 220 bp PCR product was subcloned into pGEM7zf (Promega). Two unique clones, pCHA (SEQ ID NO: 12) and pCHB (SEQ ID NO: 13) were identified.

DNA Sequence Analysis

Nucleotide sequences were determined by the dideoxy chain termination method (Sanger, F. et al., (1977) Proc. Natl. Acad. Sci. USA 74: 5463–5467) using Sequenase v2.0 T7 DNA polymerase (US Biochemicals). 5' and 3' nested deletions of pHH-2 were generated by using the nucleases Exo III and SI (Erase a Base, Promega) and individual subclones sequenced. DNA and amino acid sequences were analyzed using both GCG (Devereux, J. et al., (1984) Nuc. Acids Res. 12: 387–394) and DNAstar software. Searches for related sequences were done through the BLAST network service (Altschul, S. F. et al., (1990) J Mol. Biol. 215: 403–410) provided by the National Center for Biotechnology Information.

Southern Blot Analysis

Five (5) µg of chick genomic DNA was digested with Eco RI and/or Bam HI, fractionated on a 1% agarose gel, and transferred to a nylon membrane (Genescreen, New England Nuclear). The filters were probed with $^{32}$P-labeled hha or hhb at 42° C. in hybridization buffer (0.5% BSA, 500 mM NaHPO$_4$, 7% SDS, 1 mM EDTA, pH 7.2; Church, G. M. et al., (1984) Proc. Natl. Acad. Sci. USA 81: 1991–1995). The blots were washed at 63° C. once in 0.5% bovine serum albumin, 50 mM NaHPO$_4$ (pH 7.2), 5% SDS, 1 mM EDTA and twice in 40 mM NaHPO$_4$ (pH 7.2), 1% SDS, 1 mM EDTA, and visualized on Kodak XAR-5 film.

Isolation Of Chicken Sonic cDNA Clones

A stage 22 limb bud cDNA library was constructed in λgt10 using Eco RI/NotI linkers. Unamplified phage plaques ($10^6$) were transferred to nylon filters (Colony/Plaque screen, NEN) and screened with $\alpha^{32}$P-labelled pooled inserts from PCR clones pCHA (SEQ ID NO: 12) and pCHB (SEQ ID NO: 13). Hybridization was performed at 42° C. in 50% formamide 2×SSC, 10% dextran sulfate, 1% SDS and washing as described in the Southern Blot procedure. Eight positive plaques were identified, purified and their cNA inserts excised with EcoRI and subcloned into pBluescript SK+ (Stratagene). All eight had approximately 1.7 kb inserts with identical restriction patterns. One, pHH-2, was chosen for sequencing and used in all further manipulations.

Preparation Of Digoxigenin-Labeled Riboprobes

Plasmid pHH-2 was linearized with Hind III and transcribed with T3 RNA polymerase (for antisense probes) or with Bam HI and transcribed with T7 RNA polymerase according to the manufacturers instructions for the preparation of non-radioactive digoxigenin transcripts. Following the transcription reaction, RNA was precipitated, and resuspended in RNAse-free water.

Whole Mount In Situ Hybridization

Whole-mount in situ hybridization was performed using protocols modified from Parr, B. A. et al., (1993) Development 119: 247–261; Sasaki, H. et al. (1993) Development 118: 47–59; Rosen, B. et al. (1993) Trends Genet. 9: 162–167. Embryos from incubated fertile White Leghorn eggs (Spafas) were removed from the egg and extraembryonic membranes dissected in calcium/magnesium-free phosphate-buffered saline (PBS) at room temperature. Unless otherwise noted, all washes are for five minutes at room temperature. Embryos were fixed overnight at 4° C. with 4% paraformaldehyde in PBS, washed twice with PBT (PBS with 0.1% Tween-20) at 4° C., and dehydrated through an ascending methanol series in PBT (25%, 50%, 75%, 2×100% methanol). Embryos were stored at −20° C. until further use.

Both pre-limb bud and limb bud stage embryos were rehydrated through an descending methanol series followed by two washes in PBT. Limb bud stage embryos were bleached in 6% hydrogen peroxide in PBT, washed three times with PBT, permeabilized with proteinase K (Boehringer, 2 µg/ml) for 15 minutes, washed with 2 mg/ml glycine in PBT for 10 minutes, and twice with PBT. Pre-limb bud stage embryos were permealibized (without prior incubation with hydrogen peroxide) by three 30 minute washes in RIPA buffer (150 mM NaCl, 1% NP-40, 0.5% Deoxycholate, 0.1% SDS, 1 mM EDTA, 50 mM Tris-HCl, pH 8.0). In all subsequent steps, pre-limb bud and limb bud stage embryos were treated equivalently. Embryos were fixed with 4% paraformaldehyde/0.2% gluteraldehyde in PBT, washed four times with PBT, once with pre-hybridization buffer (50% formamide, 5×SSC, 1% SDS, 50 µg/ml total yeast RNA, 50 µg/ml heparin, pH 4.5), and incubated with fresh pre-hybridization buffer for one hour at 70° C. The pre-hybridization buffer was then replaced with hybridization buffer (pre-hybridization buffer with digoxigenin labeled riboprobe at 1 µg/ml) and incubated overnight at 70° C.

Following hybridization, embryos were washed 3×30 minutes at 70° C. with solution 1 (50% formamide, 5×SSC, 1% SDS, pH 4.5), 3×30 minutes at 70° C. with solution 3 (50% formamide, 2×SSC, pH 4.5), and three times at room temperature with TBS (Tris-buffered saline with 2 mM levamisole) containing 0.1% Tween-20. Non-specific binding of antibody was prevented by preblocking embryos in TBS/0.1% Tween-20 containing 10% heat-inactivated sheep serum for 2.5 hours at room temperature and by pre-incubating anti-digoxigenin Fab alkaline-phosphatase conjugate (Boehringer) in TBS/0.1% Tween-20 containing heat inactivated 1% sheep serum and approximately 0.3% heat inactivated chick embryo powder. After an overnight incubation at 4° C. with the pre-adsorbed antibody in TBS/0.1% Tween-20 containing 1% sheep serum, embryos were washed 3×5 minutes at room temperature with TBS/0.1% Tween-20, 5×1.5 hour room temperature washes with TBS/1% Tween-20, and overnight with TBS/1% Tween-20 at 4° C. The buffer was exchanged by washing 3×10 minutes with NTMT (100 mM NaCl, 100 mM Tris-HCl, 50 mM MgCl2, 0.1% Tween-20, 2 mM levamisole). The antibody detection reaction was performed by incubating embryos with detection solution (NTMT with 0.25 mg/ml NBT and 0.13 mg/ml X-Phos). In general, pre-limb bud stage embryos were incubated for 5–15 hours and limb bud stage embryos 1–5 hours. After the detection reaction was deemed complete, embryos were washed twice with NTMT, once with PBT (pH 5.5), postfixed with 4% paraformaldehyde/0.1% gluteraldehyde in PBT, and washed several times with PBT. In some cases embryos were cleared through a series of 30%, 50%, 70%, and 80% glycerol in PBT. Whole embryos were photographed under transmitted light using a Nikon zoom stereo microscope with Kodak Ektar 100 ASA film. Selected embryos were processed for frozen sections by dehydration in 30% sucrose in PBS followed by embedding in gelatin and freezing. 25 μm cryostat sections were collected on superfrost plus slides (Fisher), rehydrated in PBS, and mounted with gelvatol. Sections were photographed with Nomarski optics using a Zeiss Axiophot microscope and Kodak Ektar 25 ASA film.

Figure 3:
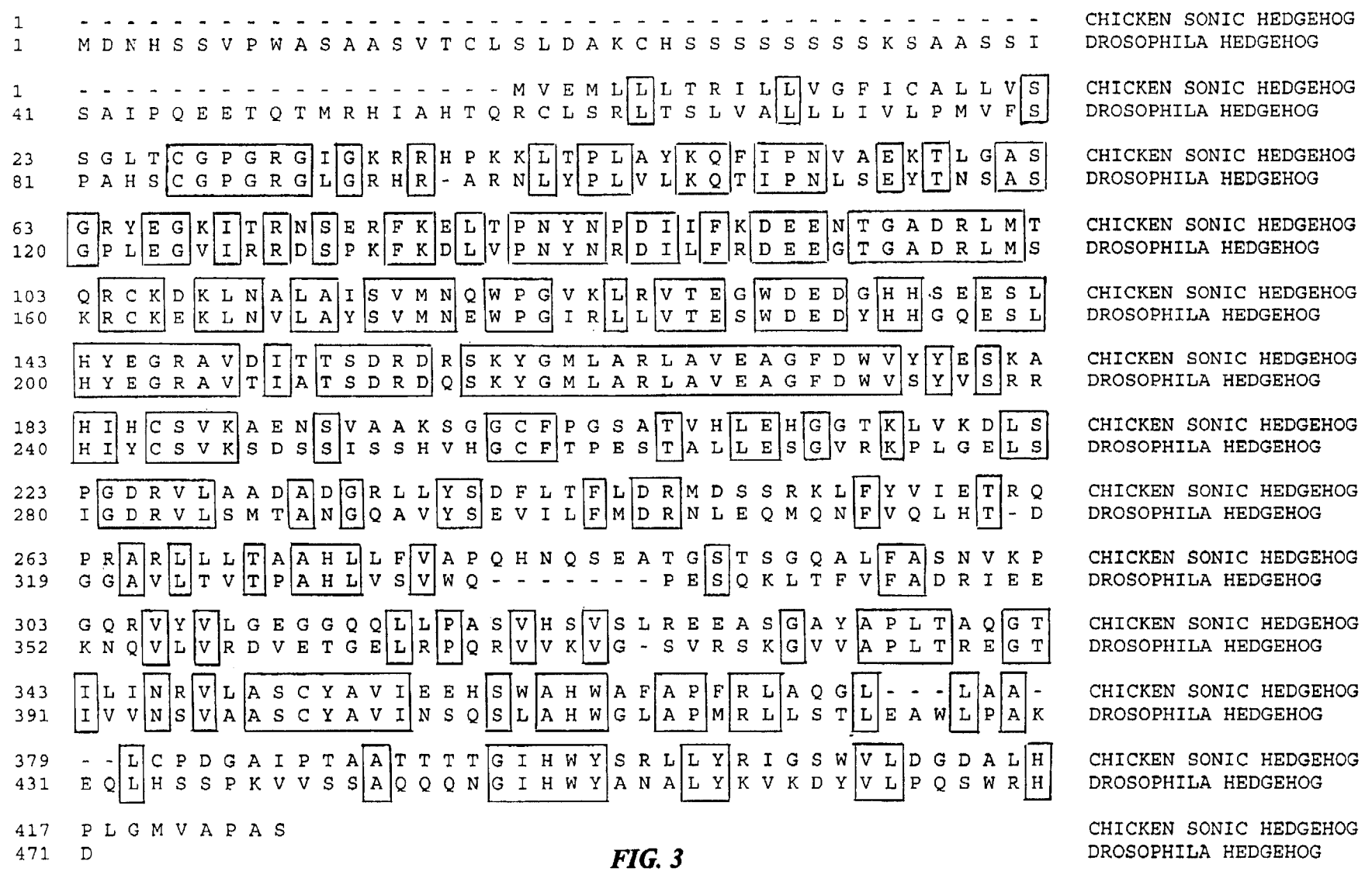

(ii) Sequence Homology Comparison Between Chicken Sonic hh And Drosophila hh And Other Vertebrate Sonic hh Proteins The deduced Sonic amino acid sequence (SEQ ID NO: 2) is shown and compared to the Drosophila hedgehog protein (SEQ ID NO: 11) in FIG. 3. Over the entire open reading frame the two proteins are 48% homologous at the amino acids level. The predicted Drosophila protein extends 62 aa beyond that of Sonic at its amino terminus. This N-terminal extension precedes the putative signal peptide (residues 1–26) of the fly protein (SEQ ID NO: 11), and has been postulated to be removed during processing of the secreted form of Drosophila hedgehog (Lee, J. J. et al., (1992) *Cell* 71: 33–50). The sequence of residues 1–26 of the Sonic protein (SEQ ID NO: 2) matches well with consensus sequences for eukaryotic signal peptides (Landry, S. J. et al., (1993) *Trends. Biochem. Sci.* 16: 159–163) and is therefore likely to serve that function for Sonic. Furthermore, FIG. 4 shows a hydropathy plot (Kyte, J. et al., (1982) *J Mol. Biol.* 157: 133–148) indicating that residues 1–26 of the Sonic protein (SEQ ID NO: 2) exhibit a high hydrophobic moment in accord with identified eukaryotic signal peptides. Cleavage of the putative signal sequence should occur C-terminal to residue 26 according to the predictive method of von Henjie, G. (1986) *Nuc. Acid. Res.* 11: 1986. A single potential N-linked glycosylation site is located at amino acid residue 282 of the Sonic protein (SEQ ID NO: 2). The predicted Sonic protein does not contain any other strong consensus motifs, and is not homologous to any other proteins outside of the Hedgehog family.

Figure 5:
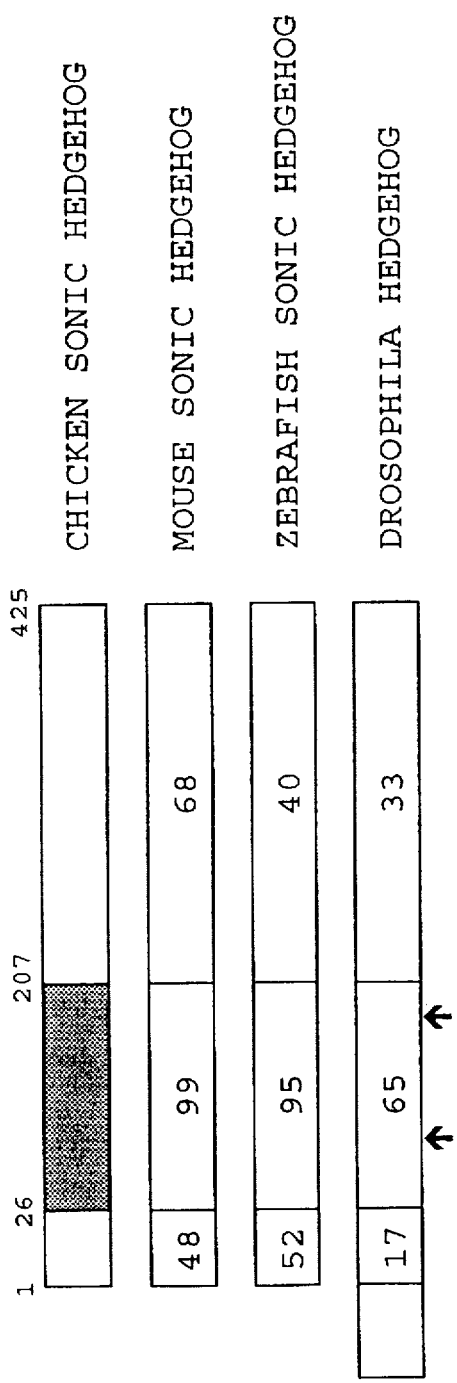
FIG. 5 is an alignment comparing the amino acid sequences of various hh proteins. The white region on the amino terminus of chicken Shh corresponds to the putative signal peptide. The black box refers to a highly conserved region from aa residues 26–207 of SEQ ID NO: 2). The arrows point to exon boundaries in the Drosophila gene (Lee et al. (1992) *Cell* 71: 33–50). In each case, the proteins are compared to chicken Shh (SEQ ID NO: 2) and the percent amino acid identity is indicated in each region's box.

The mouse (SEQ ID NO: 8) and zebrafish (SEQ ID NO: 10) homologs of Sonic have also been isolated. A comparison of these and the Drosophila sequence is shown schematically in FIG. 5. All of the vertebrate proteins have a similar predicted structure: a putative signal peptide at their amino terminus, followed by an extraordinarily similar 182 amino acid region (99% identity in chicken versus mouse and 95% identity in chicken versus zebrafish) and a less well conserved carboxy-terminal region.

(iii) At Least Three Hedgehog Homologues Are Present In The Chicken Genome

Since two distinct PCR products encoding for chicken hedgehogs were amplified from genomic DNA, the total number of genes in the chicken hedgehog family needed to be estimated. The two PCR clones pCHA (SEQ ID NO: 12) and pCHB (SEQ ID NO: 13) were used to probe a genomic Southern blot (FIG. 6) under moderately stringent conditions as described in the above Experimental Procedures. Each probe reacted most strongly with a distinct restriction fragment. For example, in panel A, probed with pCHA, three bands can be seen in each of the Bam HI lanes, one strong at 6.6 kb and two weak at 3.4 and 2.7 kb. In panel B, probed with pCHB, the 2.7 kb band is the most intense, while the 3.4 and 6.6 kb bands are weaker. A similar variation of intensities can also be seen in the Bam HI/Eco RI and EcoRI lanes. This data indicates that each probe recognizes a distinct chicken hedgehog gene, and that a third as yet uncharacterized chicken hedgehog homolog exists in the chicken genome.

(iv) Northern Analysis Defining Sites Of Sonic Transcription

Northern analysis was performed which confirmed that Sonic is expressed during chick development. The spatial and temporal expression of Sonic in the chick embryo from gastrulation to early organogenesis was determined by whole mount in situ hybridization using a riboprobe corresponding to the full-length Sonic cDNA (SEQ ID NO: 1).

20 μg total RNA isolated from stage 24 chick leg buds or bodies (without heads or limbs) was fractionated on a 0.8% agarose formaldehyde gel and transferred to a nylon membrane (Hybond N, Amersham). The blot was probed with the 1.6 kb EcoRI insert from pHH-2. Random-primed $\alpha^{32}$P-labelled insert was hybridized at 42° C. hybridization buffer (1% BSA, 50 mM NaHPO$_4$, 7% SDS, 1 mM EDTA, pH 7.2) and washed at 63° C. once in 0.5% bovine serum albumin, 50 mM NaHPO$_4$ (pH 7.2), 5% SDS, 1 mM EDTA and once in 40 mM NaHPO$_4$ (pH 7.2), 1% SDS, 1 mM EDTA. The image was visualized using a phosphoimager (Molecular Dynamics) and photographed directly from the video monitor.

(v) Expression Of Sonic During Mid-Gastrulation

Sonic message is detected in the gastrulating blastoderm at early stage 4, the earliest stage analyzed. Staining is localized to the anterior end of the primitive streak in a region corresponding to Hensen's node. As gastrulation proceeds, the primitive streak elongates to its maximal cranial-caudal extent, after which Hensen's node regresses caudally and the primitive streak shortens. At an early point of node regression, Sonic MRNA can be detected at the node and in midline cells anterior to the node. By late stage 5, when the node has migrated approximately one-third of the length of the fully elongated primitive streak, prominent Sonic expression is seen at the node and in the midline of the embryo, reaching its anterior limit at the developing head process. Sections at a cranial level show that Sonic mRNA is confined to invaginated axial mesendoderm, tissue which contributes to foregut and notochord. More caudally, but still anterior to Hensen's node, staining of axial mesoderm is absent and Sonic expression is confined to the epiblast. At the node itself, high levels of Sonic message are observed in an asymmetric distribution extending to the left of and posterior to the primitive pit. This asymmetric distribution is consistently observed (6/6 embryos from stages 5-7) and is always located to the left of the primitive pit. At the node, and just posterior to the node, Sonic expression is restricted to the epiblast and is not observed in either mesoderm or endoderm. The expression of Sonic in the dorsal epiblast layer without expression in underlying axial mesoderm contrasts markedly with later stages where Sonic expression in underlying mesoderm always precedes midline neural tube expression.

(vi) Expression Of Sonic During Head Fold Stages

During the formation and differentiation of the head process, Sonic MRNA is detected in midline cells of the neural tube, the foregut, and throughout most of the axial mesoderm. At stage 7, Sonic message is readily detected asymmetrically at the node and in ventral midline cells anterior to the node. The rostral limit of Sonic expression extends to the anterior-most portions of the embryo where it is expressed in the foregut and prechordal mesoderm (Adelmann, H. B., (1932) *Am. J Anat.* 31, 55-101). At stage 8, expression of Sonic persists along the entire ventral midline anterior to Hensen's node, while the node region itself no longer expresses Sonic. Transverse sections at different axial levels reveal that at stage 8 Sonic is coexpressed in the notochord and the overlying ventromedial neuroectoderm from anterior to Hensen's node to the posterior foregut. The levels of Sonic message are not uniform in the neural tube: highest levels are found at the presumptive mid- and hindbrain regions with progressively lower levels anterior and posterior. The increasing graded expression in the neural tube from Hensen's node to the rostral brain may reflect the developmental age of the neuroectoderm as differentiation proceeds from posterior to anterior. At the anterior-most end of the embryo, expression is observed in midline cells of the dorsal and ventral foregut as well as in prechordal mesoderm. Although the prechordal mesoderm is in intimate contact with the overlying ectoderm, the latter is devoid of Sonic expression.

(vii) Expression Of Sonic During Early CNS Differentiation

At stages 10 through 14, Sonic expression is detected in the notochord, ventral neural tube (including the floor plate), and gut precursors. By stage 10, there is a marked expansion of the cephalic neuroectoderm, giving rise to the fore- mid- and hind-brain. At stage 10, Sonic mRNA is abundantly expressed in the ventral midline of the hindbrain and posterior midbrain. This expression expands laterally in the anterior midbrain and posterior forebrain. Expression does not extend to the rostral forebrain at this or later stages. Sections reveal that Sonic is expressed in the notochord, the prechordal mesoderm, and the anterior midline of the foregut. Expression in the neuroepithelium extends from the forebrain caudally. In the posterior-most regions of the embryo which express Sonic, staining is found only in the notochord and not in the overlying neurectoderm. This contrasts with earlier expression in which the posterior domains of Sonic expression contain cells are located in the dorsal epiblast, but not in underlying mesoderm or endoderm. Midgut precursors at the level of the anterior intestinal portal also show weak Sonic expression.

At stage 14, expression continues in all three germ layers. The epithelium of the closing midgut expresses Sonic along with portions of the pharyngeal endoderm and anterior foregut. Ectoderm lateral and posterior to the tail bud also exhibits weak expression. At this stage, Sonic is also expressed along entire length of the notochord which now extends rostrally only to the midbrain region and no longer contacts the neuroepithelium at the anterior end of the embryo. Expression in head mesenchyme anterior to the notochord is no longer observed. In the neural tube Sonic is found along the ventral midline of the fore- mid- and hindbrain and posteriorly in the spinal cord. In the forebrain, expression is expanded laterally relative to the hindbrain. At midgut levels, expression of Sonic in the neural tube appears to extend beyond the floor plate into more lateral regions. As observed at stage 10, Sonic at stage 14 is found in the notochord, but not in the ventral neural tube in posterior-most regions of the embryo. When neuroectodermal expression is first observed in the posterior embryo, it is located in midline cells which appear to be in contact with the notochord. At later stages, expression continues in areas which show expression at stage 14, namely the CNS, gut epithelium including the allantoic stalk, and axial mesoderm.

(viii) Sonic Is Expressed In Posterior Limb Bud Mesenchyme

The limb buds initially form as local thickenings of the lateral plate mesoderm. As distal outgrowth occurs during stage 17, Sonic expression becomes apparent in posterior regions of both the forelimb and the hindlimb. Sections through a stage 21 embryo at the level of the forelimbs reveal that expression of Sonic in limb buds is limited to mesenchymal tissue. A more detailed expression profile of Sonic during limb development is discussed below in Example 3. Briefly, as the limb bud grows out, expression of Sonic narrows along the anterior-posterior axis to become a thin stripe along the posterior margin closely apposed to the ectoderm. Expression is not found at more proximal regions of the bud. High levels of Sonic expression are maintained until around stage 25/26 when staining becomes weaker. Expression of Sonic is no longer observed in wing buds or leg buds after stage 28.

EXAMPLE 2

Mouse Sonic Hedgehog Is Implicated in the Regulation of CNS and Limb Polarity (i) Experimental Procedures Isolation Of Hedgehog Phage Clones The initial screen for mammalian hh genes was performed, as above, using a 700 bp PCR fragment encompassing exons 1 and 2 of the Drosophila hh gene. Approximately one million plaques of a 129/Sv Lambda Fix II genomic library (Stratagene) were hybridized with an α $^{32}$P-dATP labeled probe at low stringency (55° C. in 6×SSC, 0.5% SDS, 5×Denhardt's; final wash at 60° C. in 0.5×SSC, 0.1% SDS for 20'). Five cross hybridizing phage plaques corresponding to the Dhh gene were purified. Restriction enzyme analysis indicated that all clones were overlapping. Selected restriction enzyme digests were then performed to map and subclone one of these. Subclones in pGEM (Promega) or Bluescript (Stratagene) which crosshybridized with the Drosophila hh fragment where sequenced using an ABI automatic DNA sequencer.

Mouse Ihh and Shh were identified by low stringency hybridization (as described above) with a chick Shh cDNA clone to one million plaques of an 8.5 day λgt10 mouse embryo cDNA library (Fahrner, K. et al., (1987) *EMBO J* 6: 1265–1271). Phage plaques containing a 1.8 kb Ihh and 0.64 and 2.8 kb Shh inserts were identified. Inserts were excised and subcloned into Bluescript (Stratagene) for dideoxy chain termination sequencing using modified T7 DNA polymerase (USB). The larger Shh clone contained a partially processed cDNA in which intron splicing at the exon ½ junction had not occurred.

To screen for additional Ihh and Shh cDNA clones, an 8.5 day λZAPII cDNA library was probed at high stringency (at 65° C. in 6×SSC, 0.5% SDS, 5×Denhardt's; final wash at 65° C. in 0.1×SSC, 0.1% SDS for 30') with the Ihh and Shh mouse cDNA clones. No additional Ihh clones were identified. However several 2.6 kb, apparently full length, Shh clones were isolated. The DNA sequence of the additional 5' coding region not present in the original 0.64 and 2.8 kb Shh clones was obtained by analysis of one of the 2.6 kb inserts.

Northern Blot Analysis

Expression of Shh was investigated by RNA blot analysis using 20 μg of total RNA from adult brain, spleen, kidney, liver, lung, 16.5 dpc brain, liver and lung; 9.5 dpc to 17.5 dpc whole embryo; 9.5 dpc forebrain, midbrain and 10.5 dpc brain. RNA samples were electrophoretically separated on a 1.2% agarose gel, transferred and u.v. crosslinked to Genescreen (DuPont) and probed with 2×10$^6$ cpm/ml of an α$^{32}$p-dATP labeled mouse Shh probe (2.8 kb insert from kgt 10 screen). Hybridization was performed at 42° C. in 50% formamide 5×Denhardt's, 5×SSPE, 0.1% SDS, 6.5% dextran, 200 μg/ml salmon sperm DNA. Final wash was at 55° C. in 0.1×SSC, 0.1% SDS. The blot was exposed for 6 days in the presence of an intensifying screen.

In Situ Hybridization, β-Galactosidase Staining And Histological Analysis

Embryos from 7.25 to 14.5 dpc were analyzed for either Shh or HNF-3β expression by whole mount in situ hybridization to digoxygenin labeled RNA probes as described in Wilkinson, (1992) *In situ Hybridization: A Practical Approach*. Oxford; Parr et al., (1993) *Development* 119: 247–261. The mouse Shh probe was either a 2.8 kb or 0.6 kb RNA transcript generated by T7 (2.8 kb) or T3 (0.6 kb) transcription of XbaI and HindIII digests of Bluescript (Stratagene) subclones of the original Shh cDNA inserts. The HNF-3β probe was generated by HindIII linearization of a HNF-3β cDNA clone (Sasaki, H. et al., (1993) *Development* 118: 47–59) and T7 polymerase transcription of 1.6 kb transcript. Embryos were photographed on an Olympus-SZH photomicroscope using Kodak Ektachrome EPY 64T color slide film.

Sections through wild type and WEXP2-CShh transgenic embryos were prepared and hybridized with $^{35}$S-UTP labeled RNA probes (Wilkinson, D. G. et al., (1987) *Development* 99: 493–500). Sections were photographed as described in McMahon, A. P. et al., (1992) *Cell* 69: 581–595.

β Staining of WEXP2-lacZ embryos with βwas performed according to Whiting, J. et al., (1991) *Genes & Dev*. 5: 2048–2059. General histological analysis of wildtype and WEXP2-CShh transgenic embryos was performed on paraffin sections of Bouin's fixed embryos counterstained with haematoxylin and eosin. Histological procedures were as described by Kaufinan, M. H. (1992) *The Atlas of Mouse Development*, London: Academic Press. Sections were photographed on a Leitz Aristoplan compound microscope using Kodak EPY 64T color slide film.

DNA Constructs For Transgenics

Genomic Wnt-1 fragments were obtained by screening a λGEM12 (Promega) 129/Sv mouse genomic library with a 375 bp MluI-BglII fragment derived from the fourth exon of the murine Wnt-1 gene. One of the clones (WI-15.1) was used in this study.

As an initial step towards the generation of the pWEXP2 expression vector, W1-15.1 was digested to completion with restriction enzymes AatII and ClaI, and a 2774 bp AatII-ClaI fragment isolated. This fragment was ligated into AatIII and ClaI cut pGEM-7Zf vector (Promega), generating pW1-18. This plasmid was digested with HindII and ligated to annealed oligonucleotides lac1 (SEQ ID NO: 21) and lac2 (SEQ ID NO: 22) generating pW1-18S* which has a modified polylinker downstream of the ClaI restriction site. This construct (pW1-18*) was digested with ClaI and BglII and ligated with both the 2.5 kb 3' ClaI-BglII exon-intron region and 5.5 kb 3' BglII-BglII Wnt-1 enhancer, generating pWRES4. This construct contains a 10.5 kb genomic region which starts upstream of the Wnt-1 translation initiation codon (at an AatIII site approximately 1.0 kb from the ATG) and extends to a BglII site 5.5 kb downstream of the Wnt-1 polyadenylation signal. This plasmid also contains a 250 bp region of the neomycin phosphotransferase (neo) gene inserted in inverse orientation in the 3' transcribed but untranslated region. Finally, to generate the WEXP2 expression vector, a 2 kb Sfi I fragment was amplified from pWRES4 using Sf-1 (SEQ ID NO: 23) and Sf-2 (SEQ ID NO: 24) oligonucleotides. This amplified fragment was digested with Sfi I and inserted into Sfi I linearised pWRES4, generating pWEXP2. This destroys the Wnt-1 translation initiation codon, and replaces it by a polylinker containing Nru I, Eco RV, Sac II, and Bst BI restriction sites, which are unique in pWEXP2.

The WEXP2 - lacZ construct was obtained by inserting an end-filled Bgl II - Xho I lacZ fragment isolated from the pSDKlacZpA vector in the Nru I cut pWEXP2 expression vector. Similarly, the WEXP2 - CShh construct was obtained by inserting an end-filled XbaI cDNA fragment containing the full Chick Shh coding sequence (SEQ ID NO: 1) into the Nru I cut WEXP2 expression vector.

Oligonucleotide sequences are as follows:

lac1: 5'-AGCTGTCGACGCGGCCGCTACGTAGGT-TACCGACGTCAAGCTTAGATCTC-3' lac2: 5'-AGCTGAGATCTAAMGCTTGACGTCGG-TAACCTACGTAGCGGCCGCGTCGAC-3'

Sf-1: 5'-GATCGGCCAGGCAGGCCTCGC-GATATCGTCACCGCGGTATTCGAA-3'

Sf-2: 5'-AGTGCCAGTCGGGGCCCCCAGGGCCGCGCC-3'

Production And Genotyping Of Transgenic Embryos

Transgenic mouse embryos were generated by microinjection of linear DNA fragments into the male pronucleus of B6CBAF1/J (C57BL/6J × CBA/J) zygotes. CD-1 or B6CBAF1/J females were used as recipients for injected embryos. G$_o$ mice embryos were collected at 9.5, 10.5, and 11.5 dpc, photographed using an Olympus SZH stereophotomicroscope on Kodak EPY-64T color slide film, then processed as described earlier.

WEXP2-lacZ and WEXP2-CShh transgenic embryos were identified by PCR analysis of proteinase-K digests of yolk sacs. Briefly, yolk sacs were carefully dissected free from maternal and embryonic tissues, avoiding cross-contamination between littermates, then washed once in PBS. After overnight incubation at 55° C. in 50 µl of PCR proteinase-K digestion buffer (McMahon, A. P. et al., (1990) *Cell* 62: 1073–1085). 1 µl of heat-inactivated digest was subjected to polymerase chain reaction (PCR) in a 20 µl volume for 40 cycles as follows: 94° C. for 30 seconds, 55° C. for 30 seconds, 72° C. for 1 minute, with the reaction ingredients described previously (McMahon, A. P. et al., (1990) *Cell* 62: 1073–1085)). In the case of the WEXP2 - lacZ transgenic embryos, oligonucleotides 137 (SEQ ID NO: 25) and 138 (SEQ ID NO: 26) amplify a 352 bp lacZ specific product. In the case of the WEXP2-CShh embryos, oligonucleotides WPR2 (Wnt-1-specific) (SEQ ID NO: 27) and 924 (Chick Shh-specific) (SEQ ID NO: 28) amplify a 345 bp fragment spanning the insertion junction of the Chick-Shh cDNA in the WEXP2 expression vector. Table 1 summarizes the results of WEXP2-C-Shh transgenic studies.

Oligonucleotide sequences are as follows:

137: 5'-TACCACAGCGGATGGTTCGG-3'

138: 5' -GTGGTGGTTATGCCGATCGC-3'

WPR2: 5'-TAAGAGGCCTATAAGAGGCGG-3'

924: 5'-AAGTCAGCCCAGAGGAGACT-3'

(ii) Mouse hh Genes

The combined screening of mouse genomic and 8.5 day post coitum (dpc) cDNA libraries identified three mammalian hh counterparts (FIG. 7) which herein will be referred to as Desert, Indian and Sonic hedgehog (Dhh, Ihh and Shh, respectively). Sequences encoding Dhh (SEQ ID NO: 3) were determined from analysis of clones identified by low stringency screening of a mouse genomic library. DNA sequencing of one of five overlapping lambda phage clones identified three homologous regions encoding a single open reading frame interrupted by introns in identical position to those of the Drosophila hh gene (FIG. 7). Splicing across the exon ½ boundary was confirmed by polymerase chain reaction (PCR) amplification of first strand cDNA generated from adult testicular RNA. The partial sequence of Ihh (SEQ ID NO: 5) and the complete sequence of Shh (SEQ ID NO: 7) coding regions were determined from the analysis of overlapping cDNA clones isolated from 8.5 dpc cDNA libraries. The longest Shh clone, 2.6 kb, appears to be full length when compared with the Shh transcript present in embryonic RNAs. The 1.8 kb partial length Ihh cDNA is complete at the 3' end, as evidenced by the presence of a polyadenylation consensus sequence and short poly A tail.

Alignment of the predicted Drosophila hh protein sequence (SEQ ID NO: 11) with those of the mouse Dhh (SEQ ID NO: 4), Ihh (SEQ ID NO: 6) and Shh (SEQ ID NO: 8), and chick Shh (SEQ ID NO: 2) and zebrafish Shh (SEQ ID NO: 7), reveals several interesting features of the hh-family (FIG. 7). All the vertebrate hh-proteins contain an amino terminal hydrophobic region of approximately 20 amino acids immediately downstream of the initiation methionine. Although the properties of these new hh proteins have not been investigated, it is likely that this region constitutes a signal peptide and vertebrate hhs are secreted proteins. Signal peptide cleavage is predicted to occur (von Heijne, G., (1986) *Nucleic Acids Research* 14: 4683–4690) just before an absolutely conserved six amino acid stretch, CGPGRG (SEQ ID NO: 29) (corresponding to residues 85–90)(FIG. 7), in all hh proteins. This generates processed mouse Dhh (SEQ ID NO: 4) and Shh (SEQ ID NO: 8) proteins of 41 and 44 kd, respectively. Interestingly, Drosophila hh (SEQ ID NO: 11) is predicted to contain a substantial amino terminal extension beyond the hydrophobic domain suggesting that the Drosophila protein enters the secretory pathway by a type II secretory mechanism. This would generate a transmembrane tethered protein which would require subsequent cleavage to release a 43 kd secreted form of the protein. In vitro analysis of Drosophila hh is consistent with this interpretation (Lee, J. J. et al., (1992) *Cell* 71: 33–50). However, there also appears to be transitional initiation at a second methionine (position 51 of SEQ ID NO: 11) just upstream of the hydrophobic region (Lee, J. J. et al., (1992) *Cell* 71: 33–50), suggesting that Drosophila hh, like its vertebrate counterparts, may also be secreted by recognition of a conventional amino terminal signal peptide sequence.

Data base searches for protein sequences related to vertebrate hhs failed to identify any significant homologies, excepting Drosophila hh. In addition, searching the "PROSITE" data bank of protein motifs did not reveal any peptide motifs which are conserved in the different hh proteins. Thus, the hhs represent a novel family of putative cell signaling molecules.

One feature of the amino acid alignment is the high conservation of hh sequences. Vertebrate hhs share 47 to 51% amino acid identity with Drosophila hh throughout the predicted processed polypeptide sequence (FIG. 8). Dhh has a slightly higher identity than that of Ihh and Shh suggesting that Dhh may be the orthologue of Drosophila hh. Conservation is highest in the amino terminal half of the proteins, indeed, from position 85 (immediately after the predicted shared cleavage site) to 249, 62% of the amino acids are completely invariant amongst the Drosophila and vertebrate proteins. Comparison of mouse Dhh, Ihh and Shh where their sequences overlap in this more conserved region, indicates that Ihh and Shh are more closely related (90% amino acid identity; residues 85 to 266) than with the Dhh sequence (80% amino acid identity; residues 85 to 266). Thus, Ihh and Shh presumably resulted from a more recent gene duplication event.

Comparison of cross species identity amongst Shh proteins reveals an even more striking sequence conservation. Throughout the entire predicted processed sequence mouse and chick Shh share 84% of amino acid residues (FIG. 8). However, in the amino terminal half (positions 85 to 266) mouse and chick are 99% and mouse and zebrafish 94% identical in an 180 amino acid stretch. Conservation falls off rapidly after position 266 (FIG. 7).

In summary, hh family members are likely secreted proteins consisting of a highly conserved amino terminal and more divergent carboxyl terminal halves. The extreme interspecies conservation of the vertebrate Shh protein points to likely conservation of Shh function across vertebrate species.

(iii) Expression of Mouse Shh at the Axial Midline

Expression of Shh in the mouse was examined in order to explore the role of mouse Shh (SEQ ID NO: 8) in vertebrate development. Northern blots of embryonic and adult RNA samples were probed with a radiolabelled mouse Shh cDNA probe. An Shh transcript of approximately 2.6 kb was detected in 9.5 dpc whole embryo RNA, and 9.5 and 10.5 dpc brain RNA fractions. No expression was detected in total RNA samples from later embryonic stages. Of the late fetal and adult tissue RNAs examined Shh expression was only detected in 16.5 dpc and adult lung.

To better define the precise temporal and spatial expression of Shh an extensive series of whole mount and serial section in situ hybridizations were performed using digoxygenin and $^{35}$S-radiolabelled RNA probes, respectively, to mouse embryo samples from 7.25 dpc (mid streak egg cylinder stage of gastrulation) to 13.5 dpc. No Shh expression is detected at mid-gastrulation stages (7.25 dpc) prior to the appearance of the node, the mouse counterpart of the amphibian organizer and chick Hensen's node. When the primitive streak is fully extended and the midline mesoderm of the head process is emerging from the node (7.5 to 7.75 dpc). Shh is expressed exclusively in the head process. At late head fold stages, Shh is expressed in the node and midline mesoderm of the head process extending anteriorly under the presumptive brain. Just prior to somite formation, Shh extends to the anterior limit of the midline mesoderm, underlying the presumptive midbrain. As somites are formed, the embryonic axis extends caudally. The notochord, which represents the caudal extension of the head process, also expresses Shh, and expression is maintained in the node.

Interestingly, by 8 somites (8.5 dpc) strong Shh expression appears in the CNS. Expression is initiated at the ventral midline of the midbrain, above the rostral limit of the head process. By 10 somites CNS expression in the midline extends rostrally in the forebrain and caudally into the hindbrain and rostral spinal cord. Expression is restricted in the hindbrain to the presumptive floorplate, whereas midbrain expression extends ventro-laterally. In the forebrain, there is no morphological floor plate, however ventral Shh expression here is continuous with the midbrain. By 15 somites ventral CNS expression is continuous from the rostral limit of the diencephalon to the presumptive spinal cord in somitic regions. Over the next 18 to 24 hrs, to the 25–29 somite stage, CNS expression intensifies and forebrain expression extends rostral to the optic stalks. In contrast to all other CNS regions, in the rostral half of the diencephalon, Shh is not expressed at the ventral midline but in two strips immediately lateral to this area which merge again in the floor of the forebrain at its rostral limit. Expression of Shh in both the notochord and floorplate is retained until at least 13.5 dpc.

Several groups have recently reported the cloning and expression of vertebrate members of a family of transcription factors, related to the Drosophila forkhead gene. One of these, HNF-3β shows several similarities in expression to Shh (Sasaki, H. et al., (1993) *Development* 118: 47–59) suggesting that HNF-3β may be a potential regulator of Shh. To investigate this possibility, direct comparison of BNF-3β and Shh expression was undertaken. BNF-3β transcripts are first detected in the node (as previously reported by Sasaki, H. et al., (1993) supra), prior to the emergence of the head process and before Shh is expressed. From the node, expression proceeds anteriorly in the head process, similar to Shh expression. Activation of HNF-3β within the CNS is first observed at 2–3 somites, in the presumptive mid and hindbrain, prior to the onset of Shh expression. By 5 somites, expression in the midbrain broadens ventro-laterally, extends anteriorly into the forebrain and caudally in the presumptive floor plate down much of the neuraxis in the somitic region. Strong expression is maintained at this time in the node and notochord. However, by 10 somites expression in the head process is lost and by 25–29 somites notochordal expression is only present in the most extreme caudal notochord. In contrast to the transient expression of BNF-3β in the midline mesoderm, expression in the floor plate is stably retained until at least 11.5 dpc. Thus, there are several spatial similarities between the expression of BNF-3β and Shh in both the midline mesoderm and ventral CNS and it is likely that both genes are expressed in the same cells. However, in both regions, HNF-3β expression precedes that of Shh. The main differences are in the transient expression of HNF-3β in the head process and notochord and Shh expression in the forebrain. Whereas BNF-3β and Shh share a similar broad ventral and ventral lateral midbrain and caudal diencephalic expression, only Shh extends more rostrally into the forebrain. In general, these results are consistent with a model in which initial activation of Shh expression may be regulated by HNF-3β.

The similarity in Shh and NF-3β expression domains is also apparent in the definitive endoderm which also lies at the midline. Broad HNF-3β expression in the foregut pocket is apparent at 5 somites as previously reported by Sasaki, H. et al., (1993) supra. Shh is also expressed in the endoderm, immediately beneath the forebrain. Both genes are active in the rostral and caudal endoderm from 8 to 11 somites. Whereas HNF-3 is uniformly expressed, Shh expression is initially restricted to two ventro-lateral strips of cells. Ventral restricted expression of Shh is retained in the most caudal region of the presumptive gut until at least 9.5 dpc whereas HNF-3β is uniformly expressed along the dorsoventral axis. Both genes are expressed in the pharyngeal ectoderm at 9.5 dpc and expression is maintained in the gut until at least 11.5 dpc. Moreover, expression of Shh in the embryonic and adult lung RNA suggests that endodermal expression of Shh may continue in, at least some endoderm derived organs.

(iv) Expression Of Shh In The Limb

Expression of Shh is not confined to midline structures. By 30–35 somites (9.75 dpc), expression is detected in a small group of posterior cells in the forelimb bud. The forelimb buds form as mesenchymal outpocketings on the flanks, opposite somites 8 to 12, at approximately the 17 to 20 somite stage. Shh expression is not detectable in the forelimbs until about 30–35 somites, over 12 hours after the initial appearance of the limbs. Expression is exclusively posterior and restricted to mesenchymal cells. By 10.5 dpc, both the fore and hindlimbs have elongated substantially from the body flank. At this time Shh is strongly expressed in the posterior, distal aspect of both limbs in close association with the overlying ectoderm. Analysis of sections at this stage detects Shh expression in an approximately six cell wide strip of posterior mesenchymal cells. In the forelimb, Shh expression ceases by 11.5 dpc. However, posterior, distal expression is still detected in the hindlimb. No limb expression is detected beyond 12.5 dpc.

(v) Ectopic Expression Of Shh

Grafting studies carried out principally in the chick demonstrate that cell signals derived from the notochord and floor plate pattern the ventral aspect of the CNS (as described above). In the limb, a transient signal produced by a group of posterior cells in both limb buds, the zone of polarizing activity (ZPA), is thought to regulate patterning across the anterior-posterior axis. Thus, the sequence of Shh, which predicts a secreted protein and the expression profile in midline mesoderm, the floor plate and in the limb, suggest that Shh signaling may mediate pattern regulation in the ventral CNS and limb.

To determine whether Shh may regulate ventral development in the early mammalian CNS, a Wnt-1 enhancer was used to alter its normal domain of expression. Wnt-1 shows a dynamic pattern of expression which is initiated in the presumptive midbrain just prior to somite formation. As the neural folds elevate and fuse to enclose the neural tube, Wnt-1 expression in the midbrain becomes restricted to a tight circle, just anterior of the midbrain, the ventral midbrain and the dorsal midline of the diencephalon, midbrain, myelencephalon and spinal cord (Wilkinson, D. G. et al., (1987) Cell 50: 79–88; McMahon, A. P. et al., (1992) Cell 69: 581–595; Parr, B. A. et al., (1993) Development 119: 247–261).

Figure 9:
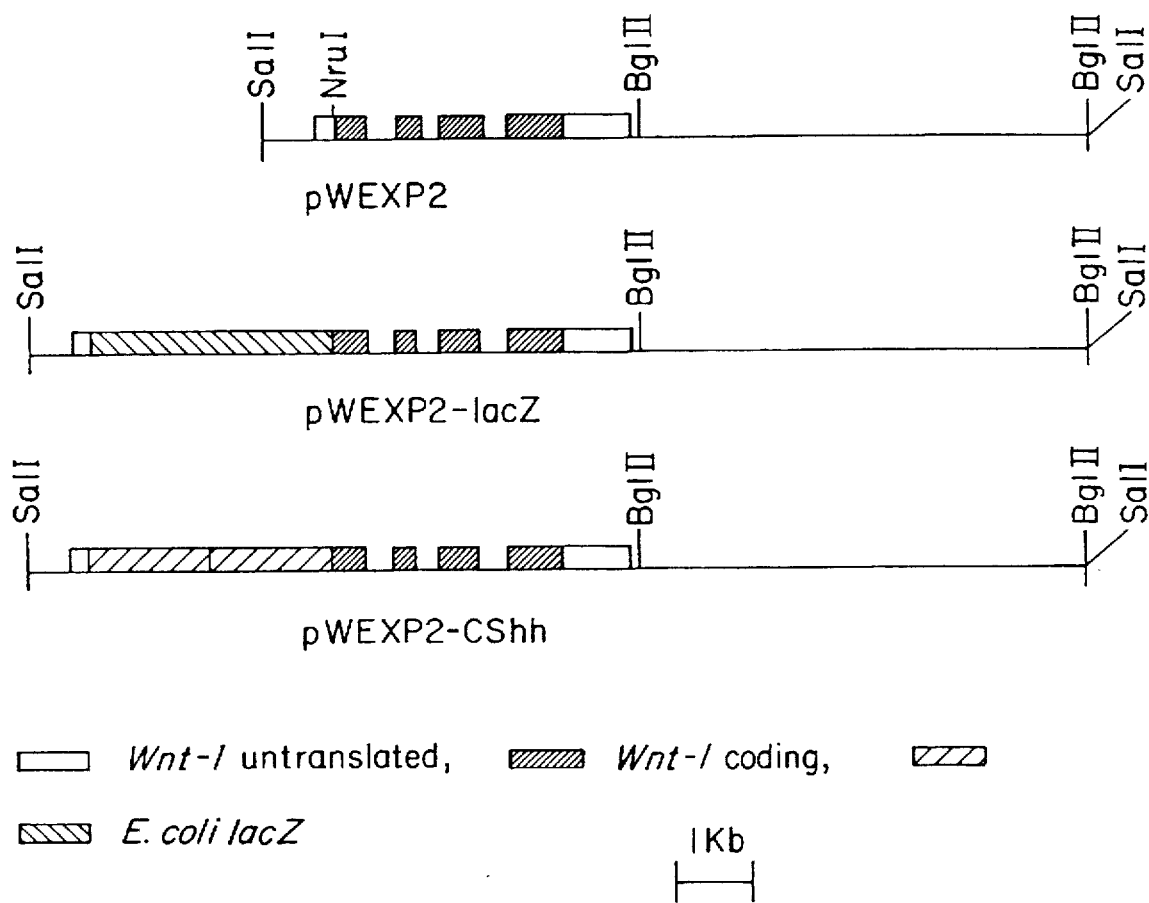
FIG. 9 is a representation of the DNA constructs used in transgenic studies to study ectopic expression of chick Shh in mouse embryos. Constructs were generated for ectopic expression of cDNA clones in the Wnt-1 expression domain and tested in transgenic mice embryos using a lac-Z reporter (pWEXP-lacZ (used as a control)) and a chick Shh reporter (pWEXP-CShh). The pWEXP-CShh costruct contained two tandem head to tail copies of a chick Shh cDNA. The results of WEXP2-CShh transgenic studies are shown in Table 1.

It was determined that essentially normal expression of lacZ reporter constructs within the Wnt-1 expression domain is dependent upon a 5.5 kb enhancer region which lies downstream of the Wnt-1 polyadenylation sequence. A construct was generated for ectopic expression of cDNA clones in the Wnt-1 domain and tested in transgenics using a lacZ reporter (pWEXP-lacZ; FIG. 9). Two of the four $G_o$ transgenic embryos showed readily detectable β-galactosidase activity, and in both expression occurred throughout the normal Wnt-1 expression domain. More extensive studies with a similar construct also containing the 5.5 kb enhancer gave similar frequencies. Some ectopic expression was seen in newly emerging neural crest cells, probably as a result of perdurance of β-galactosidase RNA or protein in the dorsally derived crest. Thus, the Wnt-1 expression construct allows the efficient ectopic expression of cDNA sequences in the midbrain and in the dorsal aspect of much of the CNS.

An Shh ectopic expression construct (pWEXP-CShh) containing two tandem head to tail copies of a chick Shh cDNA was generated (FIG. 9). By utilizing this approach, ectopic expression of the chick Shh is distinguishable from that of the endogenous mouse Shh gene. Chick Shh shows a high degree of sequence identity and similar expression to the mouse gene. Thus, it is highly likely that Shh function is widely conserved amongst vertebrates, a conclusion further supported by studies of the same gene in zebrafish.

Table 1 shows the results of several transgenic experiments in which the $G_o$ population was collected at 9.5 to 11.5 dpc. Approximately half of the transgenic embryos identified at each stage of development had a clear, consistent CNS phenotype. As we expect, on the basis of control studies using the 5.5 kb Wnt-1 enhancer, that only half the transgenics will express the transgene, it is clear that in most embryos ectopically expressing chick Shh, an abnormal phenotype results.

TABLE 1

Summary of WEXP2-Chick Shh transgenic studies

| Age (dpc) | Number of Embryos | Number of Transgenics | Number of Embryos with CNS phenotype* |
|---|---|---|---|
| 9.5 | 37 | 11 | 6 (54.5%) |
| 10.5 | 59 | 16 | 8 (50%) |
| 11.5 | 33 | 7 | 3 (42.9%) |

Figures in parentheses, refer to the percentage of transgenic embryos with a CNS phenotype
*In addition one 9.5 pc and two 10.5 pc transgenic embryos showed non-specific growth retardation, as occurs at low frequency in transgenic studies. These embryos were excluded from further analysis.

At 9.5 dpc, embryos with a weaker phenotype show an open neural plate from the mid diencephalon to the myelencephalon. In embryos with a stronger phenotype at the same stage, the entire diencephalon is open and telencephalic and optic development is morphologically abnormal. As the most anterior diencephalic expression of Wnt-1 is lower than that in more caudal regions, the differences in severity may relate to differences in the level of chick Shh expression in different $G_o$ embryos. At the lateral margins of the open neural folds, where Wnt-1 is normally expressed, there is a thickening of the neural tissue extending from the diencephalon to myelencephalon. The cranial phenotype is similar at 10.5 and 11.5 dpc. However, there appears to be a retardation in cranial expansion of the CNS at later stages.

In addition to the dorsal cranial phenotype, there is a progressive dorsal phenotype in the spinal cord. At 9.5 dpc, the spinal cord appears morphologically normal, except at extreme rostral levels. However by 10.5 dpc, there is a dorsal dysmorphology extending to the fore or hindlimbs. By 11.5 dpc, all transgenic embryos showed a dorsal phenotype along almost the entire spinal cord. Superficially, the spinal cord had a rippled, undulating appearance suggestive of a change in cell properties dorsally. This dorsal phenotype, and the cranial phenotype were examined by histological analysis of transgenic embryos.

Sections through a 9.5 dpc embryo with an extreme CNS phenotype show a widespread dorsal perturbation in cranial CNS development. The neural/ectodermal junction in the diencephalon is abnormal. Neural tissue, which has a columnar epithelial morphology quite distinct from the squamous epithelium of the surface ectoderm, appears to spread dorsolaterally. The myelencephalon, like the diencephalon and midbrain, is open rostrally. Interestingly, there are discontinuous dorso-lateral regions in the myelencephalon with a morphology distinct from the normal roof plate regions close to the normal site of Wnt-1 expression. These cells form a tight, polarized epithelium with basely located nuclei, a morphology similar to the floor plate and distinct from other CNS regions. Differentiation of dorsally derived neural crest occurs in transgenic embryos as can be seen from the presence of cranial ganglia. In the rostral spinal cord, the neural tube appeared distended dorso-laterally which may account for the superficial dysmorphology.

By 11.5 dpc, CNS development is highly abnormal along the entire dorsal spinal cord to the hindlimb level. The dorsal half of the spinal cord is enlarged and distended. Dorsal sensory innervation occurs, however, the neuronal trajectories are highly disorganized. Most obviously, the morphology of dorsal cells in the spinal cord, which normally are elongated cells with distinct lightly staining nuclei and cytoplasm, is dramatically altered. Most of the dorsal half of the spinal cord consists of small tightly packed cells with darkly staining nuclei and little cytoplasm. Moreover, there appears to be many more of these densely packed cells, leading to abnormal outgrowth of the dorsal CNS. In contrast, ventral development is normal, as are dorsal root ganglia, whose origins lie in neural cells derived from the dorsal spinal cord.

(vi) Ectopic Shh Expression Activates Floor Plate Gene Expression

To determine whether ectopic expression of chick Shh results in inappropriate activation of a ventral midline development in the dorsal CNS, expression of two floor plate expressed genes, HNF-3β and mouse Shh, were examined. Whole mounts of 9.5 dpc transgenic embryos show ectopic expression of HNF-3β throughout the cranial Wnt-1 expression domain. In addition to normal expression at the ventral midline, HNF-3β transcripts are expressed at high levels, in a circle just rostral to the mid/hindbrain junction, along the dorsal (actually lateral in unfused brain folds) aspects of the midbrain and, more weakly, in the roof plate of the myelencephalon. No expression is observed in the metencephalon which does not express Wnt-1. Thus, ectopic expression of Shh leads to the activation of HNF-3β throughout the cranial Wnt-1 expression domain.

The relationship between chick Shh expression and the expression of HNF-3β in serial sections was also examined. Activation of HNF-3β in the brain at 9.5 and 10.5 dpc is localized to the dorsal aspect in good agreement with the observed ectopic expression of chick Shh. Interestingly mouse Shh is also activated dorsally. Thus, two early floor plate markers are induced in response to chick Shh.

From 9.5 dpc to 11.5 dpc, the spinal cord phenotype becomes more severe. The possibility that activation of a floor plate pathway may play a role in the observed phenotype was investigated. In contrast to the brain, where ectopic HNF-3β and Shh transcripts are still present, little or no induction of these floor plate markers is observed. Thus, although the dorsal spinal cord shows a widespread transformation in cellular phenotype, this does not appear to result from the induction of floor plate development.

EXAMPLE 3

Chick Sonic Hedgehog Mediates ZPA Activity (i) Experimental Procedures

Retinoic Acid Bead Implants

Fertilized white Leghorn chicken eggs were incubated to stage 20 and then implanted with AG1-X2 ion exchange beads (Biorad) soaked in 1 mg/ml retinoic acid (RA, Sigma) as described by Tickle, C. et al., (1985) *Dev. Biol* 109: 82–95. Briefly, the beads were soaked for 15 min in 1 mg/ml RA in DMSO, washed twice and implanted under the AER on the anterior margin of the limb bud. After 24 or 36 hours, some of the implanted embryos were harvested and fixed overnight in 4% paraformaldehyde in PBS and then processed for whole mount in situ analysis as previously described. The remainder of the animals were allowed to develop to embryonic day 10 to confirm that the dose of RA used was capable of inducing mirror image duplications. Control animals were implanted with DMSO soaked beads and showed no abnormal phenotype or gene expression.

Plasmids

Unless otherwise noted, all standard cloning techniques were performed according to Ausubel, F. M. et al., (1989) *Current Protocols in Molecular Biology* N.Y.: Greene Publishing Assoc. and Wiley Inerscience), and all enzymes were obtained from Boehringer Mannheim Biochemicals. pHH-2 is a cDNA contain the entire coding region of chicken Sonic hedgehog (SEQ ID NO: 1). RCASBP(A) and RCASBP(E) are replication-competent retroviral vectors which encode viruses with differing host ranges. RCANBP(A) is a variant of RCASBP(A) from which the second splice acceptor has been removed. This results in a virus which can not express the inserted gene and acts as a control for the effects of viral infection (Hughes, S. H. et al., (1987) *J Virol.* 61: 3004–3012; Fekete, D. et al., (1993) *Mol. Cell. Biol.* 13: 2604–2613). RCASBP/AP(E) is version of RCASBP(E) containing a human placental alkaline phosphatase cDNA (Fekete, D. et al., (1993b) *Proc. Natl. Acad. Sci. USA* 90: 2350–2354). SLAX13 is a pBluescript SK+ derived plasmid with a second Cla I restriction site and the 5' untranslated region of v-src (from the adaptor plasmid CLA12-Nco, Hughes, S. H. et al., (1987) *J Virol.* 61: 3004–3012) cloned 5' of the EcoRI (and ClaI) site in the pBluescript polylinker. RCASBP plasmids encoding Sonic from either the first (MI) or second (M2) methionine (at position 4) were constructed by first shuttling the 1.7 kb Sonic fragment of pHH-2 into SLAX-13 using oligonucleotides to modify the 5' end of the cDNA such that either the first or second methionine is in frame with the NcoI site of SLAX-13. The amino acid sequence of Sonic is not mutated in these constructs. The M1 and M2 Sonic ClaI fragments (v-src 5' UTR:Sonic) were each then subcloned into RCASBP(A), RCANBP(A) and RCASBP(E), generating Sonic/RCAS-A1, Sonic/RCAS-A2, Sonic/RCAN-A1, Sonic/RCAN-A2, Sonic/RCAS-E1 and Sonic/RCAS-E2.

Chick Embryos, Cell Lines And Virus Production

All experimental manipulations were performed on standard specific-pathogen free White Leghorn chick embryos (S-SPF) from closed flocks provided fertilized by SPAFAS (Norwich, Conn.). Eggs were incubated at 37.5° C. and staged according to Hamburger, V. et al., (1951) *J Exp. Morph.* 88: 49–92. All chick embryo fibroblasts (CEF) were provided by C. Cepko. S-SPF embryos and CEFs have previously been shown to be susceptible to RCASBP(A) infection but resistant to RCASBP(E) infection (Fekete, D. et al., (1993b) *Proc. Natl. Acad. Sci. USA* 90: 2350–2354). Line 15b CEFs are susceptible to infection by both RCASBP (A) and (E). These viral host ranges were confirmed in control experiments. CEF cultures were grown and transfected with retroviral vector DNA as described (Morgan, B. A. et al., (1993) *Nature* 358: 236–239; Fekete, D. et al., (1993b) *Proc. Natl. Acad. Sci. USA* 90: 2350–2354). All viruses were harvested and concentrated as previously described (Morgan, B. A. et al., (1993) *Nature* 358: 236–239; Fekete, D. et al., (1993b) *Proc. Natl. Acad. Sci. USA* 90: 2350–2354) and had titres of approximately 108 cfu/ml.

Cell Implants

A single 60 mm dish containing line 15b CEFs which had been infected with either RCASBP/AP(E), Sonic/RCAS-E1 or Sonic/RCAS-E2 were grown to 50–90% confluence, lightly trypsinized and then spun at 1000 rpm for 5 min in a clinical centrifuge. The pellet was resuspended in 1 ml media, transferred to a microcentrifuge tube and then microcentrifuged for 2 min at 2000 rpm. Following a 30 min incubation at 37° C., the pellet was respun for 2 min at 2000 rpm and then lightly stained in media containing 0.01% nile blue sulfate. Pellet fragments of approximately 300 μm×50 μm were implanted as a wedge to the anterior region of hh stage 19–23 wing buds (as described by Riley, B. B. et al., (1993) *Development* 118: 95–104). At embryonic day 10, the embryos were harvested, fixed in 4% paraformaldehyde in PBS, stained with alcian green, and cleared in methyl salicylate (Tickle, C. et al., (1985) *Dev. Biol* 109: 82–95).

Viral Infections

Concentrated Sonic/RCAS-A2 or Sonic/RCAN-A2 was injected under the AER on the anterior margin of stage 20–22 wing buds. At 24 or 36 hours post-infection, the embryos were harvested, fixed in 4% paraformaldehyde in PBS and processed for whole mount in situ analysis as previously described.

(ii) Co-Localization Of Sonic Expression And Zpa Activity

ZPA activity has been carefully mapped both spatially and temporally within the limb bud (Honig, L. S. et al., (1985)

*J Embryol. exp. Morph.* 87: 163–174). In these experiments small blocks of limb bud tissue from various locations and stages of chick embryogenesis (Hamburger, V et al., (1951) *J Exp. Morph.* 88: 49–92) were grafted to the anterior of host limb buds and the strength of ZPA activity was quantified according to degrees of digit duplication. Activity is first weakly detected along the flank prior to limb bud outgrowth. The activity first reaches a maximal strength at stage 19 in the proximal posterior margin of the limb bud. By stage 23 the activity extends the full length of the posterior border of the limb bud. The activity then shifts distally along the posterior margin so that by stage 25 it is no longer detectable at the base of the flank. The activity then fades distally until it is last detected at stage 29.

This detailed map of endogenous polarizing activity provided the opportunity to determine the extent of the correlation between the spatial pattern of ZPA activity and Sonic expression over a range of developmental stages. Whole mount in situ hybridization was used to assay the spatial and temporal pattern of Sonic expression in the limb bud. Sonic expression is not detected until stage 17, at the initiation of limb bud formation, at which time it is weakly observed in a punctate pattern reflecting a patchy expression in a few cells. From that point onwards the Sonic expression pattern exactly matches the location of the ZPA, as determined by Honig. L. S. et al., (1985) *J EmbryoL exp. Morph.* 87: 163–174, both in position and in intensity of expression.

(iii) Induction Of Sonic Expression By Retinoic Acid

A source of retinoic acid placed at the anterior margin of the limb bud will induce ectopic tissue capable causing mirror-image duplications (Summerbell, D. et al., (1983) *In Limb Development and Regeneration* (N.Y.: Ala R. Liss) pp. 109–118; Wanek. N. et al., (1991) *Nature* 350: 81–83). The induction of this activity is not an immediate response to retinoic acid but rather takes approximately 18 hours to develop (Wanek, N. et al., (1991) *Nature* 350: 81–83). When it does develop, the polarizing activity is not found surrounding the implanted retinoic acid source, but rather is found distal to it in the mesenchyme along the margin of the limb bud (Wanek, N. et al., (1991) *Nature* 350: 81–83).

If Sonic expression is truly indicative of ZPA tissue, then it should be induced in the ZPA tissue which is ectopically induced by retinoic acid. To test this, retinoic acid-soaked beads were implanted in the anterior of limb buds and the expression of Sonic after various lengths of time using whole-mount in situ hybridization was assayed. As the limb bud grows, the bead remains imbedded proximally in tissue which begins to differentiate. Ectopic Sonic expression is first detected in the mesenchyme 24 hours after bead implantation. This expression is found a short distance from the distal edge of the bead. By 36 hours Sonic is strongly expressed distal to the bead in a stripe just under the anterior ectoderm in a mirror-image pattern relative to the endogenous Sonic expression in the posterior of the limb bud.

(iv) Effects Of Ectopic Expression Of Sonic On Limb Patterning

The normal expression pattern of Sonic, as well as that induced by retinoic acid, is consistent with Sonic being a signal produced by the ZPA. To determine whether Sonic expression is sufficient for ZPA activity, the gene was ectopically expressed within the limb bud. In most of the experiments we have utilized a variant of a replication-competent retroviral vector called RCAS (Hughes, S. H. et al., (1987) *J Virol.* 61: 3004–3012)) both as a vehicle to introduce the Sonic sequences into chick cells and to drive their expression. The fact that there exists subtypes of avian retroviruses which have host ranges restricted to particular strains of chickens was taken advantage of to control the region infected with the Sonic/RCAS virus (Weiss, R. (et al.) (1984) *RNA Tumor Viruses*, Vol. 1 Weiss et al. eds., (N.Y.: Cold Spring Harbor Laboratories) pp. 209–260); Fekete, D. et al., (1993a) *Mol. Cell. Biol.* 13: 2604–2613). Thus a vector with a type E envelope protein (RCAS-E, Fekete, D. et al., (1993b) *Proc. Natl Acad. Sci. USA* 90: 2350–2354) is unable to infect the cells of the SPAFAS outbred chick embryos routinely used in our lab. However, RCAS-E is able to infect cells from chick embryos of line 15b. In the majority of experiments, primary chick embryo fibroblasts (CEFs) prepared from line 15b embryos in vitro were infected. The infected cells were pelleted and implanted into a slit made in the anterior of S-SPF host limb buds. Due to the restricted host range of the vector, the infection was thus restricted to the graft and did not spread through the host limb bud.

To determine the fate of cells implanted and to control for any effect of the implant procedure, a control RCAS-E vector expressing human placental alkaline phosphatase was used. Alkaline phosphatase expression can be easily monitored histochemically and the location of infected cells can thus be conveniently followed at any stage. Within 24 hours following implantation the cells are dispersed proximally and distally within the anterior margin of the limb bud. Subsequently, cells are seen to disperse throughout the anterior portion of the limb and into the flank of the embryo.

Figure 10:
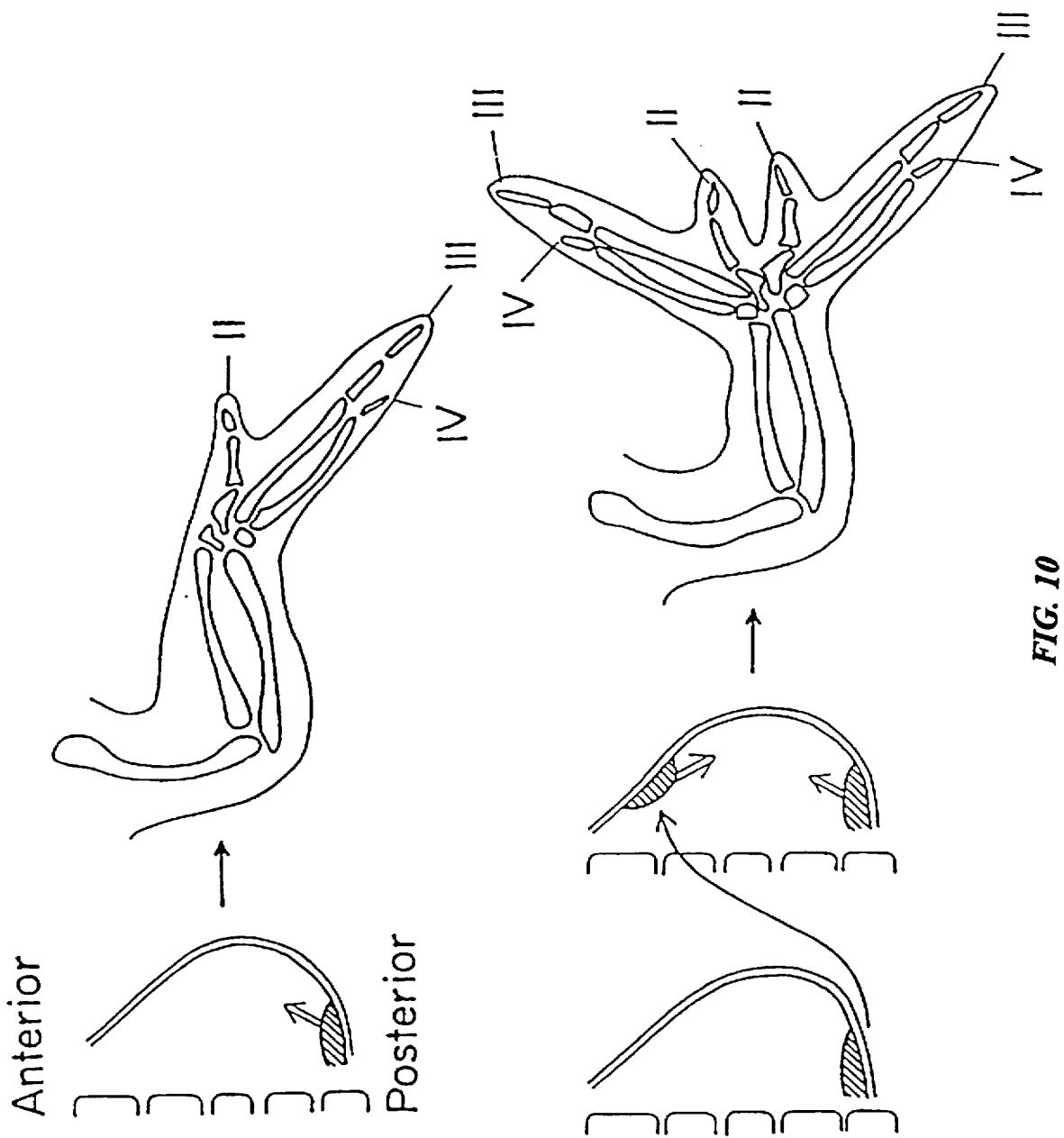
FIG. 10 is a model for anterioposterior limb patterning and the Zone of Polarizing Activity (ZPA), based on Saunders and Gasseling (1968). The left portion of the diagram schematizes a stage 20 limb bud. The somites are illustrated as blocks along the left margin of the limb bud; right portion of the same panel illustrates the mature wing. The hatched region on the posterior limb is the ZPA. Normally, the developed wing contains three digits II, III, and IV. The figure further shows the result of transplanting a ZPA from one limb bud to the anterior margin of another. The mature limb now contains six digits IV, III, II, II, III, and IV in a mirror-image duplication of the normal pattern. The large arrows in both panels represent the signal produced by the ZPA which acts to specify digit identity.

Limb buds grafted with alkaline phosphatase expressing cells or uninfected cells give rise to limbs with structures indistinguishable from unoperated wild type limbs. Such limbs have the characteristic anterior-to-posterior digit pattern 2-3-4. ZPA grafts give rise to a variety of patterns of digits depending on the placement of the graft within the bud (Tickle, C. et al., (1975) *Nature* 254: 199–202) and the amount of tissue engrafted (Tickle, C. (1981) *Nature* 289: 295–298). In some instances the result can be as weak as the duplication of a single digit 2. However, in optimal cases the ZPA graft evokes the production of a full mirror image duplication of digits 4-3-2-2-3-4 or 4-3-2-3-4 (see FIG. 10). A scoring system has been devised which rates the effectiveness of polarizing activity on the basis of the most posterior digit duplicated: any graft which leads to the development of a duplication of digit 4 has been defined as reflecting 100% polarizing activity (Honig, L. S. et al., (1985) *J EmbryoL Exp. Morph.* 87: 163–174).

Grafts of 15b fibroblasts expressing Sonic resulted in a range of ZPA-like phenotypes. In some instances the resultant limbs deviate from the wild type solely by the presence of a mirror-image duplication of digit 2. The most common digit phenotype resulting from grafting Sonic-infected CEF cells is a mirror-image duplication of digits 4 and 3 with digit 2 missing: 4-3-3-4. In many such cases the two central digits appear fused in a 4-3/3-4 pattern. In a number of the cases the grafts induced full mirror-image duplications of the digits equivalent to optimal ZPA grafts 4-3-3-2-3-4. Besides the digit duplications, the ectopic expression of Sonic also gave rise to occasional duplications of proximal elements including the radius or ulna, the humerus and the coracoid. While these proximal phenotypes are not features of ZPA grafts, they are consistent with an anterior-to-posterior respecification of cell fate. In some instances, most commonly when the radius or ulna was duplicated, more complex digit patterns were observed. Typically, an additional digit 3 was formed distal to a duplicated radius.

The mirror-image duplications caused by ZPA grafts are not limited to skeletal elements. For example, feather buds are normally present only along the posterior edge of the limb. Limbs exhibiting mirror-image duplications as a result of ectopic Sonic expression have feather buds on both their anterior and posterior edges, similar to those observed in ZPA grafts.

While ZPA grafts have a powerful ability to alter limb pattern when placed at the anterior margin of a limb bud, they have no effect when placed at the posterior margin (Saunders, J. W. et al., (1968) *Epithelial-Mesenchymal Interaction*, Fleischmayer and Billingham, eds. (Baltimore: Williams and Wilkins) pp. 78–97). Presumably, the lack of posterior effect is a result of polarizing activity already being present in that region of the bud. Consistent with this, grafts of Sonic expressing cells placed in the posterior of limb buds never result in changes in the number of digits. Some such grafts did produce distortions in the shape of limb elements, the most common being a slight posterior curvature in the distal tips of digits 3 and 4 when compared to wild type wings.

(v) Effect Of Ectopic Sonic Expression On Hoxd Gene Activity

The correct expression of Hoxd genes is part of the process by which specific skeletal elements are determined (Morgan, B. A. et al., (1993) *Nature* 358: 236–239). A transplant of a ZPA into the anterior of a chick limb bud ectopically activates sequential transcription of Hoxd genes in a pattern which mirrors the normal sequence of Hoxd gene expression (Nohno, T. et al., (1991) *Cell* 64: 1197–1205; Izpisua-Belmonte, J. C. et al., (1991) *Nature* 350: 585–589). Since ectopic Sonic expression leads to the same pattern duplications as a ZPA graft, we reasoned that Sonic would also lead to sequential activation of Hoxd genes.

To test this hypothesis, anterior buds were injected with Sonic/RCAS-A2, a virus which is capable of directly infecting the host strains of chicken embryos. This approach does not strictly limit the region expressing Sonic (being only moderately controlled by the timing, location and titer of viral injection), and thus might be expected to give a more variable result. However, experiments testing the kinetics of viral spread in infected limb buds indicate that infected cells remain localized near the anterior margin of the bud for at least 48 hours. Hoxd gene expression was monitored at various times post infection by whole mount in situ hybridization. As expected, these genes are activated in a mirror-image pattern relative their expression in the posterior of control limbs. For example, after 36 hours Hoxd-13 is expressed in a mirror-image symmetrical pattern in the broadened distal region of infected limb buds. Similar results were obtained with other Hoxd genes (manuscript in preparation).

EXAMPLE 4

A Functionally Conserved Homolog of Drosophila Hedgehog is Expressed in Tissues With Polarizing Activity in Zebrafish Embryos

(i) Experimental Procedures

Cloning and Sequencing

Approximately $1.5 \times 10^6$ plaques of a 33 h zebrafish embryonic λgt11 cDNA library were screened by plaque hybridization at low stringency (McGinnis, W. et al., (1984) *Nature* 308: 428–433) using a mix of two hh sequences as a probe: a Drosophila hh 400 bp EcoRi fragment and a murine Ihh 264 bp BamHI-EcoRI exon 2 fragment. Four clones were isolated and subcloned into the EcoRi sites of pUC18 T3T7 (Pharmacia). Both strands of clone 8.3 were sequenced using nested deletions (Pharmacia) and internal oligonucleotide primers. DNA sequences and derived amino acid sequences were analysed using "Geneworks" (Intelligenetics) and the GCG software packages.

PCR amplification

Degenerate oligonucleotides hh5.1 (SEQ ID NO: 30) and hh3.3 (SEQ ID NO: 31) were used to amplify genomic zebrafish DNA hh 5.1: AG(CA)GTTG(CT)AA(AG)GA(AG)(CA)(AG)I(GCT)IAA hh 3.3: CTCIACIGCIA(GA)ICK=(GT)IGCIA PCR was performed with an initial denaturation at 94° C. followed by 35 cycles of 47° C. for 1 min, 72° C. for 2 min and 94° C. for 1 min with a final extension at 72° C. Products were subcloned in pUC18 (Pharmacia).

In Situ Hybridization

In situ hybridizations of zebrafish embryos were performed as described in Oxtoby, E. et al., (1993) *Nuc. Acids Res.* 21: 1087–1095 with the following modifications: Embryos were rehydrated in ethanol rather than methanol series; the proteinase K digestion was reduced to 5 min and subsequent washes were done in PBTw without glycine; the antibody was preadsorbed in PBTw, 2 mg/ml BSA without sheep serum; and antibody incubation was performed in PBTw, 2 mg/ml BSA. Drosophila embryos were processed and hybridized as previously described.

Histology

Stained embryos were dehydrated through ethanol:butanol series, as previously described (Godsave, S. F. et al., (1988) *Development* 102: 555–566), and embedded in Fibrowax. 8 μm sections were cut on an Anglian rotary microtome.

RNA Probe Synthesis

For analysis of Shh expression, two different templates were used with consistent results; (i) phh[c] 8.3 linearized with Bgl II to transcribe an antisense RNA probe that excludes the conserved XXX region, and (ii) phh[c] 8.3 linearized with Hind III to transcribe an antisense RNA that covers the complete cDNA. All in situ hybridizations were performed with the latter probe which gives better signal. Other probes were as follows: Axial DraI-linearised p6T1N (Strahle, U. et al., (1993) *Genes & Dev.* 7: 1436–1446) using T3 RNA polymerase. gsc linearised with EcoR1 and transcribed with T7: pax 2 Bam HI-linearised pcF16 (Krauss, S. et al., (1991) *Development* 113: 1193–1206) using T7 RNA polymerase. In situ hybridizations were performed using labelled RNA at a concentration of 1 ng/ml final concentration. Antisense RNA probes were transcribed according to the manufacturer's protocol (DIG RNA Labelling Kit, BCL).

Zebrafish Strains

Wild type fish were bred from a founder poulation obtained from the Goldfish Bowl, Oxford. The mutant cyclops strain bl6 and the mutant notail strains bl60 and bl95 were obtained from Eugene, Oreg. Fish were reared at 28° C. on a 14 h light/10 h dark cycle.

RNA Injections

The open reading frame of Shh was amplified by PCR, using oligonucleotides 5'-CTGCAGGGATCCACCATGCGGCTTTTGACGAG-3' (SEQ ID NO: 32), which contains a consensus Kozak sequence for translation initiation, and 5'-CTGCAGGGATCCTTATTCCACACGAGGGATT-3' (SEQ ID NO: 33), and subcloned into the BglII site of pSP64T (Kreig, P. A. et al., (1984) *Nuc. Acids Res.* 12: 7057–7070). This vector includes 5' and 3' untranslated Xenopus β-Globin sequences for RNA stabilization and is commonly used for RNA injections experiments in Xenopus. In vitro transcribed Shh RNA at a concentration of approximately 100 µg/ml was injected into a single cell of naturally spawned zebrafish embryos at one-cell to 4-cell stages using a pressure-pulsed Narishige microinjector. The injected volume was within the picolitre range. Embryos were fixed 20 to 27 hrs after injection in BT-Fix (Westerfield, M. (1989) *The Zebrafish Book*, (Eugene: The University of Oregon Press)) and processed as described above for whole-mount in situ hybridizations with the axial probe.

Transgenic Drosophila

An EcoR1 fragment, containing the entire Shh ORF, was purified from the plasmid phh[c]8.3 and ligated with phosphatased EcoR1 digested transformation vector pCaSpeRhs (Thummel, C. S. et al., (1988) *Gene* 74: 445–456). The recombinant plasmid, pHS Shh containing the Shh ORF in the correct orientation relative to the heat shock promoter, was selected following restriction enzyme analysis of miniprep DNA from transformed colonies and used to transform Drosophila embryos using standard microinjection procedures (Roberts, D. B. (1986), *Drosophila, A Practical Approach*, Roberts, D. B., ed., (Oxford: IRL Press) pp. 1–38).

Ectopic Expression In Drosophila Embryos

Embryos carrying the appropriate transgenes were collected over 2 hr intervals, transferred to thin layers of 1% agarose on glass microscope slides and incubated in a plastic Petri dish floating in a water bath at 37° C. for 30 min intervals. Following heat treatment, embryos were returned to 25° C. prior to being fixed for in situ hybridization with DIG labelled single stranded Shh, wg or ptc RNA probes as previously described (Ingham et al., (1991) *Curr. Opin. Genet. Dev.* 1: 261–267).

(ii) Molecular Cloning Of Zebrafish Hedgehog Homologues

In an initial attempt to isolate sequences homologous to Drosophila hh, a zebrafish genomic DNA library was screened at reduced stringency with a partial cDNA, hhPCR4.1, corresponding to the first and second exons of the Drosophila gene (Mohler, J. et al., (1992) *Development* 115: 957–971). This screen proved unsuccessful; however, a similar screen of a mouse genomic library yielded a single clone with significant homology to hh., subsequently designated Ihh. A 264 bp BamHI-EcoRI fragment from this lambda clone containing sequences homologous to the second exon of the Drosophila gene was subcloned and, together with the Drosophila partial cDNA fragment, used to screen a λgt11 zebrafish cDNA library that was prepared from RNA extracted from 33 h old embryos. This screen yielded four clones with overlapping inserts the longest of which is 1.6 kb in length, herein referred to as Shh (SEQ ID NO: 9).

(iii) A Family Of Zebrafish Genes Homologous To The Drosophila Segment Polarity Gene, Hedgehog Alignment of the predicted amino acid sequences of Shh (SEQ ID NO: 10) and hh (SEQ ID NO: 11) revealed an identity of 47%, confirming that Shh is a homolog of the Drosophila gene. A striking conservation occurs within exon 2: an 80 amino acid long domain shows 72% identity between Shh and drosophila hh. (FIG. 11A). This domain is also highly conserved in all hh-related genes cloned so far and is therefore likely to be essential to the function of hh proteins. A second domain of approximately 30 amino acids close to the carboxy-terminal end, though it shows only 61% amino-acid identity, possesses 83% similarity between Shh and hh when allowing for conservative substitutions and could also, therefore, be of functional importance (FIG. 1B). Although putative sites of post-translational modification can be noted, their position is not conserved between Shh and hh.

Lee, J. J. et al., (1992) *Cell* 71: 33–50, identified a hydrophobic stretch of 21 amino acids flanked downstream by a putative site of signal sequence cleavage (predicted by the algorithm of von Heijne, G. (1986) *Nuc. Acids Res.* 11) close to the amino-terminal end of hh. Both the hydrophobic stretch and the putative signal sequence cleavage sites of hh, which suggest it to be a signaling molecule, are conserved in Shh. In contrast to hh, Shh does not extend N-terminally to the hydrophobic stretch.

Using degenerate oligonucleotides corresponding to amino-acids flanking the domain of high homology between Drosophila hh and mouse Ihh exons 2 described above, fragments of the expected size were amplified from zebrafish genomic DNA by PCR. After subcloning and sequencing, it appeared that three different sequences were amplified, all of which show high homology to one another and to Drosophila hh (FIG. 12). One of these corresponds to Shh therein referred to as 2-hh(a) SEQ ID NO: 16 and 2 hh(b) SEQ ID NO: 17, while the other two represent additional zebrafish hh homologs (SEQ ID NO: 9). cDNAs corresponding to one of these additional homologs have recently been isolated, confirming that it is transcribed. Therefore, Shh represents a member of a new vertebrate gene family.

(iv) Shh Expression In The Developing Zebrafish Embryo

Gastrula stages

Shh expression is first detected at around the 60% epiboly stage of embryogenesis in the dorsal mesoderm. Transcript is present in a triangular shaped area, corresponding to the embryonic shield, the equivalent of the amphibian organizer, and is restricted to the inner cell layer, the hypoblast. During gastrulation, presumptive mesodermal cells involute to form the hypoblast, and converge towards the future axis of the embryo, reaching the animal pole at approximately 70% epiboly. At this stage, Shh -expressing cells extend over the posterior third of the axis, and the signal intensity is not entirely homogeneous, appearing stronger at the base than at the apex of the elongating triangle of cells.

This early spatial distribution of Shh transcript is reminiscent of that previously described for axial, a forkhead-related gene; however, at 80% epiboly, axial expression extends further towards the animal pole of the embryo and we do not see Shh expression in the head area at these early developmental stages.

By 100% epiboly, at 9.5 hours of development, the posterior tip of the Shh expression domain now constitutes a continuous band of cells that extends into the head. To determine the precise anterior boundary of Shh expression, embryos were simultaneously hybridized with probes of Shh and pax-2 (previously pax[b]), the early expression domain of which marks the posterior midbrain (Krauss, S. et al. (1991) *Development* 113: 1193-1206). By this stage, the anterior boundary of the Shh expression domain is positioned in the centre of the animal pole and coincides approximately with that of axial. At the same stage, prechordal plate cells expressing the homeobox gene goosecoid (gsc) overlap and underly the presumptive forebrain (Statchel, S. E. et al., (1993) *Development* 117: 1261-1274). Whereas axial is also thought to be expressed in head mesodermal tissue at this stage, we cannot be certain whether Shh is expressed in the same cells. Sections of stained embryos suggest that in the head Shh may by this stage be expressed exclusively in neuroectodermal tissue.

(v) Somitogenesis

By the onset of somitogenesis (approximately 10.5 h of development), Shh expression in the head is clearly restricted to the ventral floor of the brain, extending from the tip of the diencephalon caudally through the hindbrain. At this stage, expression of axial has also disappeared from the head mesoderm and is similarly restricted to the floor of the brain; in contrast to Shh, however, it extends only as far as the anterior boundary of the midbrain. At this point, gsc expression has become very weak and is restricted to a ring of cells that appear to be migrating away from the dorsal midline.

As somitogenesis continues, Shh expression extends in a rostral-caudal progression throughout the ventral region of the central nervous system (CNS). Along the spinal cord, the expression domain is restricted to a single row of cells, the floor plate, but gradually broadens in the hindbrain and midbrain to become 5-7 cells in diameter, with a triangular shaped lateral extension in the ventral diencephalon and two strongly staining bulges at the tip of the forebrain, presumably in a region fated to become hypothalamus.

As induction of Shh in the floor plate occurs, expression in the underlying mesoderm begins to fade away, in a similar manner to axial (Strahle, U. et al., (1993) *Genes & Dev.* 7: 1436-1446). This downregulation also proceeds in a rostral to caudal sequence, coinciding with the changes in cell shape that accompany notochord differentiation. By the 22 somite stage, mesodermal Shh expression is restricted to the caudal region of the notochord and in the expanding tail bud where a bulge of undifferentiated cells continue to express Shh at relatively high levels. Expression in the midbrain broadens to a rhombic shaped area; cellular rearrangements that lead to the 90° kink of forebrain structures, position hypothalamic tissue underneath the ventral midbrain. These posterior hypothalamic tissues do not express Shh. In addition to Shh expression in the ventral midbrain, a narrow stripe of expressing cells extends dorsally on either side of the third ventricle from the rostral end of the Shh domain in the ventral midbrain to the anterior end of, but not including, the epiphysis. The most rostral Shh expressing cells are confined to the hypothalamus. In the telencephalon, additional Shh expression is initiated in two 1-2 cell wide stripes.

By 36 hours of development, Shh expression in the ventral CNS has undergone further changes. While expression persists in the floor plate of the tailbud, more rostrally located floor plate cells in the spinal cord cease to express the gene. In contrast, in the hindbrain and forebrain Shh expression persists and is further modified.

At 26-28 h, Shh expression appears in the pectoral fin primordia, that are visible as placode like broadenings of cells underneath the epithelial cell layer that covers the yolk. By 33 hrs of development high levels of transcript are present in the posterior margin of the pectoral buds; at the same time, expression is initiated in a narrow stripe at the posterior of the first gill. Expression continues in the pectoral fin buds in lateral cells in the early larva. At this stage, Shh transcripts are also detectable in cells adjacent to the lumen of the foregut.

(vi) Expression Of Shh In Cyclops And Notail Mutants

Two mutations affecting the differentiaton of the Axial tissues that express Shh have been described in zebrafish embryos homozygous for the cyclops (cyc) mutation lack a differentiated floorplate (Hatta, K. et al., (1991) *Nature* 350: 339-341). By contrast, homozygous notail (ntl) embryos are characterised by a failure in notochord maturation and a disruption of normal development of tail structures (Halpern, M. E. et al., (1993) *Cell* 75: 99-111).

A change in Shh expression is apparent in cyc embryos as early as the end of gastrulation; at this stage, the anterior limit of expression coincides precisely with the two pax-2 stripes in the posterior midbrain. Thus, in contrast to wild-type embryos, no Shh expression is detected in midline structures of the midbrain and forebrain. By the 5 somite stage, Shh transcripts are present in the notochord which at this stage extends until rhombomere 4; however, no expression is detected in more anterior structures. Furthermore, no Shh expression is detected in the ventral neural keel, in particular in the ventral portions of the midbrain and forebrain.

At 24 hours of development, the morphologically visible cyc phenotype consists of a fusion of the eyes at the midline due to the complete absence of the ventral diencephalon. As at earlier developmental stages, Shh expression is absent from neural tissue. Shh expression in the extending tail bud of wild-type embryos is seen as a single row of floor plate cells throughout the spinal cord. In a cyc mutant, no such Shh induction occurs in cells of the ventral spinal cord with the exception of some scattered cells that show transient expression near the tail. Similarly, no Shh expression is seen rostrally in the ventral neural tube. However, a small group of Shh expressing cells is detected underneath the epiphysis which presumably correspond to the dorsal-most group of Shh expressing cells in the diencephalon of wild-type embryos.

In homozygous notail (nt) embryos, no Shh staining is seen in mesodermal tissue at 24 hours of development, consistent with the lack of a notochord in these embryos; by contrast, expression throughout the ventral CNS is unaffected. At the tail bud stage, however, just prior to the onset of somitogenesis, Shh expression is clearly detectable in notochord precursor cells.

(vii) Injection Of Synthetic Shh Transcripts Into Zebrafish Embryos Induces Expression Of A Floor Plate Marker To investigate the activity of Shh in the developing embryo, an over-expression strategy, similar to that employed in the analysis of gene function in Xenopus, was adopted. Newly fertilized zebrafish eggs were injected with synthetic Shh RNA and were fixed 14 or 24 hours later. As an assay for possible changes in cell fate consequent upon the ectopic activity of Shh, we decided to analyse Axial expression, since this gene serves as a marker for cells in which Shh is normally expressed. A dramatic, though highly localised ectopic expression of Axial in a significant proportion (21/80) of the injected embryos fixed after 24 hours of development is observed. Affected embryos show a broadening of the Axial expression domain in the diencephalon and ectopic Axial expression in the midbrain; however, in no case has ectopic expression in the telencephalon or spinal cord been observed. Many of the injected embryos also showed disturbed forebrain structures, in particular smaller ventricles and poorly developed eyes. Amongst embryos fixed after 14 h, a similar proportion (8/42) exhibit the same broadening and dorsal extension of the Axial stripe in the diencephalon as well as a dorsal extension of Axial staining in the midbrain; again, no changes in Axial expression were observed caudal to the hindbrain with the exception of an increased number of expressing cells at the tip of the tail.

(viii) Overexpression Of Shh In Drosophila Embryos Activates The hh-Dependent Pathway In order to discover whether the high degree of structural homology between the Drosophila and zebrafish hh genes also extends to the functional level, an overexpression system was used to test the activity of Shh in flies. Expression of Drosophila hh driven by the HSP70 promoter results in the ectopic activation of both the normal targets of hh activity; the wg transcriptional domain expands to fill between one third to one half of each parasegment whereas ptc is ectopically activated in all cells except those expressing en (Ingham, P. W. (1993) Nature 366: 560–562). To compare the activities of the fly and fish genes, flies transgenic for a HS Shh construct were generated described above and subjected to the same heat shock regime as H Shh transgenic flies. HS Shh embryos fixed immediately after the second of two 30 min heat shocks exhibit ubiquitous transcription of the Shh cDNA. Similarly treated embryos were fixed 30 or 90 min after the second heat shock and assayed for wg or ptc transcription. Both genes were found to be ectopically activated in a similar manner to that seen in heat shocked H Shh embryos; thus, the zebrafish Shh gene can activate the same pathway as the endogenous hh gene.

EXAMPLE 5

Cloning and Expression of Human Hedgehog

Using the same degenerate PCR primers as employed in the cloning of chicken hedgehog homologs, namely vHH5O (SEQ ID NO: 18), vHH3O (SEQ ID NO: 19) and vHH3I (SEQ ID NO: 20) nucleic acid fragment was amplified from human genomic DNA prepared from peripheral blood lymphocytes. From a number of isolates, distinct sequences were cloned, each highly homologous to other vertebrate hedgehog proteins. PCR probes were subsequently generated using the sequence of the human genomic fragments made and used as a probe to screen an cDNA library prepared from a human abortus. Clones isolated from the cDNA in this manner are believed to include full length clones of human hedgehog homologs which, though not yet sequenced fully, represent a source of recombinant human hedgehog homologs.

All of the above-cited references and publications are hereby incorporated by reference.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

What is claimed is:

1. A recombinantly produced polypeptide comprising a hedgehog amino acid sequence which is at least 80 percent identical to a sequence selected from the group consisting of SEQ ID. NO. 2, SEQ ID. NO. 4, SEQ ID. NO. 6, SEQ ID. NO. 8, and SEQ ID. NO. 10, which hedgehog amino acid sequence (i) induces expression of a ptc gene (ii) regulates differentiation of neuronal cells, (iii) regulates survival of differentiated neuronal cells, (iv) regulates proliferation of chondrocytes, (v) regulates spermatogenesis, (vi) induces expression of a Hoxd gene, or (vii) functionally replaces drosopholia hedgehog in transgenic drosophila.

2. A recombinantly produced polypeptide comprising a hedgehog amino acid sequence at least 80 percent identical with a sequence selected from the group consisting of residues 27–189 of SEQ ID. NO. 2, residues 22–187 of SEQ ID NO. 4, residues 1–116 of SEQ ID NO. 6, residues 25–187 of SEQ ID. NO. 8, and residues 24–186 of SEQ ID. NO. 10 which hedgehog amino acid sequence (i) induces expression of a prc gene, (ii) regulates differentiation of neuronal cells, (iii) regulates survival of differentiated neuronal cells, (iv) regulates proliferation of chondrocytes, (v) regulates spermatogenesis, (vi) induces expression of a Hoxd gene, or (vii) functionally replaces drosopholia hedgehog in transgenic drosophila.

3. An isolated polypeptide comprising a hedgehog amino acid sequence of at least 150 amino acid residues encoded by a nucleic acid which hybridizes under highly stringent conditions to a sequence selected from the group consisting of SEQ ID. NO. 1, SEQ ID. NO 3, SEQ ID. NO 5, SEQ ID. NO. 7, and SEQ ID. NO. 9, which hedgehog amino acid sequence (i) induces expression of a prc gene, (ii) regulates differentiation of neuronal cells (iii) regulates survival of differentiated neuronal cells, (iv) regulates proliferation of chondrocytes, (v) regulates spermatogenesis, (vi) induces expression of a Hoxd gene, or (vii) functionally replaces drosopholia hedgehog in transgenic drosophila.

4. An isolated polypeptide comprising a hedgehog amino acid sequence at least 80 percent identical to a sequence selected from the group consisting of SEQ ID. NO. 2, SEQ ID. NO. 4, SEQ ID. NO. 6, SEQ ID. NO. 8, and SEQ ID. NO. 10, which hedgehog amino acid sequence (i) induces expression of a ptc gene, (ii) regulates differentiation of neuronal cells, (iii) regulates survival of differentiated neuronal cells, (iv) regulates proliferation of chondrocytes (v) regulates spermatogenesis, (vi) induces expression of a Hoxd gene, or (vii) functionally replaces drosopholia hedgehog in transgenic drosophila.

5. A recombinantly produced polypeptide comprising a hedgehog amino acid sequence of at least 150 amino acid residues encoded by a nucleic acid which hybridizes under highly stringent conditions to a sequence selected from the group consisting of SEQ ID. NO. 1, SEQ ID. NO. 3, SEQ ID. NO. 5, SEQ ID. NO 7, and SEQ ID. NO. 9, which hedgehog amino acid sequence (i) induces expression of a pct genes (ii) regulates differentiation of neuronal cells (iii) regulates survival of differentiated neuronal cells, (iv) regulates proliferation of chondrocytes, (v) regulates spermatogenesis, (vi) induces expression of a Hoxd gene, or (vii) functionally replaces drosopholia hedgehog in transgenic drosophila.

6. An isolated polypeptide comprising a hedgehog amino acid sequence including an N-terminal portion of a mature hedgehog protein, said hedgehog amino acid sequence encoded by a nucleic acid which hybridizes under highly stringent conditions to a sequence selected from the group consisting of SEQ ID. NO. 1, SEQ ID. NO. 3, SEQ ID. NO. 5, SEQ ID. NO. 7, and SEQ ID. NO 9.

7. A recombinantly produced polypeptide comprising a hedgehog amino acid sequence including an N-terminal portion of a mature hedgehog protein, said hedgehog amino acid sequence encoded by a nucleic acid which hybridizes under highly stringent conditions to a sequence selected from the group consisting of SEQ ID. NO 1, SEQ ID. NO. 3, SEQ ID NO. 5, SEQ ID. NO. 7, and SEQ ID. NO. 10.

8. An isolated hedgehog polypeptide encoded by a hedgehog gene of a vertebrate organism.

9. The polypeptide of any of claims 3, 4, 5, 6 or 7, wherein said hedgehog amino acid sequence is at least 90 percent identical with a sequence selected from the group consisting SEQ ID. NO. 2, SEQ ID. NO. 4, SEQ ID. NO. 6, SEQ ID. NO. 8, and SEQ ID. NO. 10.

10. The polypeptide of claims 6 or 7, comprising an amino acid sequence encoded by a nucleic acid which hybridizes under stringent conditions to a sequence selected from the group consisting of residues 64–567 of SEQ ID. NO. 1, residues 64–561 of SEQ ID. NO. 3, residues 1–348 of SEQ ID NO. 5, residues 73–561 of SEQ ID NO. 7, and residues 70–558 of SEQ ID NO: 10.

11. An isolated hedgehog polypeptide having at least one biological activity of a vertebrate hedgehog protein, said polypeptide comprising an amino acid sequence at least 80 percent identical with a sequence selected from the group consisting of residues 27–189 of SEQ ID. NO. 2, residues 22–187 of SEQ ID. NO. 4, residues 1–116 of SEQ ID. NO. 6, residues 25–187 of SEQ ID. NO. 8, and residues 24–186 of SEQ ID. NO. 10.

12. The polypeptide of any of claims 2 or 11, wherein said polypeptide includes a hedgehog amino acid sequence at least 90 percent identical with a sequence selected from the group consisting of residues 27–189 of SEQ ID. NO. 2, residues 22–187 of SEQ ID. NO. 4, residues 1–116 of SEQ ID. NO. 6, residues 25–187 of SEQ ID. NO. 8, and residues 24–186 of SEQ ID. NO. 10.

13. The polypeptide of claim 12, wherein said polypeptide includes a hedgehog amino acid sequence at least 95 percent identical with a sequence selected from the group consisting of residues 27–189 of SEQ ID. NO. 2, residues 22–187 of SEQ ID. NO. 4, residues 1–116 of SEQ ID. NO. 6, residues 25–187 of SEQ ID. NO. 8, and residues 24–186 of SEQ ID. NO. 10.

14. The polypeptide of claim 12, wherein said polypeptide includes a hedgehog amino acid sequence identical to a sequence selected from the group consisting of residues 27–189 of SEQ ID. NO. 2, residues 22–187 of SEQ ID. NO. 4, residues 1–116 of SEQ ID. NO. 6, residues 25–187 of SEQ ID. NO.8, and residues 24–186 of SEQ ID. NO. 10.

15. An isolated hedgehog polypeptide comprising an amino acid sequence is encoded by at least a portion of a hedgehog gene of vertebrate origin comprising residues 64–561 of SEQ ID. NO. 3, residues 1–348 of SEQ ID. NO. 5 and residues 73–561 of SEQ ID NO. 7.

16. The polypeptide of any of claims 2, 4, or 11, wherein the hedgehog amino acid sequence is encoded by a nucleic acid which hybridizes under highly stringent conditions to a sequence selected from the group consisting of SEQ ID. NO. 1, SEQ ID. NO. 3, SEQ ID. NO. 5, SEQ ID. NO. 7, and SEQ ID. NO. 9.

17. The polypeptide of claim 6 or 9, wherein the hedgehog gene is a mammalian hedgehog gene.

18. The polypeptide of claim 9, wherein said hedgehog amino acid sequence is at least 95 percent identical with a sequence selected from the group consisting SEQ ID. NO. 2, SEQ ID. NO. 4, SEQ ID. NO. 6, SEQ ID. NO. 8, and SEQ ID. NO. 10.

19. The polypeptide of any of claims 3, 5, 6 or 7, wherein said hedgehog amino acid sequence is identical to a sequence selected from the group consisting SEQ ID. NO. 2, SEQ ID. NO. 4, SEQ ID. NO. 6, SEQ ID. NO. 8, and SEQ ID. NO. 10.

20. The polypeptide of claims 3 or 5, encoded by a nucleic acid which hybridizes under highly stringent conditions to a sequence selected from the group consisting of SEQ ID. NO. 3, SEQ ID. NO. 5 and SEQ ID. NO. 7.

21. The polypeptide of any of claims 3 or 5, wherein said hedgehog amino acid sequence comprising an N-terminal portion of a mature vertebrate hedgehog protein selected from the group consisting of SEQ ID. NO. 2, SEQ ID. NO. 4, SEQ ID NO. 6, SEQ ID NO. 8, and SEQ ID. NO. 10.

22. An hedgehog protein represented in SEQ ID. NO. 2, SEQ ID. NO. 4, SEQ ID. NO. 6, SEQ ID. NO. 8, and SEQ ID. NO. 10.

23. The polypeptide of any of claims 1, 2, 3, 4 or 15, which polypeptide is a fusion protein.

24. The polypeptide of any of claims 1, 2, 3, 4, 5, 6, 7, 8, 11, or 15 which polypeptide is postranslationally modified.

25. The polypeptide of claim 24, which polypeptide is glycosylated.

26. The polypeptide of any of claims 1, 2, 3, 4, 5, 6, 7, 8, 11, or 15, wherein the polypeptide promotes differentiation of neuronal cells or survival of differentiated neuronal cells.

27. The polypeptide of claim 26, wherein the neuronal cell is a dopaminergic neuron.

28. The polypeptide of claim 27, wherein the neuronal cell is a motorneuron.

29. The polypeptide of any of claims 1, 2, 3, 4, 5, 6, 7, 8, 11, or 15, wherein the polypeptide regulates proliferation of chondrocytes.

30. The polypeptide of any of claims 1, 2, 3, 4, 5, 6, 7, 8, 11, or 15, wherein the polypeptide regulates spermatogenesis.

31. The polypeptide of any of claims 1, 2, 3, 4, 5, 6, 7, 8, 11, or 15, wherein the polypeptide induces expression of a Hoxd gene.

32. The polypeptide of any of claims 1, 2, 3, 4, 5, 6, 7, 8, 11, or 15, wherein the polypeptide induces expression of a ptc gene.

33. The polypeptide of any of claims 1, 2, 3, 4, 5, 6, 7, 8, 11, or 15, which polypeptide ectopically replaces drosopholia hedgehog in a transgenic drosophila fly.

34. The polypeptide of any of claims 3, 4, 5, 8 or 11, wherein the polypeptide is purified to at least 80% by dry weight.

35. The polypeptide of claim 34, wherein the polypeptide is purified to at least 95% by dry weight.

* * * * *

UNITED STATES PATENT AND TRADEMARK OFFICE
CERTIFICATE OF CORRECTION

PATENT NO. : 5,789,543

DATED : August 4, 1998

INVENTOR(S) : Ingham, et al

It is certified that error appears in the above-identified patent and that said Letters Patent is hereby corrected as shown below:

On the Title Page, add Item [73] Assignee: --- Imperial Cancer Research Technology Ltd. ----.

Signed and Sealed this

Third Day of April, 2001

Attest:

NICHOLAS P. GODICI

Attesting Officer    *Acting Director of the United States Patent and Trademark Office*

UNITED STATES PATENT AND TRADEMARK OFFICE
CERTIFICATE OF CORRECTION

PATENT NO. : 5,789,543
DATED : August 4, 1998
INVENTOR(S) : Philip W. Ingham, Andrew P. McMahon, and Clifford J. Tabin It is certified that error appears in the above-identified patent and that said Letters Patent is hereby corrected as shown below:

Column 97,
Line 16, "gene" should read -- gene, --.
Lines 21, 33, 46, and 56, "drosopholia" should read -- drosophila --.
Line 24, "with" should read -- to --.
Lines 29 and 41, "prc" should read -- ptc --.
Lines 42, and 65, "cells" should read -- cells, --.
Line 44, "spermatogenesis." should read -- spermatogenesis, --
Line 54, "chondrocytes" should read -- chondrocytes, --.
Line 65, "pct genes" should read -- ptc gene, --.

Column 98
Line 12, "drosopholia" should read -- drosophila --.
Line 16, and 23, "encoded" should read -- being encoded --.
Lines 31, 43, 50, and 57, "with" should read -- to --.

Column 99,
Line 2, "is" should be deleted.
Line 29, "comprising" should read -- comprises --.

Column 100,
Line 13, "motorneuron" should read -- motor neuron --.
Lines 27-28, "drosopholia" should read -- drosophila --.

Signed and Sealed this

First Day of January, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 1277 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..1277

( x i ) SEQUENCE DESCRIPTION: SEQ ID NO:1:

```
ATG  GTC  GAA  ATG  CTG  CTG  TTG  ACA  AGA  ATT  CTC  TTG  GTG  GGC  TTC  ATC        48
Met  Val  Glu  Met  Leu  Leu  Leu  Thr  Arg  Ile  Leu  Leu  Val  Gly  Phe  Ile
 1                 5                              10                    15

TGC  GCT  CTT  TTA  GTC  TCC  TCT  GGG  CTG  ACT  TGT  GGA  CCA  GGC  AGG  GGC        96
Cys  Ala  Leu  Leu  Val  Ser  Ser  Gly  Leu  Thr  Cys  Gly  Pro  Gly  Arg  Gly
                  20                             25                    30
```

| | | | | | | | | | | | | | | | | |
|---|---|---|---|---|---|---|---|---|---|---|---|---|---|---|---|---|
| ATT | GGA | AAA | AGG | AGG | CAC | CCC | AAA | AAG | CTG | ACC | CCG | TTA | GCC | TAT | AAG | 144 |
| Ile | Gly | Lys 35 | Arg | Arg | His | Pro | Lys 40 | Lys | Leu | Thr | Pro | Leu 45 | Ala | Tyr | Lys | |
| CAG | TTT | ATT | CCC | AAT | GTG | GCA | GAG | AAG | ACC | CTA | GGG | GCC | AGT | GGA | AGA | 192 |
| Gln | Phe 50 | Ile | Pro | Asn | Val 55 | Ala | Glu | Lys | Thr | Leu 60 | Gly | Ala | Ser | Gly | Arg | |
| TAT | GAA | GGG | AAG | ATC | ACA | AGA | AAC | TCC | GAG | AGA | TTT | AAA | GAA | CTA | ACC | 240 |
| Tyr 65 | Glu | Gly | Lys | Ile | Thr 70 | Arg | Asn | Ser | Glu | Arg 75 | Phe | Lys | Glu | Leu | Thr 80 | |
| CCA | AAT | TAC | AAC | CCT | GAC | ATT | ATT | TTT | AAG | GAT | GAA | GAG | AAC | ACG | GGA | 288 |
| Pro | Asn | Tyr | Asn | Pro 85 | Asp | Ile | Ile | Phe | Lys 90 | Asp | Glu | Glu | Asn | Thr 95 | Gly | |
| GCT | GAC | AGA | CTG | ATG | ACT | CAG | CGC | TGC | AAG | GAC | AAG | CTG | AAT | GCC | CTG | 336 |
| Ala | Asp | Arg | Leu 100 | Met | Thr | Gln | Arg | Cys 105 | Lys | Asp | Lys | Leu | Asn 110 | Ala | Leu | |
| GCG | ATC | TCG | GTG | ATG | AAC | CAG | TGG | CCC | GGG | GTG | AAG | CTG | CGG | GTG | ACC | 384 |
| Ala | Ile | Ser 115 | Val | Met | Asn | Gln | Trp 120 | Pro | Gly | Val | Lys | Leu 125 | Arg | Val | Thr | |
| GAG | GGC | TGG | GAC | GAG | GAT | GGC | CAT | CAC | TCC | GAG | GAA | TCG | CTG | CAC | TAC | 432 |
| Glu | Gly | Trp 130 | Asp | Glu | Asp | Gly | His 135 | His | Ser | Glu | Glu | Ser 140 | Leu | His | Tyr | |
| GAG | GGT | CGC | GCC | GTG | GAC | ATC | ACC | ACG | TCG | GAT | CGG | GAC | CGC | AGC | AAG | 480 |
| Glu 145 | Gly | Arg | Ala | Val | Asp 150 | Ile | Thr | Thr | Ser | Asp 155 | Arg | Asp | Arg | Ser | Lys 160 | |
| TAC | GGA | ATG | CTG | GCC | CGC | CTC | GCC | GTC | GAG | GCC | GGC | TTC | GAC | TGG | GTC | 528 |
| Tyr | Gly | Met | Leu | Ala 165 | Arg | Leu | Ala | Val | Glu 170 | Ala | Gly | Phe | Asp | Trp 175 | Val | |
| TAC | TAC | GAG | TCC | AAG | GCG | CAC | ATC | CAC | TGC | TCC | GTC | AAA | GCA | GAA | AAC | 576 |
| Tyr | Tyr | Glu | Ser 180 | Lys | Ala | His | Ile | His 185 | Cys | Ser | Val | Lys | Ala 190 | Glu | Asn | |
| TCA | GTG | GCA | GCG | AAA | TCA | GGA | GGC | TGC | TTC | CCT | GGC | TCA | GCC | ACA | GTG | 624 |
| Ser | Val | Ala 195 | Ala | Lys | Ser | Gly | Gly 200 | Cys | Phe | Pro | Gly | Ser 205 | Ala | Thr | Val | |
| CAC | CTG | GAG | CAT | GGA | GGC | ACC | AAG | CTG | GTG | AAG | GAC | CTG | AGC | CCT | GGG | 672 |
| His | Leu | Glu 210 | His | Gly | Gly | Thr | Lys 215 | Leu | Val | Lys | Asp | Leu 220 | Ser | Pro | Gly | |
| GAC | CGC | GTG | CTG | GCT | GCT | GAC | GCG | GAC | GGC | CGG | CTG | CTC | TAC | AGT | GAC | 720 |
| Asp 225 | Arg | Val | Leu | Ala | Ala 230 | Asp | Ala | Asp | Gly | Arg 235 | Leu | Leu | Tyr | Ser | Asp 240 | |
| TTC | CTC | ACC | TTC | CTC | GAC | CGG | ATG | GAC | AGC | TCC | CGA | AAG | CTC | TTC | TAC | 768 |
| Phe | Leu | Thr | Phe | Leu 245 | Asp | Arg | Met | Asp | Ser 250 | Ser | Arg | Lys | Leu | Phe 255 | Tyr | |
| GTC | ATC | GAG | ACG | CGG | CAG | CCC | CGG | GCC | CGG | CTG | CTA | CTG | ACG | GCG | GCC | 816 |
| Val | Ile | Glu | Thr | Arg 260 | Gln | Pro | Arg | Ala | Arg 265 | Leu | Leu | Leu | Thr 270 | Ala | Ala | |
| CAC | CTG | CTC | TTT | GTG | GCC | CCC | CAG | CAC | AAC | CAG | TCG | GAG | GCC | ACA | GGG | 864 |
| His | Leu | Leu 275 | Phe | Val | Ala | Pro | Gln 280 | His | Asn | Gln | Ser | Glu 285 | Ala | Thr | Gly | |
| TCC | ACC | AGT | GGC | CAG | GCG | CTC | TTC | GCC | AGC | AAC | GTG | AAG | CCT | GGC | CAA | 912 |
| Ser | Thr | Ser 290 | Gly | Gln | Ala | Leu | Phe 295 | Ala | Ser | Asn | Val | Lys 300 | Pro | Gly | Gln | |
| CGT | GTC | TAT | GTG | CTG | GGC | GAG | GGC | GGG | CAG | CAG | CTG | CTG | CCG | GCG | TCT | 960 |
| Arg 305 | Val | Tyr | Val | Leu | Gly 310 | Glu | Gly | Gly | Gln | Gln 315 | Leu | Leu | Pro | Ala | Ser 320 | |
| GTC | CAC | AGC | GTC | TCA | TTG | CGG | GAG | GAG | GCG | TCC | GGA | GCC | TAC | GCC | CCA | 1008 |
| Val | His | Ser | Val | Ser 325 | Leu | Arg | Glu | Glu | Ala 330 | Ser | Gly | Ala | Tyr | Ala 335 | Pro | |
| CTC | ACC | GCC | CAG | GGC | ACC | ATC | CTC | ATC | AAC | CGG | GTG | TTG | GCC | TCC | TGC | 1056 |
| Leu | Thr | Ala | Gln 340 | Gly | Thr | Ile | Leu | Ile 345 | Asn | Arg | Val | Leu | Ala 350 | Ser | Cys | |

| | | | | | | | | | | | | | | | | |
|---|---|---|---|---|---|---|---|---|---|---|---|---|---|---|---|---|
| TAC | GCC | GTC | ATC | GAG | GAG | CAC | AGT | TGG | GCC | CAT | TGG | GCC | TTC | GCA | CCA | 1104 |
| Tyr | Ala | Val | Ile | Glu | Glu | His | Ser | Trp | Ala | His | Trp | Ala | Phe | Ala | Pro | |
| | | 355 | | | | 360 | | | | | 365 | | | | | |
| TTC | CGC | TTG | GCT | CAG | GGG | CTG | CTG | GCC | GCC | CTC | TGC | CCA | GAT | GGG | GCC | 1152 |
| Phe | Arg | Leu | Ala | Gln | Gly | Leu | Leu | Ala | Ala | Leu | Cys | Pro | Asp | Gly | Ala | |
| | 370 | | | | 375 | | | | | 380 | | | | | | |
| ATC | CCT | ACT | GCC | GCC | ACC | ACC | ACC | ACT | GGC | ATC | CAT | TGG | TAC | TCA | CGG | 1200 |
| Ile | Pro | Thr | Ala | Ala | Thr | Thr | Thr | Thr | Gly | Ile | His | Trp | Tyr | Ser | Arg | |
| 385 | | | | | 390 | | | | | 395 | | | | | 400 | |
| CTC | CTC | TAC | CGC | ATC | GGC | AGC | TGG | GTG | CTG | GAT | GGT | GAC | GCG | CTG | CAT | 1248 |
| Leu | Leu | Tyr | Arg | Ile | Gly | Ser | Trp | Val | Leu | Asp | Gly | Asp | Ala | Leu | His | |
| | | | | 405 | | | | | 410 | | | | | 415 | | |
| CCG | CTG | GGC | ATG | GTG | GCA | CCG | GCC | AGC | TG | | | | | | | 1277 |
| Pro | Leu | Gly | Met | Val | Ala | Pro | Ala | Ser | | | | | | | | |
| | | | 420 | | | | | 425 | | | | | | | | |

( 2 ) INFORMATION FOR SEQ ID NO:2:

( i ) SEQUENCE CHARACTERISTICS:
        ( A ) LENGTH: 425 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Val | Glu | Met | Leu | Leu | Leu | Thr | Arg | Ile | Leu | Leu | Val | Gly | Phe | Ile |
| 1 | | | | 5 | | | | | 10 | | | | | 15 | |
| Cys | Ala | Leu | Leu | Val | Ser | Ser | Gly | Leu | Thr | Cys | Gly | Pro | Gly | Arg | Gly |
| | | | 20 | | | | | 25 | | | | | 30 | | |
| Ile | Gly | Lys | Arg | Arg | His | Pro | Lys | Lys | Leu | Thr | Pro | Leu | Ala | Tyr | Lys |
| | | 35 | | | | | 40 | | | | | 45 | | | |
| Gln | Phe | Ile | Pro | Asn | Val | Ala | Glu | Lys | Thr | Leu | Gly | Ala | Ser | Gly | Arg |
| | 50 | | | | | 55 | | | | | 60 | | | | |
| Tyr | Glu | Gly | Lys | Ile | Thr | Arg | Asn | Ser | Glu | Arg | Phe | Lys | Glu | Leu | Thr |
| 65 | | | | 70 | | | | | 75 | | | | | 80 | |
| Pro | Asn | Tyr | Asn | Pro | Asp | Ile | Ile | Phe | Lys | Asp | Glu | Glu | Asn | Thr | Gly |
| | | | | 85 | | | | | 90 | | | | | 95 | |
| Ala | Asp | Arg | Leu | Met | Thr | Gln | Arg | Cys | Lys | Asp | Lys | Leu | Asn | Ala | Leu |
| | | | 100 | | | | | 105 | | | | | 110 | | |
| Ala | Ile | Ser | Val | Met | Asn | Gln | Trp | Pro | Gly | Val | Lys | Leu | Arg | Val | Thr |
| | | 115 | | | | | 120 | | | | | 125 | | | |
| Glu | Gly | Trp | Asp | Glu | Asp | Gly | His | His | Ser | Glu | Glu | Ser | Leu | His | Tyr |
| | 130 | | | | | 135 | | | | | 140 | | | | |
| Glu | Gly | Arg | Ala | Val | Asp | Ile | Thr | Thr | Ser | Asp | Arg | Asp | Arg | Ser | Lys |
| 145 | | | | | 150 | | | | | 155 | | | | | 160 |
| Tyr | Gly | Met | Leu | Ala | Arg | Leu | Ala | Val | Glu | Ala | Gly | Phe | Asp | Trp | Val |
| | | | | 165 | | | | | 170 | | | | | 175 | |
| Tyr | Tyr | Glu | Ser | Lys | Ala | His | Ile | His | Cys | Ser | Val | Lys | Ala | Glu | Asn |
| | | | 180 | | | | | 185 | | | | | 190 | | |
| Ser | Val | Ala | Ala | Lys | Ser | Gly | Gly | Cys | Phe | Pro | Gly | Ser | Ala | Thr | Val |
| | | 195 | | | | | 200 | | | | | 205 | | | |
| His | Leu | Glu | His | Gly | Gly | Thr | Lys | Leu | Val | Lys | Asp | Leu | Ser | Pro | Gly |
| | 210 | | | | | 215 | | | | | 220 | | | | |
| Asp | Arg | Val | Leu | Ala | Ala | Asp | Ala | Asp | Gly | Arg | Leu | Leu | Tyr | Ser | Asp |
| 225 | | | | | 230 | | | | | 235 | | | | | 240 |
| Phe | Leu | Thr | Phe | Leu | Asp | Arg | Met | Asp | Ser | Ser | Arg | Lys | Leu | Phe | Tyr |
| | | | | 245 | | | | | 250 | | | | | 255 | |

| | | | | | | | | | | | | | | | |
|---|---|---|---|---|---|---|---|---|---|---|---|---|---|---|---|
| Val | Ile | Glu | Thr 260 | Arg | Gln | Pro | Arg | Ala 265 | Arg | Leu | Leu | Leu 270 | Thr | Ala | Ala |
| His | Leu | Leu 275 | Phe | Val | Ala | Pro | Gln 280 | His | Asn | Gln | Ser | Glu 285 | Ala | Thr | Gly |
| Ser | Thr 290 | Ser | Gly | Gln | Ala 295 | Leu | Phe | Ala | Ser | Asn 300 | Val | Lys | Pro | Gly | Gln |
| Arg 305 | Val | Tyr | Val | Leu | Gly 310 | Glu | Gly | Gly | Gln 315 | Gln | Leu | Leu | Pro | Ala | Ser 320 |
| Val | His | Ser | Val | Ser 325 | Leu | Arg | Glu | Glu | Ala 330 | Ser | Gly | Ala | Tyr 335 | Ala | Pro |
| Leu | Thr | Ala | Gln 340 | Gly | Thr | Ile | Leu | Ile 345 | Asn | Arg | Val | Leu | Ala 350 | Ser | Cys |
| Tyr | Ala | Val 355 | Ile | Glu | Glu | His | Ser 360 | Trp | Ala | His | Trp | Ala 365 | Phe | Ala | Pro |
| Phe | Arg 370 | Leu | Ala | Gln | Gly | Leu 375 | Leu | Ala | Ala | Leu | Cys 380 | Pro | Asp | Gly | Ala |
| Ile 385 | Pro | Thr | Ala | Ala | Thr 390 | Thr | Thr | Thr | Gly | Ile 395 | His | Trp | Tyr | Ser | Arg 400 |
| Leu | Leu | Tyr | Arg | Ile 405 | Gly | Ser | Trp | Val | Leu 410 | Asp | Gly | Asp | Ala | Leu 415 | His |
| Pro | Leu | Gly | Met 420 | Val | Ala | Pro | Ala | Ser 425 | | | | | | | |

(2) INFORMATION FOR SEQ ID NO:3:

(i) SEQUENCE CHARACTERISTICS:
        (A) LENGTH: 1190 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1191

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GCT | CTG | CCG | GCC | AGT | CTG | TTG | CCC | CTG | TGC | TGC | TTG | GCA | CTC | TTG | 48 |
| Met 1 | Ala | Leu | Pro | Ala 5 | Ser | Leu | Leu | Pro | Leu 10 | Cys | Cys | Leu | Ala | Leu 15 | Leu | |
| GCA | CTA | TCT | GCC | CAG | AGC | TGC | GGG | CCG | GGC | CGA | GGA | CCG | GTT | GGC | CGG | 96 |
| Ala | Leu | Ser | Ala 20 | Gln | Ser | Cys | Gly | Pro 25 | Gly | Arg | Gly | Pro | Val 30 | Gly | Arg | |
| CGG | CGT | TAT | GTG | CGC | AAG | CAA | CTT | GTG | CCT | CTG | CTA | TAC | AAG | CAG | TTT | 144 |
| Arg | Arg | Tyr 35 | Val | Arg | Lys | Gln | Leu 40 | Val | Pro | Leu | Leu | Tyr 45 | Lys | Gln | Phe | |
| GTG | CCC | AGT | ATG | CCC | GAG | CGG | ACC | CTG | GGC | GCG | AGT | GGG | CCA | GCG | GAG | 192 |
| Val | Pro | Ser 50 | Met | Pro | Glu | Arg | Thr 55 | Leu | Gly | Ala | Ser | Gly 60 | Pro | Ala | Glu | |
| GGG | AGG | GTA | ACA | AGG | GGG | TCG | GAG | CGC | TTC | CGG | GAC | CTC | GTA | CCC | AAC | 240 |
| Gly | Arg 65 | Val | Thr | Arg | Gly | Ser 70 | Glu | Arg | Phe | Arg | Asp 75 | Leu | Val | Pro | Asn 80 | |
| TAC | AAC | CCC | GAC | ATA | ATC | TTC | AAG | GAT | GAG | GAG | AAC | AGC | GGC | GCA | GAC | 288 |
| Tyr | Asn | Pro | Asp | Ile 85 | Ile | Phe | Lys | Asp | Glu 90 | Glu | Asn | Ser | Gly | Ala 95 | Asp | |
| CGC | CTG | ATG | ACA | GAG | CGT | TGC | AAA | GAG | CGG | GTG | AAC | GCT | CTA | GCC | ATC | 336 |
| Arg | Leu | Met | Thr 100 | Glu | Arg | Cys | Lys | Glu 105 | Arg | Val | Asn | Ala | Leu 110 | Ala | Ile | |
| GCG | GTG | ATG | AAC | ATG | TGG | CCC | GGA | GTA | CGC | CTA | CGT | GTG | ACT | GAA | GGC | 384 |

-continued

| | | | | Ala | Val | Met | Asn | Met | Trp | Pro | Gly | Val | Arg | Leu | Arg | Val | Thr | Glu | Gly | |
| | | | | | | 115 | | | | 120 | | | | | | 125 | | | | |
| TGG | GAC | GAG | GAC | GGC | CAC | CAC | GCA | CAG | GAT | TCA | CTC | CAC | TAC | GAA | GGC | | | | | 432 |
| Trp | Asp | Glu | Asp | Gly | His | His | Ala | Gln | Asp | Ser | Leu | His | Tyr | Glu | Gly | | | | | |
| | 130 | | | | | 135 | | | | | 140 | | | | | | | | | |
| CGT | GCC | TTG | GAC | ATC | ACC | ACG | TCT | GAC | CGT | GAC | CGT | AAT | AAG | TAT | GGT | | | | | 480 |
| Arg | Ala | Leu | Asp | Ile | Thr | Thr | Ser | Asp | Arg | Asp | Arg | Asn | Lys | Tyr | Gly | | | | | |
| 145 | | | | | 150 | | | | | 155 | | | | | 160 | | | | | |
| TTG | TTG | GCG | CGC | CTA | GCT | GTG | GAA | GCC | GGA | TTC | GAC | TGG | GTC | TAC | TAC | | | | | 528 |
| Leu | Leu | Ala | Arg | Leu | Ala | Val | Glu | Ala | Gly | Phe | Asp | Trp | Val | Tyr | Tyr | | | | | |
| | | | | 165 | | | | | 170 | | | | | 175 | | | | | | |
| GAG | TCC | CGC | AAC | CAC | ATC | CAC | GTA | TCG | GTC | AAA | GCT | GAT | AAC | TCA | CTG | | | | | 576 |
| Glu | Ser | Arg | Asn | His | Ile | His | Val | Ser | Val | Lys | Ala | Asp | Asn | Ser | Leu | | | | | |
| | | | 180 | | | | | 185 | | | | | 190 | | | | | | | |
| GCG | GTC | CGA | GCC | GGA | GGC | TGC | TTT | CCG | GGA | AAT | GCC | ACG | GTG | CGC | TTG | | | | | 624 |
| Ala | Val | Arg | Ala | Gly | Gly | Cys | Phe | Pro | Gly | Asn | Ala | Thr | Val | Arg | Leu | | | | | |
| | | 195 | | | | | 200 | | | | | 205 | | | | | | | | |
| CGG | AGC | GGC | GAA | CGG | AAG | GGG | CTG | AGG | GAA | CTA | CAT | CGT | GGT | GAC | TGG | | | | | 672 |
| Arg | Ser | Gly | Glu | Arg | Lys | Gly | Leu | Arg | Glu | Leu | His | Arg | Gly | Asp | Trp | | | | | |
| | 210 | | | | | 215 | | | | | 220 | | | | | | | | | |
| GTA | CTG | GCC | GCT | GAT | GCA | GCG | GGC | CGA | GTG | GTA | CCC | ACG | CCA | GTG | CTG | | | | | 720 |
| Val | Leu | Ala | Ala | Asp | Ala | Ala | Gly | Arg | Val | Val | Pro | Thr | Pro | Val | Leu | | | | | |
| 225 | | | | | 230 | | | | | 235 | | | | | 240 | | | | | |
| CTC | TTC | CTG | GAC | CGG | GAT | CTG | CAG | CGC | CGC | GCC | TCG | TTC | GTG | GCT | GTG | | | | | 768 |
| Leu | Phe | Leu | Asp | Arg | Asp | Leu | Gln | Arg | Arg | Ala | Ser | Phe | Val | Ala | Val | | | | | |
| | | | | 245 | | | | | 250 | | | | | 255 | | | | | | |
| GAG | ACC | GAG | CGG | CCT | CCG | CGC | AAA | CTG | TTG | CTC | ACA | CCC | TGG | CAT | CTG | | | | | 816 |
| Glu | Thr | Glu | Arg | Pro | Pro | Arg | Lys | Leu | Leu | Leu | Thr | Pro | Trp | His | Leu | | | | | |
| | | | 260 | | | | | 265 | | | | | 270 | | | | | | | |
| GTG | TTC | GCT | GCT | CGC | GGG | CCA | GCG | CCT | GCT | CCA | GGT | GAC | TTT | GCA | CCG | | | | | 864 |
| Val | Phe | Ala | Ala | Arg | Gly | Pro | Ala | Pro | Ala | Pro | Gly | Asp | Phe | Ala | Pro | | | | | |
| | | 275 | | | | | 280 | | | | | 285 | | | | | | | | |
| GTG | TTC | GCG | CGC | CGC | TTA | CGT | GCT | GGC | GAC | TCG | GTG | CTG | GCT | CCC | GGC | | | | | 912 |
| Val | Phe | Ala | Arg | Arg | Leu | Arg | Ala | Gly | Asp | Ser | Val | Leu | Ala | Pro | Gly | | | | | |
| | | 290 | | | | | 295 | | | | | 300 | | | | | | | | |
| GGG | GAC | GCG | CTC | CAG | CCG | GCG | CGC | GTA | GCC | CGC | GTG | GCG | CGC | GAG | GAA | | | | | 960 |
| Gly | Asp | Ala | Leu | Gln | Pro | Ala | Arg | Val | Ala | Arg | Val | Ala | Arg | Glu | Glu | | | | | |
| 305 | | | | | 310 | | | | | 315 | | | | | 320 | | | | | |
| GCC | GTG | GGC | GTG | TTC | GCA | CCG | CTC | ACT | GCG | CAC | GGG | ACG | CTG | CTG | GTC | | | | | 1008 |
| Ala | Val | Gly | Val | Phe | Ala | Pro | Leu | Thr | Ala | His | Gly | Thr | Leu | Leu | Val | | | | | |
| | | | | 325 | | | | | 330 | | | | | 335 | | | | | | |
| AAC | GAC | GTC | CTC | GCC | TCC | TGC | TAC | GCG | GTT | CTA | GAG | AGT | CAC | CAG | TGG | | | | | 1056 |
| Asn | Asp | Val | Leu | Ala | Ser | Cys | Tyr | Ala | Val | Leu | Glu | Ser | His | Gln | Trp | | | | | |
| | | | 340 | | | | | 345 | | | | | 350 | | | | | | | |
| GCC | CAC | CGC | GCC | TTC | GCC | CCT | TTG | CGG | CTG | CTG | CAC | GCG | CTC | GGG | GCT | | | | | 1104 |
| Ala | His | Arg | Ala | Phe | Ala | Pro | Leu | Arg | Leu | Leu | His | Ala | Leu | Gly | Ala | | | | | |
| | | 355 | | | | | 360 | | | | | 365 | | | | | | | | |
| CTG | CTC | CCT | GGG | GGT | GCA | GTC | CAG | CCG | ACT | GGC | ATG | CAT | TGG | TAC | TCT | | | | | 1152 |
| Leu | Leu | Pro | Gly | Gly | Ala | Val | Gln | Pro | Thr | Gly | Met | His | Trp | Tyr | Ser | | | | | |
| | | 370 | | | | | 375 | | | | | 380 | | | | | | | | |
| CGC | CTC | CTT | TAC | CGC | TTG | GCC | GAG | GAG | TTA | ATG | GGC | TG | | | | | | | | 1190 |
| Arg | Leu | Leu | Tyr | Arg | Leu | Ala | Glu | Glu | Leu | Met | Gly | | | | | | | | | |
| 385 | | | | | 390 | | | | | 395 | | | | | | | | | | |

( 2 ) INFORMATION FOR SEQ ID NO:4:

( i ) SEQUENCE CHARACTERISTICS:
        ( A ) LENGTH: 396 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Leu Pro Ala Ser Leu Leu Pro Leu Cys Cys Leu Ala Leu Leu
 1               5                  10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
 65                 70                  75                  80

Tyr Asn Pro Asp Ile Ile Phe Lys Asp Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
            115                 120                 125

Trp Asp Glu Asp Gly His His Ala Gln Asp Ser Leu His Tyr Glu Gly
        130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
385                 390                 395
```

( 2 ) INFORMATION FOR SEQ ID NO:5:

( i ) SEQUENCE CHARACTERISTICS:
    ( A ) LENGTH: 1056 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: CDS
    ( B ) LOCATION: 1..1056

( x i ) SEQUENCE DESCRIPTION: SEQ ID NO:5:

```
GAG  CGC  TTC  AAA  GAG  CTC  ACC  CCC  AAC  TAC  AAT  CCC  GAC  ATC  ATC  TTC        48
Glu  Arg  Phe  Lys  Glu  Leu  Thr  Pro  Asn  Tyr  Asn  Pro  Asp  Ile  Ile  Phe
 1              5                        10                       15

AAG  GAC  GAG  GAG  AAC  ACG  GGT  GCC  GAC  CGC  CTC  ATG  ACC  CAG  CGC  TGC        96
Lys  Asp  Glu  Glu  Asn  Thr  Gly  Ala  Asp  Arg  Leu  Met  Thr  Gln  Arg  Cys
                    20                       25                       30

AAG  GAC  CGT  CTG  AAC  TCA  CTG  GCC  ATC  TCT  GTC  ATG  AAC  CAG  TGG  CCT       144
Lys  Asp  Arg  Leu  Asn  Ser  Leu  Ala  Ile  Ser  Val  Met  Asn  Gln  Trp  Pro
          35                       40                       45

GGT  GTG  AAA  CTG  CGG  GTG  ACC  GAA  GGC  CGG  GAT  GAA  GAT  GGC  CAT  CAC       192
Gly  Val  Lys  Leu  Arg  Val  Thr  Glu  Gly  Arg  Asp  Glu  Asp  Gly  His  His
          50                       55                       60

TCA  GAG  GAG  TCT  TTA  CAC  TAT  GAG  GGC  CGC  GCG  GTG  GAT  ATC  ACC  ACC       240
Ser  Glu  Glu  Ser  Leu  His  Tyr  Glu  Gly  Arg  Ala  Val  Asp  Ile  Thr  Thr
65                       70                       75                       80

TCA  GAC  CGT  GAC  CGA  AAT  AAG  TAT  GGA  CTG  CTG  GCG  CGC  TTA  GCA  GTG       288
Ser  Asp  Arg  Asp  Arg  Asn  Lys  Tyr  Gly  Leu  Leu  Ala  Arg  Leu  Ala  Val
                    85                       90                       95

GAG  GCC  GGC  TTC  GAC  TGG  GTG  TAT  TAC  GAG  TCC  AAG  GCC  CAC  GTG  CAT       336
Glu  Ala  Gly  Phe  Asp  Trp  Val  Tyr  Tyr  Glu  Ser  Lys  Ala  His  Val  His
               100                      105                      110

TGC  TCT  GTC  AAG  TCT  GAG  CAT  TCG  GCC  GCT  GCC  AAG  ACA  GGT  GGC  TGC       384
Cys  Ser  Val  Lys  Ser  Glu  His  Ser  Ala  Ala  Ala  Lys  Thr  Gly  Gly  Cys
               115                      120                      125

TTT  CCT  GCC  GGA  GCC  CAG  GTG  CGC  CTA  GAG  AAC  GGG  GAG  CGT  GTG  GCC       432
Phe  Pro  Ala  Gly  Ala  Gln  Val  Arg  Leu  Glu  Asn  Gly  Glu  Arg  Val  Ala
     130                      135                      140

CTG  TCA  GCT  GTA  AAG  CCA  GGA  GAC  CGG  GTG  CTG  GCC  ATG  GGG  GAG  GAT       480
Leu  Ser  Ala  Val  Lys  Pro  Gly  Asp  Arg  Val  Leu  Ala  Met  Gly  Glu  Asp
145                      150                      155                      160

GGG  ACC  CCC  ACC  TTC  AGT  GAT  GTG  CTT  ATT  TTC  CTG  GAC  CGC  GAG  CCA       528
Gly  Thr  Pro  Thr  Phe  Ser  Asp  Val  Leu  Ile  Phe  Leu  Asp  Arg  Glu  Pro
                    165                      170                      175

AAC  CGG  CTG  AGA  GCT  TTC  CAG  GTC  ATC  GAG  ACT  CAG  GAT  CCT  CCG  CGT       576
Asn  Arg  Leu  Arg  Ala  Phe  Gln  Val  Ile  Glu  Thr  Gln  Asp  Pro  Pro  Arg
               180                      185                      190

CGG  CTG  GCG  CTC  ACG  CCT  GCC  CAC  CTG  CTC  TTC  ATT  GCG  GAC  AAT  CAT       624
Arg  Leu  Ala  Leu  Thr  Pro  Ala  His  Leu  Leu  Phe  Ile  Ala  Asp  Asn  His
          195                      200                      205

ACA  GAA  CCA  GCA  GCC  CAC  TTC  CGG  GCC  ACA  TTT  GCC  AGC  CAT  GTG  CAA       672
Thr  Glu  Pro  Ala  Ala  His  Phe  Arg  Ala  Thr  Phe  Ala  Ser  His  Val  Gln
     210                      215                      220

CCA  GGC  CAA  TAT  GTG  CTG  GTA  TCA  GGG  GTA  CCA  GGC  CTC  CAG  CCT  GCT       720
Pro  Gly  Gln  Tyr  Val  Leu  Val  Ser  Gly  Val  Pro  Gly  Leu  Gln  Pro  Ala
225                      230                      235                      240

CGG  GTG  GCA  GCT  GTC  TCC  ACC  CAC  GTG  GCC  CTT  GGG  TCC  TAT  GCT  CCT       768
Arg  Val  Ala  Ala  Val  Ser  Thr  His  Val  Ala  Leu  Gly  Ser  Tyr  Ala  Pro
                    245                      250                      255

CTC  ACA  AGG  CAT  GGG  ACA  CTT  GTG  GTG  GAG  GAT  GTG  GTG  GCC  TCC  TGC       816
```

-continued

| | | | | | | | | | | | | | | | |
|---|---|---|---|---|---|---|---|---|---|---|---|---|---|---|---|
| Leu | Thr | Arg | His | Gly | Thr | Leu | Val | Val | Glu | Asp | Val | Val | Ala | Ser | Cys |
| | | | 260 | | | | | 265 | | | | 270 | | | |

```
TTT  GCA  GCT  GTG  GCT  GAC  CAC  CAT  CTG  GCT  CAG  TTG  GCC  TTC  TGG  CCC         864
Phe  Ala  Ala  Val  Ala  Asp  His  His  Leu  Ala  Gln  Leu  Ala  Phe  Trp  Pro
          275                      280                          285

CTG  CGA  CTG  TTT  CCC  AGT  TTG  GCA  TGG  GGC  AGC  TGG  ACC  CCA  AGT  GAG         912
Leu  Arg  Leu  Phe  Pro  Ser  Leu  Ala  Trp  Gly  Ser  Trp  Thr  Pro  Ser  Glu
290                           295                          300

GGT  GTT  CAC  TCC  TAC  CCT  CAG  ATG  CTC  TAC  CGC  CTG  GGG  CGT  CTC  TTG         960
Gly  Val  His  Ser  Tyr  Pro  Gln  Met  Leu  Tyr  Arg  Leu  Gly  Arg  Leu  Leu
305                      310                          315                      320

CTA  GAA  GAG  AGC  ACC  TTC  CAT  CCA  CTG  GGC  ATG  TCT  GGG  GCA  GGA  AGC        1008
Leu  Glu  Glu  Ser  Thr  Phe  His  Pro  Leu  Gly  Met  Ser  Gly  Ala  Gly  Ser
                    325                      330                      335

TGAAGGGACT  CTAACCACTG  CCCTCCTGGA  ACTGCTGTGC  GTGGATCC                              1056
```

( 2 ) INFORMATION FOR SEQ ID NO:6:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Glu  Arg  Phe  Lys  Glu  Leu  Thr  Pro  Asn  Tyr  Asn  Pro  Asp  Ile  Ile  Phe
 1                   5                   10                          15

Lys  Asp  Glu  Glu  Asn  Thr  Gly  Ala  Asp  Arg  Leu  Met  Thr  Gln  Arg  Cys
               20                   25                          30

Lys  Asp  Arg  Leu  Asn  Ser  Leu  Ala  Ile  Ser  Val  Met  Asn  Gln  Trp  Pro
          35                   40                   45

Gly  Val  Lys  Leu  Arg  Val  Thr  Glu  Gly  Arg  Asp  Glu  Asp  Gly  His  His
     50                   55                        60

Ser  Glu  Glu  Ser  Leu  His  Tyr  Glu  Gly  Arg  Ala  Val  Asp  Ile  Thr  Thr
65                        70                   75                          80

Ser  Asp  Arg  Asp  Arg  Asn  Lys  Tyr  Gly  Leu  Leu  Ala  Arg  Leu  Ala  Val
                    85                        90                       95

Glu  Ala  Gly  Phe  Asp  Trp  Val  Tyr  Tyr  Glu  Ser  Lys  Ala  His  Val  His
               100                      105                     110

Cys  Ser  Val  Lys  Ser  Glu  His  Ser  Ala  Ala  Ala  Lys  Thr  Gly  Gly  Cys
          115                      120                     125

Phe  Pro  Ala  Gly  Ala  Gln  Val  Arg  Leu  Glu  Asn  Gly  Glu  Arg  Val  Ala
130                      135                     140

Leu  Ser  Ala  Val  Lys  Pro  Gly  Asp  Arg  Val  Leu  Ala  Met  Gly  Glu  Asp
145                      150                     155                     160

Gly  Thr  Pro  Thr  Phe  Ser  Asp  Val  Leu  Ile  Phe  Leu  Asp  Arg  Glu  Pro
               165                      170                     175

Asn  Arg  Leu  Arg  Ala  Phe  Gln  Val  Ile  Glu  Thr  Gln  Asp  Pro  Pro  Arg
          180                      185                     190

Arg  Leu  Ala  Leu  Thr  Pro  Ala  His  Leu  Leu  Phe  Ile  Ala  Asp  Asn  His
          195                      200                     205

Thr  Glu  Pro  Ala  Ala  His  Phe  Arg  Ala  Thr  Phe  Ala  Ser  His  Val  Gln
     210                      215                     220

Pro  Gly  Gln  Tyr  Val  Leu  Val  Ser  Gly  Val  Pro  Gly  Leu  Gln  Pro  Ala
225                      230                     235                     240

Arg  Val  Ala  Ala  Val  Ser  Thr  His  Val  Ala  Leu  Gly  Ser  Tyr  Ala  Pro
                    245                      250                     255
```

```
Leu Thr Arg His Gly Thr Leu Val Val Glu Asp Val Val Ala Ser Cys
            260             265             270

Phe Ala Ala Val Ala Asp His His Leu Ala Gln Leu Ala Phe Trp Pro
        275             280             285

Leu Arg Leu Phe Pro Ser Leu Ala Trp Gly Ser Trp Thr Pro Ser Glu
    290             295             300

Gly Val His Ser Tyr Pro Gln Met Leu Tyr Arg Leu Gly Arg Leu Leu
305             310             315             320

Leu Glu Glu Ser Thr Phe His Pro Leu Gly Met Ser Gly Ala Gly Ser
            325             330             335
```

(2) INFORMATION FOR SEQ ID NO:7:

(i) SEQUENCE CHARACTERISTICS:
        (A) LENGTH: 1313 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..1314

(xi) SEQUENCE DESCRIPTION: SEQ ID NO:7:

```
ATG CTG CTG CTG CTG GCC AGA TGT TTT CTG GTG ATC CTT GCT TCC TCG    48
Met Leu Leu Leu Leu Ala Arg Cys Phe Leu Val Ile Leu Ala Ser Ser
 1               5                  10                  15

CTG CTG GTG TGC CCC GGG CTG GCC TGT GGG CCC GGC AGG GGG TTT GGA    96
Leu Leu Val Cys Pro Gly Leu Ala Cys Gly Pro Gly Arg Gly Phe Gly
             20                  25                  30

AAG AGG CGG CAC CCC AAA AAG CTG ACC CCT TTA GCC TAC AAG CAG TTT   144
Lys Arg Arg His Pro Lys Lys Leu Thr Pro Leu Ala Tyr Lys Gln Phe
         35                  40                  45

ATT CCC AAC GTA GCC GAG AAG ACC CTA GGG GCC AGC GGC AGA TAT GAA   192
Ile Pro Asn Val Ala Glu Lys Thr Leu Gly Ala Ser Gly Arg Tyr Glu
     50                  55                  60

GGG AAG ATC ACA AGA AAC TCC GAA CGA TTT AAG GAA CTC ACC CCC AAT   240
Gly Lys Ile Thr Arg Asn Ser Glu Arg Phe Lys Glu Leu Thr Pro Asn
 65                  70                  75                  80

TAC AAC CCC GAC ATC ATA TTT AAG GAT GAG GAA AAC ACG GGA GCA GAC   288
Tyr Asn Pro Asp Ile Ile Phe Lys Asp Glu Glu Asn Thr Gly Ala Asp
                 85                  90                  95

CGG CTG ATG ACT CAG AGG TGC AAA GAC AAG TTA AAT GCC TTG GCC ATC   336
Arg Leu Met Thr Gln Arg Cys Lys Asp Lys Leu Asn Ala Leu Ala Ile
            100                 105                 110

TCT GTG ATG AAC CAG TGG CCT GGA GTG AGG CTG CGA GTG ACC GAG GGC   384
Ser Val Met Asn Gln Trp Pro Gly Val Arg Leu Arg Val Thr Glu Gly
        115                 120                 125

TGG GAT GAG GAC GGC CAT CAT TCA GAG GAG TCT CTA CAC TAT GAG GGT   432
Trp Asp Glu Asp Gly His His Ser Glu Glu Ser Leu His Tyr Glu Gly
    130                 135                 140

CGA GCA GTG GAC ATC ACC ACG TCC GAC CGG GAC CGC AGC AAG TAC GGC   480
Arg Ala Val Asp Ile Thr Thr Ser Asp Arg Asp Arg Ser Lys Tyr Gly
145                 150                 155                 160

ATG CTG GCT CGC CTG GCT GTG GAA GCA GGT TTC GAC TGG GTC TAC TAT   528
Met Leu Ala Arg Leu Ala Val Glu Ala Gly Phe Asp Trp Val Tyr Tyr
                165                 170                 175

GAA TCC AAA GCT CAC ATC CAC TGT TCT GTG AAA GCA GAG AAC TCC GTG   576
Glu Ser Lys Ala His Ile His Cys Ser Val Lys Ala Glu Asn Ser Val
            180                 185                 190
```

| | | | | | | | | | | | | | | | |
|---|---|---|---|---|---|---|---|---|---|---|---|---|---|---|---|
| GCG | GCC | AAA | TCC | GGC | GGC | TGT | TTC | CCG | GGA | TCC | GCC | ACC | GTG | CAC | CTG | 624
| Ala | Ala | Lys | Ser | Gly | Gly | Cys | Phe | Pro | Gly | Ser | Ala | Thr | Val | His | Leu |
| | | 195 | | | | | 200 | | | | | 205 | | | |
| GAG | CAG | GGC | GGC | ACC | AAG | CTG | GTG | AAG | GAC | TTA | CGT | CCC | GGA | GAC | CGC | 672
| Glu | Gln | Gly | Gly | Thr | Lys | Leu | Val | Lys | Asp | Leu | Arg | Pro | Gly | Asp | Arg |
| | 210 | | | | | 215 | | | | | 220 | | | | |
| GTG | CTG | GCG | GCT | GAC | GAC | CAG | GGC | CGG | CTG | CTG | TAC | AGC | GAC | TTC | CTC | 720
| Val | Leu | Ala | Ala | Asp | Asp | Gln | Gly | Arg | Leu | Leu | Tyr | Ser | Asp | Phe | Leu |
| 225 | | | | | 230 | | | | | 235 | | | | | 240 |
| ACC | TTC | CTG | GAC | CGC | GAC | GAA | GGC | GCC | AAG | AAG | GTC | TTC | TAC | GTG | ATC | 768
| Thr | Phe | Leu | Asp | Arg | Asp | Glu | Gly | Ala | Lys | Lys | Val | Phe | Tyr | Val | Ile |
| | | | | 245 | | | | | 250 | | | | | 255 | |
| GAG | ACG | CTG | GAG | CCG | CGC | GAG | CGC | CTG | CTG | CTC | ACC | GCC | GCG | CAC | CTG | 816
| Glu | Thr | Leu | Glu | Pro | Arg | Glu | Arg | Leu | Leu | Leu | Thr | Ala | Ala | His | Leu |
| | | | 260 | | | | | 265 | | | | | 270 | | |
| CTC | TTC | GTG | GCG | CCG | CAC | AAC | GAC | TCG | GGG | CCC | ACG | CCC | GGG | CCA | AGC | 864
| Leu | Phe | Val | Ala | Pro | His | Asn | Asp | Ser | Gly | Pro | Thr | Pro | Gly | Pro | Ser |
| | | 275 | | | | | 280 | | | | | 285 | | | |
| GCG | CTC | TTT | GCC | AGC | CGC | GTG | CGC | CCC | GGG | CAG | CGC | GTG | TAC | GTG | GTG | 912
| Ala | Leu | Phe | Ala | Ser | Arg | Val | Arg | Pro | Gly | Gln | Arg | Val | Tyr | Val | Val |
| | 290 | | | | | 295 | | | | | 300 | | | | |
| GCT | GAA | CGC | GGC | GGG | GAC | CGC | CGG | CTG | CTG | CCC | GCC | GCG | GTG | CAC | AGC | 960
| Ala | Glu | Arg | Gly | Gly | Asp | Arg | Arg | Leu | Leu | Pro | Ala | Ala | Val | His | Ser |
| 305 | | | | | 310 | | | | | 315 | | | | | 320 |
| GTG | ACG | CTG | CGA | GAG | GAG | GAG | GCG | GGC | GCG | TAC | GCG | CCG | CTC | ACG | GCG | 1008
| Val | Thr | Leu | Arg | Glu | Glu | Glu | Ala | Gly | Ala | Tyr | Ala | Pro | Leu | Thr | Ala |
| | | | | 325 | | | | | 330 | | | | | 335 | |
| CAC | GGC | ACC | ATT | CTC | ATC | AAC | CGG | GTG | CTC | GCC | TCG | TGC | TAC | GCT | GTC | 1056
| His | Gly | Thr | Ile | Leu | Ile | Asn | Arg | Val | Leu | Ala | Ser | Cys | Tyr | Ala | Val |
| | | | 340 | | | | | 345 | | | | | 350 | | |
| ATC | GAG | GAG | CAC | AGC | TGG | GCA | CAC | CGG | GCC | TTC | GCG | CCT | TTC | CGC | CTG | 1104
| Ile | Glu | Glu | His | Ser | Trp | Ala | His | Arg | Ala | Phe | Ala | Pro | Phe | Arg | Leu |
| | | 355 | | | | | 360 | | | | | 365 | | | |
| GCG | CAC | GCG | CTG | CTG | GCC | GCG | CTG | GCA | CCC | GCC | CGC | ACG | GAC | GGC | GGG | 1152
| Ala | His | Ala | Leu | Leu | Ala | Ala | Leu | Ala | Pro | Ala | Arg | Thr | Asp | Gly | Gly |
| | 370 | | | | | 375 | | | | | 380 | | | | |
| GGC | GGG | GGC | AGC | ATC | CCT | GCA | GCG | CAA | TCT | GCA | ACG | GAA | GCG | AGG | GGC | 1200
| Gly | Gly | Gly | Ser | Ile | Pro | Ala | Ala | Gln | Ser | Ala | Thr | Glu | Ala | Arg | Gly |
| 385 | | | | | 390 | | | | | 395 | | | | | 400 |
| GCG | GAG | CCG | ACT | GCG | GGC | ATC | CAC | TGG | TAC | TCG | CAG | CTG | CTC | TAC | CAC | 1248
| Ala | Glu | Pro | Thr | Ala | Gly | Ile | His | Trp | Tyr | Ser | Gln | Leu | Leu | Tyr | His |
| | | | | 405 | | | | 410 | | | | | 415 | | |
| ATT | GGC | ACC | TGG | CTG | TTG | GAC | AGC | GAG | ACC | ATG | CAT | CCC | TTG | GGA | ATG | 1296
| Ile | Gly | Thr | Trp | Leu | Leu | Asp | Ser | Glu | Thr | Met | His | Pro | Leu | Gly | Met |
| | | | 420 | | | | | 425 | | | | | 430 | | |
| GCG | GTC | AAG | TCC | AGC | TG | | | | | | | | | | | 1313
| Ala | Val | Lys | Ser | Ser | | | | | | | | | | | |
| | | 435 | | | | | | | | | | | | | |

( 2 ) INFORMATION FOR SEQ ID NO:8:

( i ) SEQUENCE CHARACTERISTICS:
        ( A ) LENGTH: 437 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Leu | Leu | Leu | Leu | Ala | Arg | Cys | Phe | Leu | Val | Ile | Leu | Ala | Ser | Ser |
|---|---|---|---|---|---|---|---|---|---|---|---|---|---|---|---|
| 1 | | | | 5 | | | | | 10 | | | | | 15 | |

```
Leu  Leu  Val  Cys  Pro  Gly  Leu  Ala  Cys  Gly  Pro  Gly  Arg  Gly  Phe  Gly
          20                       25                       30

Lys  Arg  Arg  His  Pro  Lys  Lys  Leu  Thr  Pro  Leu  Ala  Tyr  Lys  Gln  Phe
          35                       40                       45

Ile  Pro  Asn  Val  Ala  Glu  Lys  Thr  Leu  Gly  Ala  Ser  Gly  Arg  Tyr  Glu
          50                       55                       60

Gly  Lys  Ile  Thr  Arg  Asn  Ser  Glu  Arg  Phe  Lys  Glu  Leu  Thr  Pro  Asn
 65                      70                       75                        80

Tyr  Asn  Pro  Asp  Ile  Ile  Phe  Lys  Asp  Glu  Asn  Thr  Gly  Ala  Asp
                         85                       90                       95

Arg  Leu  Met  Thr  Gln  Arg  Cys  Lys  Asp  Lys  Leu  Asn  Ala  Leu  Ala  Ile
               100                      105                     110

Ser  Val  Met  Asn  Gln  Trp  Pro  Gly  Val  Arg  Leu  Arg  Val  Thr  Glu  Gly
               115                      120                     125

Trp  Asp  Glu  Asp  Gly  His  His  Ser  Glu  Glu  Ser  Leu  His  Tyr  Glu  Gly
          130                      135                     140

Arg  Ala  Val  Asp  Ile  Thr  Thr  Ser  Asp  Arg  Asp  Arg  Ser  Lys  Tyr  Gly
145                      150                     155                     160

Met  Leu  Ala  Arg  Leu  Ala  Val  Glu  Ala  Gly  Phe  Asp  Trp  Val  Tyr  Tyr
               165                      170                     175

Glu  Ser  Lys  Ala  His  Ile  His  Cys  Ser  Val  Lys  Ala  Glu  Asn  Ser  Val
               180                      185                     190

Ala  Ala  Lys  Ser  Gly  Gly  Cys  Phe  Pro  Gly  Ser  Ala  Thr  Val  His  Leu
          195                      200                     205

Glu  Gln  Gly  Gly  Thr  Lys  Leu  Val  Lys  Asp  Leu  Arg  Pro  Gly  Asp  Arg
     210                      215                     220

Val  Leu  Ala  Ala  Asp  Asp  Gln  Gly  Arg  Leu  Leu  Tyr  Ser  Asp  Phe  Leu
225                      230                     235                     240

Thr  Phe  Leu  Asp  Arg  Asp  Glu  Gly  Ala  Lys  Lys  Val  Phe  Tyr  Val  Ile
               245                      250                     255

Glu  Thr  Leu  Glu  Pro  Arg  Glu  Arg  Leu  Leu  Leu  Thr  Ala  Ala  His  Leu
               260                      265                     270

Leu  Phe  Val  Ala  Pro  His  Asn  Asp  Ser  Gly  Pro  Thr  Pro  Gly  Pro  Ser
          275                      280                     285

Ala  Leu  Phe  Ala  Ser  Arg  Val  Arg  Pro  Gly  Gln  Arg  Val  Tyr  Val  Val
     290                      295                     300

Ala  Glu  Arg  Gly  Gly  Asp  Arg  Arg  Leu  Leu  Pro  Ala  Ala  Val  His  Ser
305                      310                     315                     320

Val  Thr  Leu  Arg  Glu  Glu  Glu  Ala  Gly  Ala  Tyr  Ala  Pro  Leu  Thr  Ala
               325                      330                     335

His  Gly  Thr  Ile  Leu  Ile  Asn  Arg  Val  Leu  Ala  Ser  Cys  Tyr  Ala  Val
               340                      345                     350

Ile  Glu  Glu  His  Ser  Trp  Ala  His  Arg  Ala  Phe  Ala  Pro  Phe  Arg  Leu
          355                      360                     365

Ala  His  Ala  Leu  Leu  Ala  Ala  Leu  Ala  Pro  Ala  Arg  Thr  Asp  Gly  Gly
     370                      375                     380

Gly  Gly  Gly  Ser  Ile  Pro  Ala  Ala  Gln  Ser  Ala  Thr  Glu  Ala  Arg  Gly
385                      390                     395                     400

Ala  Glu  Pro  Thr  Ala  Gly  Ile  His  Trp  Tyr  Ser  Gln  Leu  Leu  Tyr  His
               405                      410                     415

Ile  Gly  Thr  Trp  Leu  Leu  Asp  Ser  Glu  Thr  Met  His  Pro  Leu  Gly  Met
               420                      425                     430

Ala  Val  Lys  Ser  Ser
          435
```

( 2 ) INFORMATION FOR SEQ ID NO:9:

( i ) SEQUENCE CHARACTERISTICS:
        ( A ) LENGTH: 1256 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..1257

( x i ) SEQUENCE DESCRIPTION: SEQ ID NO:9:

```
ATG CGG CTT TTG ACG AGA GTG CTG CTG GTG TCT CTT CTC ACT CTG TCC        48
Met Arg Leu Leu Thr Arg Val Leu Leu Val Ser Leu Leu Thr Leu Ser
 1               5                  10                  15

TTG GTG GTG TCC GGA CTG GCC TGC GGT CCT GGC AGA GGC TAC GGC AGA        96
Leu Val Val Ser Gly Leu Ala Cys Gly Pro Gly Arg Gly Tyr Gly Arg
             20                  25                  30

AGA AGA CAT CCG AAG AAG CTG ACA CCT CTC GCC TAC AAG CAG TTC ATA       144
Arg Arg His Pro Lys Lys Leu Thr Pro Leu Ala Tyr Lys Gln Phe Ile
         35                  40                  45

CCT AAT GTC GCG GAG AAG ACC TTA GGG GCC AGC GGC AGA TAC GAG GGC       192
Pro Asn Val Ala Glu Lys Thr Leu Gly Ala Ser Gly Arg Tyr Glu Gly
     50                  55                  60

AAG ATA ACG CGC AAT TCG GAG AGA TTT AAA GAA CTT ACT CCA AAT TAC       240
Lys Ile Thr Arg Asn Ser Glu Arg Phe Lys Glu Leu Thr Pro Asn Tyr
 65                  70                  75                  80

AAT CCC GAC ATT ATC TTT AAG GAT GAG GAG AAC ACG GGA GCG GAC AGG       288
Asn Pro Asp Ile Ile Phe Lys Asp Glu Glu Asn Thr Gly Ala Asp Arg
                 85                  90                  95

CTC ATG ACA CAG AGA TGC AAA GAC AAG CTG AAC TCG CTG GCC ATC TCT       336
Leu Met Thr Gln Arg Cys Lys Asp Lys Leu Asn Ser Leu Ala Ile Ser
            100                 105                 110

GTA ATG AAC CAC TGG CCA GGG GTT AAG CTG CGT GTG ACA GAG GGC TGG       384
Val Met Asn His Trp Pro Gly Val Lys Leu Arg Val Thr Glu Gly Trp
        115                 120                 125

GAT GAG GAC GGT CAC CAT TTT GAA GAA TCA CTC CAC TAC GAG GGA AGA       432
Asp Glu Asp Gly His His Phe Glu Glu Ser Leu His Tyr Glu Gly Arg
    130                 135                 140

GCT GTT GAT ATT ACC ACC TCT GAC CGA GAC AAG AGC AAA TAC GGG ACA       480
Ala Val Asp Ile Thr Thr Ser Asp Arg Asp Lys Ser Lys Tyr Gly Thr
145                 150                 155                 160

CTG TCT CGC CTA GCT GTG GAG GCT GGA TTT GAC TGG GTC TAT TAC GAG       528
Leu Ser Arg Leu Ala Val Glu Ala Gly Phe Asp Trp Val Tyr Tyr Glu
                165                 170                 175

TCC AAA GCC CAC ATT CAT TGC TCT GTC AAA GCA GAA AAT TCG GTT GCT       576
Ser Lys Ala His Ile His Cys Ser Val Lys Ala Glu Asn Ser Val Ala
            180                 185                 190

GCG AAA TCT GGG GGC TGT TTC CCA GGT TCG GCT CTG GTC TCG CTC CAG       624
Ala Lys Ser Gly Gly Cys Phe Pro Gly Ser Ala Leu Val Ser Leu Gln
        195                 200                 205

GAC GGA GGA CAG AAG GCC GTG AAG GAC CTG AAC CCC GGA GAC AAG GTG       672
Asp Gly Gly Gln Lys Ala Val Lys Asp Leu Asn Pro Gly Asp Lys Val
    210                 215                 220

CTG GCG GCA GAC AGC GCG GGA AAC CTG GTG TTC AGC GAC TTC ATC ATG       720
Leu Ala Ala Asp Ser Ala Gly Asn Leu Val Phe Ser Asp Phe Ile Met
225                 230                 235                 240

TTC ACA GAC CGA GAC TCC ACG ACG CGA CGT GTG TTT TAC GTC ATA GAA       768
Phe Thr Asp Arg Asp Ser Thr Thr Arg Arg Val Phe Tyr Val Ile Glu
```

|   |   |   | 245 |   |   |   |   | 250 |   |   |   |   | 255 |   |   |   |
|---|---|---|---|---|---|---|---|---|---|---|---|---|---|---|---|---|
| ACG | CAA | GAA | CCC | GTT | GAA | AAG | ATC | ACC | CTC | ACC | GCC | GCT | CAC | CTC | CTT | 816 |
| Thr | Gln | Glu | Pro | Val | Glu | Lys | Ile | Thr | Leu | Thr | Ala | Ala | His | Leu | Leu |   |
|   |   |   | 260 |   |   |   |   | 265 |   |   |   |   | 270 |   |   |   |
| TTT | GTC | CTC | GAC | AAC | TCA | ACG | GAA | GAT | CTC | CAC | ACC | ATG | ACC | GCC | GCG | 864 |
| Phe | Val | Leu | Asp | Asn | Ser | Thr | Glu | Asp | Leu | His | Thr | Met | Thr | Ala | Ala |   |
|   |   | 275 |   |   |   |   | 280 |   |   |   |   | 285 |   |   |   |   |
| TAT | GCC | AGC | AGT | GTC | AGA | GCC | GGA | CAA | AAG | GTG | ATG | GTT | GTT | GAT | GAT | 912 |
| Tyr | Ala | Ser | Ser | Val | Arg | Ala | Gly | Gln | Lys | Val | Met | Val | Val | Asp | Asp |   |
|   | 290 |   |   |   |   | 295 |   |   |   |   | 300 |   |   |   |   |   |
| AGC | GGT | CAG | CTT | AAA | TCT | GTC | ATC | GTG | CAG | CGG | ATA | TAC | ACG | GAG | GAG | 960 |
| Ser | Gly | Gln | Leu | Lys | Ser | Val | Ile | Val | Gln | Arg | Ile | Tyr | Thr | Glu | Glu |   |
| 305 |   |   |   | 310 |   |   |   |   | 315 |   |   |   |   | 320 |   |   |
| CAG | CGG | GGC | TCG | TTC | GCA | CCA | GTG | ACT | GCA | CAT | GGG | ACC | ATT | GTG | GTC | 1008 |
| Gln | Arg | Gly | Ser | Phe | Ala | Pro | Val | Thr | Ala | His | Gly | Thr | Ile | Val | Val |   |
|   |   |   |   | 325 |   |   |   |   | 330 |   |   |   |   | 335 |   |   |
| GAC | AGA | ATA | CTG | GCG | TCC | TGT | TAC | GCC | GTA | ATA | GAG | GAC | CAG | GGG | CTT | 1056 |
| Asp | Arg | Ile | Leu | Ala | Ser | Cys | Tyr | Ala | Val | Ile | Glu | Asp | Gln | Gly | Leu |   |
|   |   |   | 340 |   |   |   |   | 345 |   |   |   |   | 350 |   |   |   |
| GCG | CAT | TTG | GCC | TTC | GCG | CCC | GCC | AGG | CTC | TAT | TAT | TAC | GTG | TCA | TCA | 1104 |
| Ala | His | Leu | Ala | Phe | Ala | Pro | Ala | Arg | Leu | Tyr | Tyr | Tyr | Val | Ser | Ser |   |
|   |   | 355 |   |   |   |   | 360 |   |   |   |   | 365 |   |   |   |   |
| TTC | CTG | TCC | CCC | AAA | ACT | CCA | GCA | GTC | GGT | CCA | ATG | CGA | CTT | TAC | AAC | 1152 |
| Phe | Leu | Ser | Pro | Lys | Thr | Pro | Ala | Val | Gly | Pro | Met | Arg | Leu | Tyr | Asn |   |
|   | 370 |   |   |   |   | 375 |   |   |   |   | 380 |   |   |   |   |   |
| AGG | AGG | GGG | TCC | ACT | GGT | ACT | CCA | GGC | TCC | TGT | CAT | CAA | ATG | GGA | ACG | 1200 |
| Arg | Arg | Gly | Ser | Thr | Gly | Thr | Pro | Gly | Ser | Cys | His | Gln | Met | Gly | Thr |   |
| 385 |   |   |   |   | 390 |   |   |   |   | 395 |   |   |   |   | 400 |   |
| TGG | CTT | TTG | GAC | AGC | AAC | ATG | CTT | CAT | CCT | TTG | GGG | ATG | TCA | GTA | AAC | 1248 |
| Trp | Leu | Leu | Asp | Ser | Asn | Met | Leu | His | Pro | Leu | Gly | Met | Ser | Val | Asn |   |
|   |   |   |   | 405 |   |   |   |   | 410 |   |   |   |   | 415 |   |   |
| TCA | AGC | TG |   |   |   |   |   |   |   |   |   |   |   |   |   | 1256 |
| Ser | Ser |   |   |   |   |   |   |   |   |   |   |   |   |   |   |   |

( 2 ) INFORMATION FOR SEQ ID NO:10:

( i ) SEQUENCE CHARACTERISTICS:
        ( A ) LENGTH: 418 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Arg | Leu | Leu | Thr | Arg | Val | Leu | Leu | Val | Ser | Leu | Leu | Thr | Leu | Ser |
|---|---|---|---|---|---|---|---|---|---|---|---|---|---|---|---|
| 1 |   |   |   | 5 |   |   |   |   | 10 |   |   |   |   | 15 |   |
| Leu | Val | Val | Ser | Gly | Leu | Ala | Cys | Gly | Pro | Gly | Arg | Gly | Tyr | Gly | Arg |
|   |   |   | 20 |   |   |   |   | 25 |   |   |   |   | 30 |   |   |
| Arg | Arg | His | Pro | Lys | Lys | Leu | Thr | Pro | Leu | Ala | Tyr | Lys | Gln | Phe | Ile |
|   |   | 35 |   |   |   |   | 40 |   |   |   |   | 45 |   |   |   |
| Pro | Asn | Val | Ala | Glu | Lys | Thr | Leu | Gly | Ala | Ser | Gly | Arg | Tyr | Glu | Gly |
|   | 50 |   |   |   |   | 55 |   |   |   |   | 60 |   |   |   |   |
| Lys | Ile | Thr | Arg | Asn | Ser | Glu | Arg | Phe | Lys | Glu | Leu | Thr | Pro | Asn | Tyr |
| 65 |   |   |   |   | 70 |   |   |   |   | 75 |   |   |   |   | 80 |
| Asn | Pro | Asp | Ile | Ile | Phe | Lys | Asp | Glu | Glu | Asn | Thr | Gly | Ala | Asp | Arg |
|   |   |   |   | 85 |   |   |   |   | 90 |   |   |   |   | 95 |   |
| Leu | Met | Thr | Gln | Arg | Cys | Lys | Asp | Lys | Leu | Asn | Ser | Leu | Ala | Ile | Ser |
|   |   |   | 100 |   |   |   |   | 105 |   |   |   |   | 110 |   |   |
| Val | Met | Asn | His | Trp | Pro | Gly | Val | Lys | Leu | Arg | Val | Thr | Glu | Gly | Trp |
|   |   | 115 |   |   |   |   | 120 |   |   |   |   | 125 |   |   |   |

| Asp | Glu | Asp | Gly | His | His | Phe | Glu | Glu | Ser | Leu | His | Tyr | Gly | Arg |
| | 130 | | | | 135 | | | | | | 140 | | | |

| Ala | Val | Asp | Ile | Thr | Thr | Ser | Asp | Arg | Asp | Lys | Ser | Lys | Tyr | Gly | Thr |
| 145 | | | | | 150 | | | | | 155 | | | | | 160 |

| Leu | Ser | Arg | Leu | Ala | Val | Glu | Ala | Gly | Phe | Asp | Trp | Val | Tyr | Tyr | Glu |
| | | | | 165 | | | | 170 | | | | | 175 | | |

| Ser | Lys | Ala | His | Ile | His | Cys | Ser | Val | Lys | Ala | Glu | Asn | Ser | Val | Ala |
| | | | 180 | | | | | 185 | | | | | 190 | | |

| Ala | Lys | Ser | Gly | Gly | Cys | Phe | Pro | Gly | Ser | Ala | Leu | Val | Ser | Leu | Gln |
| | | 195 | | | | | 200 | | | | | 205 | | | |

| Asp | Gly | Gly | Gln | Lys | Ala | Val | Lys | Asp | Leu | Asn | Pro | Gly | Asp | Lys | Val |
| | 210 | | | | | 215 | | | | | 220 | | | | |

| Leu | Ala | Ala | Asp | Ser | Ala | Gly | Asn | Leu | Val | Phe | Ser | Asp | Phe | Ile | Met |
| 225 | | | | | 230 | | | | | 235 | | | | | 240 |

| Phe | Thr | Asp | Arg | Asp | Ser | Thr | Thr | Arg | Arg | Val | Phe | Tyr | Val | Ile | Glu |
| | | | | 245 | | | | | 250 | | | | | 255 | |

| Thr | Gln | Glu | Pro | Val | Glu | Lys | Ile | Thr | Leu | Thr | Ala | Ala | His | Leu | Leu |
| | | | 260 | | | | | 265 | | | | | 270 | | |

| Phe | Val | Leu | Asp | Asn | Ser | Thr | Glu | Asp | Leu | His | Thr | Met | Thr | Ala | Ala |
| | | 275 | | | | | 280 | | | | | 285 | | | |

| Tyr | Ala | Ser | Ser | Val | Arg | Ala | Gly | Gln | Lys | Val | Met | Val | Val | Asp | Asp |
| | 290 | | | | | 295 | | | | | 300 | | | | |

| Ser | Gly | Gln | Leu | Lys | Ser | Val | Ile | Val | Gln | Arg | Ile | Tyr | Thr | Glu | Glu |
| 305 | | | | | 310 | | | | | 315 | | | | | 320 |

| Gln | Arg | Gly | Ser | Phe | Ala | Pro | Val | Thr | Ala | His | Gly | Thr | Ile | Val | Val |
| | | | | 325 | | | | | 330 | | | | | 335 | |

| Asp | Arg | Ile | Leu | Ala | Ser | Cys | Tyr | Ala | Val | Ile | Glu | Asp | Gln | Gly | Leu |
| | | | 340 | | | | | 345 | | | | | 350 | | |

| Ala | His | Leu | Ala | Phe | Ala | Pro | Ala | Arg | Leu | Tyr | Tyr | Tyr | Val | Ser | Ser |
| | | 355 | | | | | 360 | | | | | 365 | | | |

| Phe | Leu | Ser | Pro | Lys | Thr | Pro | Ala | Val | Gly | Pro | Met | Arg | Leu | Tyr | Asn |
| | 370 | | | | | 375 | | | | | 380 | | | | |

| Arg | Arg | Gly | Ser | Thr | Gly | Thr | Pro | Gly | Ser | Cys | His | Gln | Met | Gly | Thr |
| 385 | | | | | 390 | | | | | 395 | | | | | 400 |

| Trp | Leu | Leu | Asp | Ser | Asn | Met | Leu | His | Pro | Leu | Gly | Met | Ser | Val | Asn |
| | | | | 405 | | | | | 410 | | | | | 415 | |

| Ser | Ser |

(2) INFORMATION FOR SEQ ID NO:11:

(i) SEQUENCE CHARACTERISTICS:
     (A) LENGTH: 471 amino acids
     (B) TYPE: amino acid
     (D) TOPOLOGY: linear (ii) MOLECULE TYPE: peptide (v) FRAGMENT TYPE: internal (xi) SEQUENCE DESCRIPTION: SEQ ID NO:11:

| Met | Asp | Asn | His | Ser | Ser | Val | Pro | Trp | Ala | Ser | Ala | Ala | Ser | Val | Thr |
| 1 | | | | 5 | | | | | 10 | | | | | 15 | |

| Cys | Leu | Ser | Leu | Asp | Ala | Lys | Cys | His | Ser | Ser | Ser | Ser | Ser | Ser | Ser |
| | | | 20 | | | | | 25 | | | | | 30 | | |

| Ser | Lys | Ser | Ala | Ala | Ser | Ser | Ile | Ser | Ala | Ile | Pro | Gln | Glu | Glu | Thr |
| | | 35 | | | | | 40 | | | | | 45 | | | |

```
Gln  Thr  Met  Arg  His  Ile  Ala  His  Thr  Gln  Arg  Cys  Leu  Ser  Arg  Leu
     50                      55                      60

Thr  Ser  Leu  Val  Ala  Leu  Leu  Ile  Val  Leu  Pro  Met  Val  Phe  Ser
65                       70                  75                           80

Pro  Ala  His  Ser  Cys  Gly  Pro  Gly  Arg  Gly  Leu  Gly  Arg  His  Arg  Ala
                    85                       90                      95

Arg  Asn  Leu  Tyr  Pro  Leu  Val  Leu  Lys  Gln  Thr  Ile  Pro  Asn  Leu  Ser
               100                      105                     110

Glu  Tyr  Thr  Asn  Ser  Ala  Ser  Gly  Pro  Leu  Glu  Gly  Val  Ile  Arg  Arg
               115                      120                     125

Asp  Ser  Pro  Lys  Phe  Lys  Asp  Leu  Val  Pro  Asn  Tyr  Asn  Arg  Asp  Ile
     130                      135                     140

Leu  Phe  Arg  Asp  Glu  Glu  Gly  Thr  Gly  Ala  Asp  Arg  Leu  Met  Ser  Lys
145                      150                      155                          160

Arg  Cys  Lys  Glu  Lys  Leu  Asn  Val  Leu  Ala  Tyr  Ser  Val  Met  Asn  Glu
                    165                      170                          175

Trp  Pro  Gly  Ile  Arg  Leu  Leu  Val  Thr  Glu  Ser  Trp  Asp  Glu  Asp  Tyr
               180                      185                     190

His  His  Gly  Gln  Glu  Ser  Leu  His  Tyr  Glu  Gly  Arg  Ala  Val  Thr  Ile
               195                      200                     205

Ala  Thr  Ser  Asp  Arg  Asp  Gln  Ser  Lys  Tyr  Gly  Met  Leu  Ala  Arg  Leu
     210                      215                      220

Ala  Val  Glu  Ala  Gly  Phe  Asp  Trp  Val  Ser  Tyr  Val  Ser  Arg  Arg  His
225                      230                      235                          240

Ile  Tyr  Cys  Ser  Val  Lys  Ser  Asp  Ser  Ser  Ile  Ser  Ser  His  Val  His
                    245                      250                          255

Gly  Cys  Phe  Thr  Pro  Glu  Ser  Thr  Ala  Leu  Leu  Glu  Ser  Gly  Val  Arg
               260                      265                     270

Lys  Pro  Leu  Gly  Glu  Leu  Ser  Ile  Gly  Asp  Arg  Val  Leu  Ser  Met  Thr
          275                      280                     285

Ala  Asn  Gly  Gln  Ala  Val  Tyr  Ser  Glu  Val  Ile  Leu  Phe  Met  Asp  Arg
     290                      295                     300

Asn  Leu  Glu  Gln  Met  Gln  Asn  Phe  Val  Gln  Leu  His  Thr  Asp  Gly  Gly
305                      310                      315                          320

Ala  Val  Leu  Thr  Val  Thr  Pro  Ala  His  Leu  Val  Ser  Val  Trp  Gln  Pro
               325                      330                     335

Glu  Ser  Gln  Lys  Leu  Thr  Phe  Val  Phe  Ala  Asp  Arg  Ile  Glu  Glu  Lys
          340                      345                     350

Asn  Gln  Val  Leu  Val  Arg  Asp  Val  Glu  Thr  Gly  Glu  Leu  Arg  Pro  Gln
          355                      360                     365

Arg  Val  Val  Lys  Val  Gly  Ser  Val  Arg  Ser  Lys  Gly  Val  Val  Ala  Pro
     370                      375                      380

Leu  Thr  Arg  Glu  Gly  Thr  Ile  Val  Val  Asn  Ser  Val  Ala  Ala  Ser  Cys
385                      390                      395                          400

Tyr  Ala  Val  Ile  Asn  Ser  Gln  Ser  Leu  Ala  His  Trp  Gly  Leu  Ala  Pro
               405                      410                     415

Met  Arg  Leu  Leu  Ser  Thr  Leu  Glu  Ala  Trp  Leu  Pro  Ala  Lys  Glu  Gln
               420                      425                     430

Leu  His  Ser  Ser  Pro  Lys  Val  Val  Ser  Ser  Ala  Gln  Gln  Gln  Asn  Gly
          435                      440                     445

Ile  His  Trp  Tyr  Ala  Asn  Ala  Leu  Tyr  Lys  Val  Lys  Asp  Tyr  Val  Leu
     450                      455                     460

Pro  Gln  Ser  Trp  Arg  His  Asp
465                      470
```

(2) INFORMATION FOR SEQ ID NO:12:

(i) SEQUENCE CHARACTERISTICS:
        (A) LENGTH: 73 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

```
Arg Cys Lys Glu Arg Val Asn Ser Leu Ala Ile Ala Val Met His Met
1               5                   10                  15
Trp Pro Gly Val Arg Leu Arg Val Thr Glu Gly Trp Asp Glu Asp Gly
                20                  25                  30
His His Leu Pro Asp Ser Leu His Tyr Glu Gly Arg Ala Leu Asp Ile
            35                  40                  45
Thr Thr Ser Asp Arg Asp Arg His Lys Tyr Gly Met Leu Ala Arg Leu
        50                  55                  60
Ala Val Glu Ala Gly Phe Asp Trp Val
65                  70
```

(2) INFORMATION FOR SEQ ID NO:13:

(i) SEQUENCE CHARACTERISTICS:
        (A) LENGTH: 73 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Arg Cys Lys Asp Lys Leu Asn Ala Leu Ala Ile Ser Val Met Asn Gln
1               5                   10                  15
Trp Pro Gly Val Lys Leu Arg Val Thr Glu Gly Trp Asp Glu Asp Gly
                20                  25                  30
His His Ser Glu Glu Ser Leu His Tyr Glu Gly Arg Ala Val Asp Ile
            35                  40                  45
Thr Thr Ser Asp Arg Asp Arg Ser Lys Tyr Gly Met Leu Ala Arg Leu
        50                  55                  60
Ala Val Glu Ala Gly Phe Asp Trp Val
65                  70
```

(2) INFORMATION FOR SEQ ID NO:14:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

```
Lys Arg Cys Lys Glu Lys Leu Asn Val Leu Ala Tyr Ser Val Met Asn
1               5                   10                  15
Glu Trp Pro Gly Ile Arg Leu Val Val Thr Glu Ser Trp Asp Glu Asp
                20                  25                  30
Tyr His His Gly Gln Glu Ser Leu His Tyr Glu Gly Arg Ala Val Thr
```

|     |     |     |     |     | 35  |     |     |     |     | 40  |     |     |     |     | 45  |
| --- | --- | --- | --- | --- | --- | --- | --- | --- | --- | --- | --- | --- | --- | --- | --- |

```
Ile Ala Thr Ser Asp Arg Asp Gln Ser Lys Tyr Gly Met Leu Ala Arg
    50                  55                  60
```

( 2 ) INFORMATION FOR SEQ ID NO:15:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:15:

```
Gln Arg Cys Lys Asp Lys Leu Asn Ser Leu Ala Ile Ser Val Met Asn
1               5                   10                  15

His Trp Pro Gly Val Lys Leu Arg Val Thr Glu Gly Trp Asp Glu Asp
            20                  25                  30

Gly His His Phe Glu Glu Ser Leu His Tyr Glu Gly Arg Ala Val Asp
        35                  40                  45

Ile Thr Thr Ser Asp Arg Asp Lys Ser Lys Tyr Gly Thr Leu Ser Arg
    50                  55                  60
```

( 2 ) INFORMATION FOR SEQ ID NO:16:

( i ) SEQUENCE CHARACTERISTICS:
        ( A ) LENGTH: 65 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:16:

```
Gln Arg Cys Lys Glu Lys Leu Asn Ser Leu Ala Ile Ser Val Met Asn
1               5                   10                  15

Met Trp Pro Gly Val Lys Leu Arg Val Thr Glu Gly Trp Asp Glu Asp
            20                  25                  30

Gly Asn His Phe Glu Asp Ser Leu His Tyr Glu Gly Arg Ala Val Asp
        35                  40                  45

Ile Thr Thr Ser Ser Asp Arg Asp Arg Asn Lys Tyr Gly Met Phe Ala
    50                  55                  60
Arg
65
```

( 2 ) INFORMATION FOR SEQ ID NO:17:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:17:

```
Gln Arg Cys Lys Asp Lys Leu Asn Ser Leu Ala Ile Ser Val Met Asn
1               5                   10                  15

Leu Trp Pro Gly Val Lys Leu Arg Val Thr Glu Gly Trp Asp Glu Asp
            20                  25                  30
```

```
Gly Leu His Ser Glu Glu Ser Leu His Tyr Glu Gly Arg Ala Val Asp
         35                  40                  45

Ile Thr Thr Ser Asp Arg Asp Arg Asn Lys Tyr Arg Met Leu Ala Arg
     50                  55                  60
```

( 2 ) INFORMATION FOR SEQ ID NO:18:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:18:

GGAATTCCCA GCAGNTGCTA AAGGAAGCAA GNGCTNAA            38

( 2 ) INFORMATION FOR SEQ ID NO:19:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:19:

TCATCGATGG ACCCAGATCG AAANCCNGCT CTC                 33

( 2 ) INFORMATION FOR SEQ ID NO:20:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:20:

GCTCTAGAGC TCNACNGCNA GANCGTNGC                      29

( 2 ) INFORMATION FOR SEQ ID NO:21:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:21:

AGCTGTCGAC GCGGCCGCTA CGTAGGTTAC CGACGTCAAG CTTAGATCTC    50

( 2 ) INFORMATION FOR SEQ ID NO:22:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:22:

AGCTGAGATC TAAGCTTGAC GTCGGTAACC TACGTAGCGG CCGCGTCGAC    50

( 2 ) INFORMATION FOR SEQ ID NO:23:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

GATCGGCCAG GCAGGCCTCG CGATATCGTC ACCGCGGTAT TCGAA    45

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

AGTGCCAGTC GGGGCCCCCA GGGCCGCGCC    30

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

TACCACAGCG GATGGTTCGG    20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

GTGGTGGTTA TGCCGATCGC    20

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

TAAGAGGCCT ATAAGAGGCG G    21

( 2 ) INFORMATION FOR SEQ ID NO:28:

( i ) SEQUENCE CHARACTERISTICS:

( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:28:

AAGTCAGCCC AGAGGAGACT          20

( 2 ) INFORMATION FOR SEQ ID NO:29:

( i ) SEQUENCE CHARACTERISTICS:
            ( A ) LENGTH: 6 amino acids
            ( B ) TYPE: amino acid
            ( D ) TOPOLOGY: linear ( i i ) MOLECULE TYPE: peptide ( v ) FRAGMENT TYPE: internal ( x i ) SEQUENCE DESCRIPTION: SEQ ID NO:29:

Cys  Gly  Pro  Gly  Arg  Gly
        1                   5

( 2 ) INFORMATION FOR SEQ ID NO:30:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:30:

AGCAGNTGCT AAAGGAAGCA AGNGCTNAA          29

( 2 ) INFORMATION FOR SEQ ID NO:31:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:31:

CTCNACNGCN AGANCKNGTN GCNA          24

( 2 ) INFORMATION FOR SEQ ID NO:32:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:32:

CTGCAGGGAT CCACCATGCG GCTTTTGACG AG          32

( 2 ) INFORMATION FOR SEQ ID NO:33:

( i ) SEQUENCE CHARACTERISTICS:
            ( A ) LENGTH: 31 base pairs
            ( B ) TYPE: nucleic acid
            ( C ) STRANDEDNESS: single ( D ) TOPOLOGY: linear ( i i ) MOLECULE TYPE: cDNA ( x i ) SEQUENCE DESCRIPTION: SEQ ID NO:33:

CTGCAGGGAT CCTTATTCCA CACGAGGGAT T                                                                    3 1